(12) United States Patent
Sukhatme

(10) Patent No.: US 6,852,691 B1
(45) Date of Patent: Feb. 8, 2005

(54) ANTI-ANGIOGENIC PEPTIDES AND METHODS OF USE THEREOF

(75) Inventor: Vikas P. Sukhatme, Newton Center, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 09/589,777

(22) Filed: Jun. 8, 2000

Related U.S. Application Data

(63) Continuation of application No. PCT/US98/26057, filed on Dec. 8, 1998.
(60) Provisional application No. 60/108,536, filed on Nov. 16, 1998, provisional application No. 60/082,663, filed on Apr. 22, 1998, and provisional application No. 60/067,888, filed on Dec. 8, 1997.

(51) Int. Cl.[7] .................. A61K 38/00; C07K 14/00
(52) U.S. Cl. .................. 514/12; 530/536; 530/350
(58) Field of Search .................. 514/12, 2; 530/300, 530/387.1, 350, 356; 536/23.1; 425/7.1; 424/192.1, 93.21; 435/91.1

(56) References Cited

U.S. PATENT DOCUMENTS

| | | | |
|---|---|---|---|
| 5,854,205 A | | 12/1998 | O'Reilly et al. ............ 514/2 |
| 6,080,728 A | * | 6/2000 | Mixson ................. 514/44 |

FOREIGN PATENT DOCUMENTS

| | | |
|---|---|---|
| WO | WO 97/15666 | 5/1997 |
| WO | WO 99/29855 | 6/1999 |
| WO | WO 99/29856 | 6/1999 |
| WO | WO 99/29878 | 6/1999 |
| WO | WO 00/17240 | 3/2000 |

OTHER PUBLICATIONS

Burgess et al., J of Cell Bio. 111:2129–2138, 1990.*
Lazar et al. Molecular and Cellular Biology 8:1247–1252, 1988.*
Bowie et al. Science, 247:1306–1310, 1990.*
Oh, et al., 1994, Proc. Natl. Acad. Sci., USA, vol. 91, pp. 4229–4233.*
O'Reilly, et al., "Endostatin: An Endogenous Inhibitor of Angiogenesis and Tumor Growth", *Cell* 88:277–285 (1997).
Ständker et al., "Isolation and Characterization of the Circulating Form of Human Endostatin", *FEBS*:129–133 (1997).
Dhanabal, et al., Endostatin: Yeast Production, Mutants, and Antitumor Effect in Renal Cell Carcinoma, *Cancer Research*, 59;189–197 (1999).
Hohenester, et al., "Crystal Structure of the Angiogenesis Inhibitor Endostatin at 1.5 Å Resolution", *EMBO Journal*:17(6):1656–1664 (1998).
Nguyen, et al., "Genetic Strategies for Anti–Angiogenic Therapy of Solid Tumors", p. 1 (1997).
Boehm, et al., "Zinc–Binding of Endostatin is Essential for Its Antiangiogenic Activity", *Biochemical and Biophysical Research Communication*, 252:190–194 (1998).
Ding et al., "Zinc–Dependent Dimers Observed in Crystals of Human Endostatin", *Proc. Natl. Acad. Sci.*, 95:10443–10448 (1998).
Folkman, J., "Endogenous Inhibitors of Angiogenesis", *The Harvey Lectures, Series* 92:65–82 (1998).
Dhanabal, et al., "Cloning, Expression, and In Vitro Activity of Human Endostatin", *Biochemical and Biophysical Research Communications*, 258:345–352 (1999).
Bachelot, T. et al., "Retrovirus–mediated gene transfer of an Angiostatin–Endostatin fusion protein with enhanced anti–tumor properties in vivo", *Proceedings of the 89th Annual Meeting of the American Association for Cancer Research* 39:271 (Mar. 1998).

* cited by examiner

*Primary Examiner*—Larry R. Helms
*Assistant Examiner*—Misook Yu
(74) *Attorney, Agent, or Firm*—Kathleen M. Williams; Barbara A. Gyure; Palmer & Dodge LLP

(57) ABSTRACT

EM 1, a novel anti-angiogenic protein, and a deletion mutant of endostatin, is described, as well as methods of making EM1, therapeutic compositions comprising EM1, and methods for using those compositions.

6 Claims, 31 Drawing Sheets endo sequence from Collagen XVIII.
Sequence Range: 1-555
Nucleotide 1 = Start for Endostatin and fragments EM1 and EM2.
EM1 fragment ends at nucleotide 525, EM2 fragment ends at
nucleotide 501.

```
         5         10        15        20        25        30        35        40        45
    CAT ACT CAT CAG GAC TTT CAG CCA GTG CTC CAC CTG GTG GCA CTG AAC
    GTA TGA GTA GTC CTG AAA GTC GGT CAC GAG GTG GAC CAC CGT GAC TTG 50        55        60        65        70        75        80        85        90        95
    ACC CCC CTG TCT GGA GGC ATG CGT GGT ATC CGT GGA GCA GAT TTC CAG
    TGG GGG GAC AGA CCT CCG TAC GCA CCA TAG GCA CCT CGT CTA AAG GTC 100       105       110       115       120       125       130       135       140
    TGC TTC CAG CAA GCC CGA GCC GTG GGC TTG TCG GGC ACC TTC CGG GCT
    ACG AAG GTC GTT CGG GCT CGG CAC CCG GAC AGC CCG TGG AAG GCC CGA 145       150       155       160       165       170       175       180       185       190
    TTC CTG TCC TCT AGG CTG CAG GAT CTC TAT AGC ATC GTG CGC CGT GCT
    AAG GAC AGG AGA TCC GAC GTC CTA GAG ATA TCG TAG CAC GCG GCA CGA 195       200       205       210       215       220       225       230       235       240
    GAC CGG GGG TCT GTG CCC ATC GTC AAC CTG AAG GAC GAG GTG CTA TCT
    CTG GCC CCC AGA CAC GGG TAG CAG TTG GAC TTC CTG CTC CAC GAT AGA 245       250       255       260       265       270       275       280       285
    CCC AGC TGG GAC TCC CTG TTT TCT GGC TCC CAG GGT CAA CTG CAA CCC
    GGG TCG ACC CTG AGG GAC AAA AGA CCG AGG GTC CCA GTT GAC GTT GGG 290       295       300       305       310       315       320       325       330       335
    GGG GCC CGC ATC TTT TCT TTT GAC GGC AGA GAT GTC CTG AGA CAC CCA
    CCC CGG GCG TAG AAA AGA AAA CTG CCG TCT CTA CAG GAC TCT GTG GGT 340       345       350       355       360       365       370       375       380
    GCC TGG CCG CAG AAG AGC GTA TGG CAC GGC TCG GAC CCC AGT GGG CGG
    CGG ACC GGC GTC TTC TCG CAT ACC GTG CCG AGC CTG GGG TCA CCC GCC 385       390       395       400       405       410       415       420       425       430
    AGG CTG ATG GAG AGT TAC TGT GAG ACA TGG CGA ACT GAA ACT ACT GGG
    TCC GAC TAC CTC TCA ATG ACA CTC TGT ACC GCT TGA CTT TGA TGA CCC 435       440       445       450       455       460       465       470       475       480
    GCT ACA GGT CAG GCC TCC TCC CTG CTG TCA GGC AGG CTC CTG GAA CAG
    CGA TGT CCA GTC CGG AGG AGG GAC GAC AGT CCG TCC GAG GAC CTT GTC 485       490       495       500       505       510       515       520       525
    AAA GCT GCG AGC TGC CAC AAC AGC TAC ATC GTC CTG TGC ATT GAG AAT
    TTT CGA CGC TCG ACG GTG TTG TCG ATG TAG CAG GAC ACG TAA CTC TTA 530       535       540       545       550       555
    AGC TTC ATG ACC TCT TTC TCC AAA TAG
    TCG AAG TAC TGG AGA AAG AGG TTT ATC
```

Fig. 1

Sequence Range: 1 to 184

```
     5      10     15     20     25     30     35     40     45
HTH  QDF    QPV    LHL    VAL    NTP    LSG    GMR    GIR    GAD    FQC    FQQ    ARA    VGL    SGT 50     55     60     65     70     75     80     85     90
FRA  FLS    SRL    QDL    YSI    VRR    ADR    GSV    PIV    NLK    DEV    LSP    SWD    SLF    SGS 95     100    105    110    115    120    125    130    135
QGQ  LQP    GAR    IFS    FDG    RDV    LRH    PAW    PQK    SVW    HGS    DPS    GRR    LME    SYC 140    145    150    155    160    165    170    175    180
ETW  RTE    TTG    ATG    QAS    SLL    SGR    LLE    QKA    ASC    HNS    YIV    LCI    ENS    FMT

SFS  K
```

Fig. 2

Control +bFGF

Endostatin 20 μg/ml

Negative control

Positive Control (VEGF)

VEGF + endostatin 20 μg

VEGF + endostain (10 μg)

VEGF + endosatin (10 μg) + polyclonal antiserum (50 μg)

| Construct Name | Primer Sequence | Cloning Sites | Vector | Protein Sequence |
|---|---|---|---|---|
| pET17b/ his.mendo | 5'-GGC ATA TGC ATA CTC ATC AGG- ACT TT-3' (up) (SEQ ID NO:3) | NdeI & XhoI | Prokaryotic expression, pET | MGHHHHHHHHSSGHIDDDDKH M-mendo (SEQ ID NO:5) |
| | 5' AAC TCG AGC TAT TTG GAG AAA- GAG GT-3' (DOWN) (SEQ ID NO:4) | | | |
| pET28a/ mendo | 5'-GGC ATA TGC ATA CTC ATC AGG- ACT TT-3' (up) (SEQ ID NO:3) | NdeI & NotI | Prokaryotic expression, pET | MGSSHHHHHHSSGLVPRGSHM- mendo (SEQ ID NO:7) |
| | 5'-AAG CGG CCG CCT ATT TG AGA- AAG AGG T-3' (down) (SEQ ID NO:6) | | | |
| pET28a/ EM-1 | 5' TTC CAT ATG CAT ACT CAT CAG- GAC TTT CAG CCA-3' (up) (SEQ ID NO:8) | | Prokaryotic expression, pET | MGSSHHHHHHSSGLVPRGSHM-me ndo (SEQ ID NO:7) |
| | 5' TTA GCG GCC GCC TAC TCA ATG- CAC AGG ACG ATG TA-3' (down) (SEQ ID NO:9) | | | |
| pET28a/ EM-2 | 5' TTC CAT ATG CAT ACT CAT CAG- GAC TTT CAG CCA-3' (up) (SEQ ID NO:8) | | Prokaryotic expression, pET | MGSSHHHHHHSSGLVPRGSHM-me ndo (SEQ ID NO:7) |
| | 5' TTA GCG GCC GCC TAG TTG TGG- CAG CTC GCA GCT TTC TG-3' (down) (SEQ ID NO:10) | | | |

Fig. 26A

| Construct Name | Primer Sequence | Cloning Sites | Vector | Protein Sequence |
|---|---|---|---|---|
| pPICZαA/ mendo | 5' GGG AAT TCC ATA CTC ATC AGG- ACT TT-3' (up) (SEQ ID NO:11) | EcoRI & NotI | Prokaryotic expression, yeast/pPICZαA | EF-mendo |
| | 5' AAG CGG CCG CCT ATT TGG AGA- AAG AGG T-3' (down) (SEQ ID NO:6) | | | |
| pPICZαA/ His.mendo | 5'AAG AAT TCC ATC ATC ATC ATC- ATC ACA GCA GC-3' (up) (SEQ ID NO:12) | EcoRI & NotI | Prokaryotic expression, yeast/pPICZαA | EFMGHHHHHHHHSSGHIDDDDK HM-mendo (SEQ ID NO:13) |
| | 5' AAG CGG CCG CCT ATT TGG AGA- AAG AGG T-3' (down) (SEQ ID NO:6) | | | |
| pPICZαA/ Hendo | 5' TTT GAA TTC GCC CAC AGC CAC- CGC GAC TTC CAG CCG GTG CTC- CA-3' (up) (SEQ ID NO:14) | EcoRI & NotI | Prokaryotic expression, yeast/pPICZαA | EF-hendo |
| | 5' AAA AGC GGC CGC CTA CTT GGA- GGC AGT CAT GAA GCT GTT CTC- AA-3' (down) (SEQ ID NO:15) | | | |
| pPICZαA/ Restin | 5' TTT TTT GAA TTC ATT TCA AGT- GCC AAT TAT GAG AAG CCT GCT CTG CAT TTG-3' (up) (SEQ ID NO:16) | EcoRI & NotI | Prokaryotic expression, yeast/pPICZαA | EF-restin |
| | 5' AAG AAT GCG GCC GCT TAC TTC- CTA GCG TCT GTC ATG AAA CTG- TTT TCG AT-3' (down) (SEQ ID NO:17) | | | |

Fig. 26B

| Construct Name | Primer Sequence | Cloning Sites | Vector | Protein Sequence |
|---|---|---|---|---|
| pPICZαA/ His.Restin | 5' AT TCC ATC ACC ATC ACC ATC- ACG- 3' (up) (SEQ ID NO:18)<br><br>5' AAT TCG TGA TGG TGA TGG TGA- TGG- 3' (down) (SEQ ID NO:19) | EcoRI (oligo insertion) | Eukaryotic (Yeast), Pichia, pPICZαA | EFHHHHHH-restin (SEQ ID NO:20) |
| pET28a/ apomigren | 5' TTC CAT ATG ATA TAC TCC TTT- GAT GGT CGA GAC ATA ATG AC-3' (up) (SEQ ID NO:21)<br><br>5' AAT GCG GCC GCT TAC TTC CTA- GCG TCT GTC ATG AAA CTG TTT- TCG AT-3' (down) (SEQ ID NO:22) | NdeI & NotI | Prokaryotic expression, pET | MGSSHHHHHHSSGLVPRGSHM-mendo (SEQ ID NO:7) |
| pET28a/ apomigren | 5' AAG AAT TCC ATC ATC ATC-ATC ACA GCA GC-3' (up) (SEQ ID NO:12)<br><br>5' AAT GCG GCC GCT TAC TTC CTA- GCG TCT GTC ATG AAA CTG TTT- TCG AT-3' (down) (SEQ D NO:22) | EcoRI & NotI | Eukaryotic (Yeast), Pichia, pPICZαA | EFMGSSHHHHHHSSGLVPRGSHM-apomigren (SEQ ID NO:23) |

Fig. 26C

ANTI-ANGIOGENIC PEPTIDES AND METHODS OF USE THEREOF

RELATED APPLICATIONS

This application is a continuation of international application PCT/US98/26057, filed Dec. 8, 1998, which claims priority to application 60/067,888, filed Dec. 8, 1997, 60/082,663, filed Apr. 22, 1998, and 60/108,536, filed Nov. 16, 1998, the entire teachings of all of which are incorporated herein by reference.

BACKGROUND OF THE INVENTION

The prognosis for metastatic cancer remains highly unfavorable. Despite advances in radiation therapy and chemotherapy, the long term survival of treated patients has shown only marginal improvement over the past few decades. The lack of significant treatment options available for metastatic cancers emphasizes the need to focus on the development of novel therapeutic strategies. In this regard, targeting tumor vasculature of solid tumors has recently shown promising results in several animal model systems (Baillie et al. (1995) *Br. J. Cancer* 72:257–67; Bicknell, R. (1994) *Ann. Oncol.* 5 (Suppl.) 4:45–50; Fan et al. (1995) *Trends Pharmacol. Sci.* 16:5766; Thorpe, P. E. and Burrows, F. J. (1995) *Breast Cancer Res. Treat.* 36:237–51; Burrows, F. J. and Thorpe, P. E. (1994) *Pharmacol. Ther.* 64:155–74). In a nude mouse model, for instance, introduction of a wild type VHL gene into 7860 cells, a RCC tumor cell line, inhibited tumor growth (Iliopoulos et al. (1995) *Nat. Med.* 1:822–26) and angiogenesis.

The growth of solid tumors beyond a few mm$^3$ depends on the formation of new blood vessels (Folkman, J. (1971) *N. Engl. J. Med.* 285:1182–86). Numerous studies have shown that both primary tumor and metastatic growth are angiogenesis-dependent (Folkman, J. (1971) *N. Engl. J. Med.* 285:1182–86; Folkman, J. (1972) *Ann. Surg.* 175:409–16; Folkman, J. and Shing, Y. (1992) *J. Biol. Chem.* 267:10931–34; Folkman, J. (1996) *Sci. Am.* 275:150–54). A number of angiogenesis inhibitors have been identified. Certain ones, such as platelet factor-4 (Maione et al (1990) *Science* 247:77–79; Gupta et al. (1995) *Proc. Natl. Acad. Sci. (USA)* 92:7799–7803), interferon α, interferon-inducible protein-10, and PEX (Angiolillo et al (1995) *J. Exp. Med.* 182:155–62; Strieter et al. (1995) *Biochem. Biophys. Res. Commun.* 210:51–57; Brooks et at (1998) *Cell* 92:391–400), are not "associated with tumors," whereas two others, angiostatin and endostatin, are "tumor-associated" (O'Reilly et al. (1994) *Cell* 79:315–28; O'Reilly et al. (1997) *Cell* 88:277–85). Angiostatin, a potent endogenous inhibitor of angiogenesis generated by tumor-infiltrating macrophages that upregulate matrix metalloelastase (Dong et al. (1997) *Cell* 88:801–10), inhibits the growth of a wide variety of primary and metastatic tumors (Lannutti et al (1997) *Cancer Res.* 57:5277–80; O'Reilly et al. (1994) *Cold Spring Harb. Symp. Quant. Biol.* 59:471–82; O'Reilly, M. S., (1997) *Exs.* 79:273–94; Sim et al. (1997) *Cancer Res.* 57:1329–34; Wu et al (1997) *Biochem. Biophys. Res. Commun.* 236:651–54).

Recently, O'Reilly, et al. ((1997) *Cell* 88:277–85) isolated endostatin, an angiogenesis inhibitor from a murine hemangioendothelioma cell line (EOMA). Circulating levels of a fragment of human endostatin have been detected in patients with chronic renal insufficiency with no detectable tumor, but this fragment had deletions, and no anti-angiogenic activity (Standker et al. (1997) *FEBS Lett.* 420:129–33). The amino terminal sequence of endostatin corresponds to the carboxy terminal portion of collagen XVIII. Endostatin is a specific inhibitor of endothelial proliferation and angiogenesis. Systemic administration of non-refolded precipitated protein expressed in *Escherichia coli* caused growth regression of Lewis lung carcinoma, T241 fibrosarcoma, B16 melanoma and EOMA (O'Reilly et al. (1997) *Cell* 88:277–85) cells in a xenograft model. Moreover, no drug resistance was noted in three of the tumor types studied. Repeated cycles of administration with endostatin have been reported to result in tumor dormancy (Boehm et al. (1997) *Nature* 390:404–407).

The results from these studies open new avenues for treatment of cancer and provide promising routes for overcoming the drug resistance often seen during chemotherapy. However, in all of these investigations, a non-refolded precipitated form of the inhibitor protein was administered in the form of a suspension to tumor bearing animals. In addition, large amounts of protein were required to cause tumor regression and to lead to tumor dormancy. As pointed out by Kerbel ((1997) *Nature* 390:335–36), oral drug equivalents of these proteins are needed. Mechanistic investigations could be undertaken if recombinant forms of these proteins were available in soluble form. Moreover, initial testing could be done in vitro with soluble protein before studying its efficacy under in vivo conditions. Furthermore, there have been reports that despite the great promise held by these proteins, evaluation of their clinical potential is stymied due to difficulties in producing enough of the protein to test, and inconsistent test results regarding their anti-angiogenic properties (King, R. T. (1998) *Wall Street J.*, page 1 November 12; Leff, D. N. (1998) *BioWorld Today* 9:1, October 20). There clearly exists at the present time a great need for a method of producing soluble forms of anti-angiogenic proteins in large amounts, and which have reliable properties in vitro and in vivo.

SUMMARY OF THE INVENTION

Described herein are novel mutants of endostatin, one of which, designated "EM 1," has anti-angiogenic activity similar or superior to that of wild type endostatin.

The invention relates to the discovery of an isolated anti-angiogenic peptide, wherein the C-terminal end of the peptide comprises the amino acid sequence SYIVLCIE (SEQ ID NO: 24), which has anti-angiogenic properties. Designated "EM 1," this protein comprises a mutated endostatin protein, where the mutation comprises a deletion of nine consecutive amino acids from the C-terminus of the mutated endostatin protein (e.g., NSFMTSFSK (SEQ ID NO: 25)). EM 1 terminates in the amino acid sequence SYIVLCIE (SEQ ID NO: 24). The invention also comprises isolated polynucleotides encoding EM 1, operably linked to expression sequences, and host cells transformed with such a construct. Antibodies to EM 1 are also disclosed.

The invention also relates to processes for producing EM 1, fusion proteins containing EM 1, and compositions comprising EM 1 or fusion products thereof. The invention also discloses methods of producing polynucleotides encoding EM 1.

In addition, the invention comprises methods for inhibiting angiogenic activity in mammalian tissue, comprising contacting the tissue with a composition comprising the EM 1, particularly to inhibit angiogenesis, which occurs in many diseases and conditions, including cancer.

The invention also discloses use of EM 1 to induce apoptosis, or antibodies of EM 1 to prevent apoptosis. The invention further discloses use of EM 1 in methods of gene therapy. The cells targeted may be any mammalian cells, particularly lymphocytes, blood cells, TIL cells, bone marrow cells, vascular cells, tumor cells, liver cells, muscle cells, and fibroblast cells.

BRIEF DESCRIPTION OF THE DRAWINGS

FIG. 1 is a diagram of the endostatin nucleotide sequence (SEQ ID NO: 1). The polynucleotide encoding EM 1 comprises the polynucleotide sequence through nucleotide 525. The polynucleotide encoding EM 2 comprises the polynucleotide sequence through nucleotide 501.

FIG. 2 is a diagram of the translation (SEQ ID NO:2) of the nucleic acid sequence of FIG. 1. EM 1 comprises the amino acid sequence through amino acid 175. EM 2 comprises the amino acid sequence through amino acid 167.

FIG. 12A shows migrated endothelial cells in the control (+bFGF, no endostatin), and FIG. 12B shows migrated endothelial cells treated with endostatin (20 μg/ml) with BFGF.

FIG. 14A is the negative control, FIG. 14B is the positive control (VEGF), and FIG. 14C shows the effect of endostatin plus VEGF.

FIG. 17A shows the effect of VEGF and endostatin (10 μg/pellet), and FIG. 17B shows the effect of endostatin (10 μg/pellet) plus polyclonal antiserum plus VEGF.

FIGS. 19A and 19B are control tumors, FIG. 19C shows a tumor treated with yeast-derived endostatin, FIG. 19D shows the effect of His.endostatin from bacteria, and FIG. 19E shows a tumor treated with His.endostatin from yeast.

FIG. 25A: NIH3T3 cell lysate; FIG. 25B: IMR-90 cell lysate; FIG. 25C: C-PAE cell lysate; FIG. 25D: NIH3T3 cell lysate.

FIGS. 26A, 26B, 26C are is a chart showing the constructs, primers, cloning sites, and vectors, used to clone and express various anti-angiogenic proteins. The amino acid sequences of the expressed proteins are also given.

DETAILED DESCRIPTION OF THE INVENTION

Figure 3:
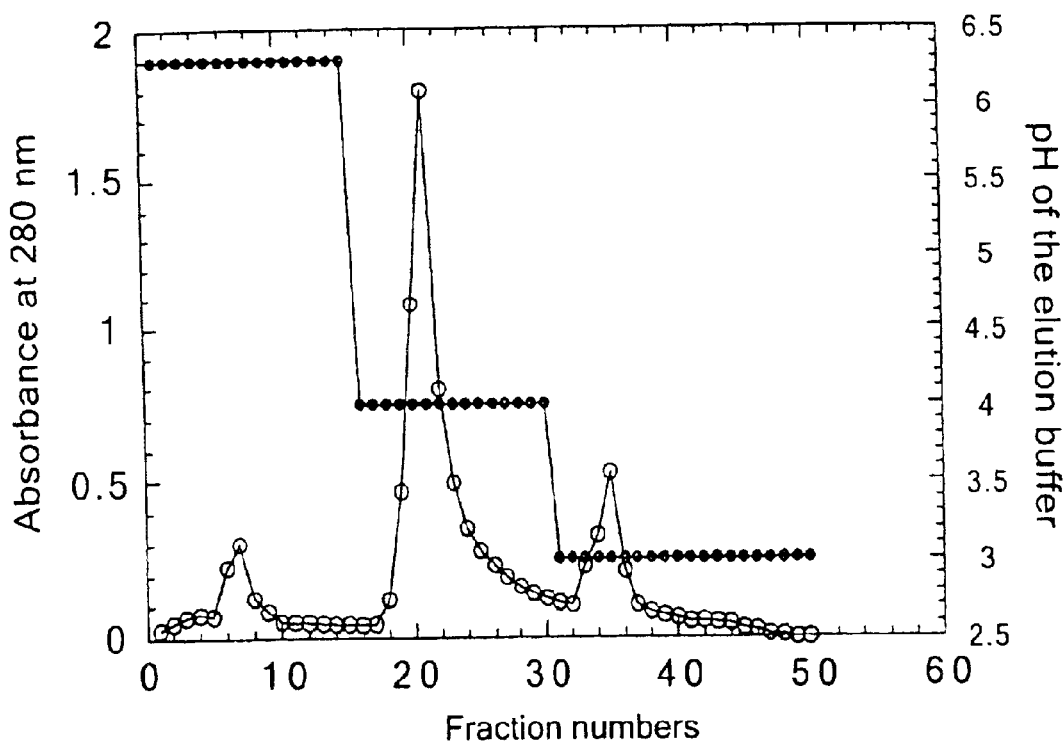
FIG. 3 is a graph showing the results of elution from an NI-NTA column. The fraction number is shown along the x-axis, and the absorbance at 280 nm for each fraction (○) is on the left y-axis. For each fraction, the pH of the eluting buffer (■) is shown on the right y-axis.

A wide variety of diseases are the result of undesirable angiogenesis. Put another way, many diseases and undesirable conditions could be prevented or alleviated if it were possible to stop the growth and extension of capillary blood vessels under some conditions, at certain times, or in particular tissues. Several anti-angiogenic proteins have been discovered (e.g., angiostatin, endostatin), problems have been reported regarding (1) the ability to produce the proteins in sufficient quantity to alow for proper testing of their properties, and (2) the reproducibility of the anti-angiogenic properties attributed to these proteins.

The present invention encompasses endostatin mutants, referred to herein as EMs. Specifically encompassed are two mutants of endostatin, designated "EM I" and "EM 2". These mutants were tested against whole endostatin. The mutants showed very different activity. Unexpectedly, one mutant ("EM 1") performed as well or better than whole endostatin, and the other ("EM 2") showed loss of anti-angiogenic activity. In a nude mouse model, growth of renal cell cancer (RCC) was suppressed by systemic administration of EM 1 at a rate of 20 mg/kg body weight. The inhibition of tumor growth is comparable to the inhibition obtained with wild-type endostatin. The difference in activity between EM 1 and EM 2 is surprising, given that there is a difference between them of only eight amino acid residues. EM 1 provides an advantage in treatment of angiogenic diseases in that increasingly smaller peptides are more potent on a weight basis, and may be able to better penetrate tissues.

In the present invention, EM 1, a novel anti-angiogenic protein, and a deletion mutant of endostatin, is described, as well as fragments, derivatives, fusion proteins and antibodies thereof. Methods of making the above are also described. Also disclosed are therapeutic compositions comprising EM 1, and methods for using those compositions. Polynucleotides encoding EM 1 are also described, as well as vectors and host cells comprising those polynucleotides. Compositions containing EM 1 as a biologically active ingredient are also described, as well as methods for using EM 1 to inhibit angiogenic activity in mammalian tissues, such as in treating diseases and conditions characterized by angiogenesis. The present invention includes compositions and methods for the detection and treatment of diseases and conditions that are mediated by or associated with angiogenesis. In addition, the invention includes use of EM 1 to induce apoptosis in a cell or tissue, and antibodies to EM 1 to inhibit apoptosis in a cell or tissue.

Specifically, EM 1 is a deletion mutant of endostatin, where the last nine amino acid residues have been deleted. EM 1 exists naturally as part of the collagen Type XVIII molecule, but it can be produced recombinantly, e.g., the polynucleotide sequence (FIG. 1, SEQ ID NO:1) encoding EM 1 protein (FIG. 2, SEQ ID NO:2) can amplified, e.g., with the forward and reverse primers listed in Table 1, below. The template nucleic acid used for the amplification can be from any mammal. Also encompassed by the present invention is mammalian EM1, fragments, mutants, derivatives or fusion proteins thereof.

TABLE 1

Constructs and primer sequences used to amplify anti-angiogenic proteins.

| Construct Name | Primer Sequence |
| --- | --- |
| pET17bhis.-mendo | 5'-GGC ATA TGC ATA CTC ATC AGG ACT TT-3' (up) (SEQ ID NO:3)<br>5' AAC TCG AGC TAT TTG GAG AAA GAG GT-3' (down) (SEQ ID NO:4) |
| pET28a/mendo | 5'-GGC ATA TGC ATA CTC ATC AGG ACT TT-3' (up) (SEQ ID NO:3)<br>5'-AAG CGG CCG CCT ATT TGG AGA AAG AGG T-3' (down) (SEQ ID NO:6) |
| pET28a/EM-1 | 5' TTC CAT ATG CAT ACT CAT CAG GAC TTT CAG CCA-3' (up) (SEQ ID NO:8)<br>5' TTA GCG GCC GCC TAC TCA ATG CAC AGG ACG ATG TA-3' (down) (SEQ ID NO:9) |
| pET28a/EM-2 | 5' TTC CAT ATG CAT ACT CAT CAG GAC TTT CAG CCA-3' (up) (SEQ ID NO:8)<br>5' TTA GCG GCC GCC TAG TTG TGG CAG CTC GCA GCT TTC TG-3' (down) (SEQ ID NO:10) |
| pPICZαA/ | 5' GGG AAT TCC ATA CTC ATC AGG ACT TT-3' (up) |

TABLE 1-continued

Constructs and primer sequences used to amplify anti-angiogenic proteins.

| Construct Name | Primer Sequence |
|---|---|
| mendo | (SEQ ID NO:11)<br>5' AAG CGG CCG CCT ATT TGG AGA AAG AGG T-3' (down) (SEQ ID NO:6) |
| pPICZαA/<br>His.mendo | 5' AAG AAT TCC ATC ATC ATC ATC ATC ACA GCA GC-3' (up) (SEQ ID NO:12)<br>5' AAG CGG CCG CCT ATT TGG AGA AAG AGG T-3' (down) (SEQ ID NO:6) |
| pPICZαA/<br>Hendo | 5' TTT GAA TTC GCC CAC AGC CAC CGC GAC TTC CAG CCG GTG CTC CA-3' (up) (SEQ ID NO:14)<br>5' AAA AGC GGC CGC CTA CTT GGA GGC AGT CAT GAA GCT GTT CTC AA-3' (down) (SEQ ID NO:15) |
| pPICZαA/<br>Restin | 5' TTT TTT GAA TTC ATT TCA AGT GCC AAT TAT GAG AAG CCT GCT CTG CAT TTG-3'(up) (SEQ ID NO:16)<br>5' AAG AAT GCG GCC GCT TAC TTC CTA GCG TCT GTC ATG AAA CTG TTT TCG AT-3' (down) (SEQ ID NO:17) |
| pPICZαA/<br>HIS.Restin | 5' AAT TCC ATC ACC ATC ACC ATC ACG-3' (up) (SEQ ID NO:18)<br>5' AAT TCG TGA TGG TGA TGG TGA TGG-3' (down) (SEQ ID NO:19) |
| pET28a/<br>apomigren | 5' TTC CAT ATG ATA TAC TCC TTT GAT GGT CGA GAC ATA ATG ACA-3' (up) (SEQ ID NO:21)<br>5' AAT GCG GCC GCT TAC TTC CTA GCG TCT GTC ATG AAA CTG TTT TCG AT-3' (down) (SEQ ID NO:22) |
| pPICZαA/<br>apomigren | 5' AAG AAT TCC ATC ATC ATC ATC ATC ACA GCA GC-3' (up) (SEQ ID NO:12)<br>5' AAT GCG GCC GCT TAC TTC CTA GCG TCT GTC ATG AAA CTG TTT TCG AT-3' (down) (SEQ ID NO:22) |

The resulting amplification product can then be cloned into a suitable vector. The term "primer" denotes a specific oligonucleotide sequence complementary to a target nucleotide sequence and used to hybridize to the target nucleotide sequence and serve as an initiation point for nucleotide polymerization catalyzed by either DNA polymerase, RNA polymerase or reverse transcriptase. "EM 1," as used herein, refers to a deletion mutant of endostatin, wherein the last nine amino acid residues have been deleted (ie., NSFMTS-FSK (SEQ ID NO: 25)), and the term is intended to include fragments, mutants, homologs, analogs, and allelic variants of the amino acid sequence of SEQ ID NO:2). Although EM 1 was originally cloned from mouse nucleic acid, it performs better than intact type endostatin (i.e., endostatin that has not been mutated) in standard assays. The term EM 1 is therefore intended to include any mammalian sequence substantially similar to EM 1 as described herein, as well as mammalian EM 1 fragments, mutants, homologs, analogs and allelic variants of the mammalian EM 1 amino acid sequence. Also, specifically encompassed by the present invention are human endostatin mutants, and more specifcally, the human deletion mutant equivalent of EM 1.

It is to be understood that the present invention is contemplated to include any derivatives of EM 1 that have endothelial inhibitory activity (e.g., the capability of a composition to inhibit angiogenesis in general and, for example, to inhibit the growth or migration of bovine capillary endothelial cells in culture in the presence of fibroblast growth factor, angiogenesis-associated factors, or other known growth factors). The present invention includes the entire EM 1 protein, derivatives of the EM 1 protein and biologically-active fragments of the EM 1 protein. These include proteins with EM 1 activity that have amino acid substitutions or have sugars or other molecules attached to amino acid functional groups. The present invention also includes genes that code for EM 1 and the EM 1 receptor, and to proteins that are expressed by those genes.

The invention also encompasses a composition comprising an isolated polynucleotide encoding EM 1, as well as vectors and host cells containing such a polynucleotide, and processes for producing EM 1 and its fragments, mutants, homologs, analogs and allelic variants. The term "vector" as used herein means a carrier into which pieces of nucleic acid may be inserted or cloned, which carrier functions to transfer the pieces of nucleic acid into a host cell. Such a vector may also bring about the replication and/or expression of the transferred nucleic acid pieces. Examples of vectors include nucleic acid molecules derived, e.g., from a plasmid, bacteriophage, or mammalian, plant or insect virus, or non-viral vectors such as ligand-nucleic acid conjugates, liposomes, or lipid-nucleic acid complexes. It may be desirable that the transferred nucleic acid molecule is operably linked to an expression control sequence to form an expression vector capable of expressing the transferred nucleic acid. Such transfer of nucleic acids is generally called "transformation," and refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome. "Operably linked" refers to a situation wherein the components described are in a relationship permitting them to function in their intended manner, e.g., a control sequence "operably linked" to a coding sequence is ligated in such a manner that expression of the coding sequence is achieved under conditions compatible with the control sequence. A "coding sequence" is a polynucleotide sequence which is transcribed into mRNA and translated into a polypeptide when placed under the control of (e.g., operably linked to) appropriate regulatory sequences. The boundaries of the coding sequence are determined by a translation start codon at the 5'-terminus and a translation stop codon at the 3'-terminus. Such boundaries can be naturally-occurring, or can be introduced into or added the polynucleotide sequence by methods known in the art. A coding sequence can include, but is not limited to, mRNA, cDNA, and recombinant polynucleotide sequences.

The vector into which the cloned polynucleotide is cloned may be chosen because it functions in a prokaryoticorganism, or alternatively, it is chosen because it functions in a eukaryotic organism. Two examples of vectors which allow for both the cloning of a polynucleotide encoding the EM 1 protein, and the expression of that protein from the polynucleotide, are the pET28(a) vector (Novagen, Madison, Wis., USA) and a modified pPICZαA vector (InVitrogen, San Diego, Calif., USA), which allow expression of the protein in bacteria and yeast, respectively.

Once a polynucleotide has been cloned into a suitable vector, it can be transformed into an appropriate host cell. By "host cell" is meant a cell which has been or can be used as the recipient of transferred nucleic acid by means of a vector. Host cells can prokaryotic or eukaryotic, mammalian, plant, or insect, and can exist as single cells, or as a collection, e.g., as a culture, or in a tissue culture, or in a tissue or an organism. Host cells can also be derived from normal or diseased tissue from a multicellular organism, e.g., a mammal. Host cell, as used herein, is intended to include not only the original cell which was transformed with a nucleic acid, but also descendants of such a cell, which still contain the nucleic acid.

In one embodiment, the isolated polynucleotide encoding the anti-angiogenic protein additionally comprises a polynucleotide linker encoding a peptide. Such linkers are known to those of skill in the art and, for example the linker can comprise at least one aditional codon encoding at least one additional amino acid. Typically the linker comprises one to about twenty or thirty amino acids. The polynucleotide linker is translated, as is the polynucleotide encoding the anti-angiogenic protein, resulting in the expression of an anti-angiogenic protein with at least one additional amino acid residue at the amino or carboxyl terminus of the anti-angiogenic protein. Some linkers attached to anti-angiogenic proteins are illustrated in FIG. 26. Importantly, the additional amino acid, or amino acids, do not compromise the activity of the anti-angiogenic protein.

After inserting the selected polynucleotide into the vector, the vector is transformed into an appropriate prokaryotic strain and the strain is cultured (e.g., maintained) under suitable culture conditions for the production of the biologically active anti-antiogenic protein, thereby producing a biologically active anti-angiogenic protein, or mutant, derivative, fragment or fusion protein thereof. In one embodiment, the invention comprises cloning of a polynucleotide encoding an anti-angiogenic protein into the vectors pET17b or pET28a, which are then transformed into bacteria. The bacterial host strain then expresses the anti-angiogenic protein. Typically the anti-angiogenic proteins are produced in quantities of about 1020 milligrams, or more, per liter of culture fluid.

In another embodiment of the present invention, the eukaryotic vector comprises a yeast vector. As described herein, one method uses a pPICzα plasmid wherein the plasmid contains a multiple cloning site. The multiple cloning site inserted into the multiple cloning site a His.Tag motif. Additionally the vector can be modified to add a NdeI site, or other suitable restriction sites. Such sites are well known to those of skill in the art. Anti-angiogenic proteins produced by this embodiment comprise a histidine tag motif (His.tag) comprising one, or more histidines, typically about 5–20 histidines. Surprisingly, this His.tag does not compromise anti-angiogenic activity.

In this embodiment, a preferred yeast expression system is *Pichia pastoris*. Again, the biologically active protein is typically produced at concentrations of about 10–20 milligrams per liter of culture medium (fluid).

One method of producing EM 1, for example, is to amplify the polynucleotide of SEQ ID NO:1, clone it into an expression vector, e.g., pET28(a), pPICZαA, or some other expression vector, transform the vector containing the polynucleotide of SEQ ID NO:1 into a host cell capable of expressing the polypeptide encoded by the polynucleotide, culturing the transformed host cell under culture conditions suitable for expressing the protein, and then extracting and purifying the protein from the culture. Exemplary methods of producing anti-angiogenic proteins in general, and EM in particular, are provided in the Examples below, and also in PCT/US98/25892, "Methods of Producing Anti-Angiogenic Proteins," by Vikas P. Sukhatme, filed Dec. 7, 1998, and its U.S. designation U.S. Ser. No. 09/589,483, the entire teachings of which are herein incorporated by reference. The EM 1 protein may also be expressed as a product of transgenic animals, e.g., as a component of the milk of transgenic cows, goats, sheep or pigs, or as a product of a transgenic plant, e.g., combined or linked with starch molecules in maize.

EM 1 may also be produced by conventional, known methods of chemical synthesis. Methods for constructing the proteins of the present invention by synthetic means are known to those skilled in the art. The synthetically-constructed EM 1 protein sequences, by virtue of sharing primary, secondary or tertiary structural and/or conformational characteristics with e.g., recombinantly-produced EM 1, may possess biological properties in common therewith, including biological activity. Thus, the synthetically-constructed EM 1 protein sequences may be employed as biologically active or immunological substitutes for e.g., recombinantly-produced, purified EM 1 protein in screening of therapeutic compounds and in immunological processes for the development of antibodies.

The EM 1 protein is useful in inhibiting angiogenesis, as determined in standard assays, and provided in the Examples below. EM 1 does not inhibit the growth of other cells types, e.g., IMR-90 cells, or IC-21 cells.

As used herein, the term "angiogenesis" means the generation of new blood vessels into a tissue or organ, and involves endothelial cell proliferation. Under normal physiological conditions, humans or animals undergo angiogenesis only in very specific restricted situations. For example, angiogenesis is normally observed in wound healing, fetal and embryonal development, and formation of the corpus luteum, endometrium and placenta. The tern "endothelium" means a thin layer of flat epithelial cells that lines serous cavities, lymph vessels, and blood vessels. "Anti-angiogenic activity" therefore refers to the capability of a composition to inhibit the growth of blood vessels. The growth of blood vessels is a complex series of events, and includes localized breakdown of the basement membrane lying under the individual endothelial cells, proliferation of those cells, migration of the cells to the location of the future blood vessel, reorganization of the cells to form a new vessel membrane, cessation of endothelial cell proliferation, and, incorporation of pericytes and other cells that support the new blood vessel wall. "Anti-angiogenic activity" as used herein therefore includes interruption of any or all of these stages, with the end result that formation of new blood vessels is inhibited.

Anti-angiogenic activity may include endothelial inhibiting activity, which refers to the capability of a composition to inhibit angiogenesis in general and, for example, to inhibit the growth or migration of bovine capillary endothelial cells in culture in the presence of fibroblast growth factor, angiogenesis-associated factors, or other known growth factors. A "growth factor" is a composition that stimulates the growth, reproduction, or synthetic activity of cells. An "angiogenesis-associated factor" is a factor which either inhibits or promotes angiogenesis. An example of an angiogenesis-associated factor is an angiogenic growth factor, such as basic fibroblastic growth factor (bFGF), which is an angiogenesis promoter. Another example of an angiogenesis-associated factor is an angiogenesis inhibiting factor such as e.g., angiostatin (see, e.g., U.S. Pat. No. 5,801,012, U.S. Pat. No. 5,837,682, U.S. Pat. No. 5,733,876, U.S. Pat. No. 5,776,704, U.S. Pat. No. 5,639,725, U.S. Pat. No. 5,792,845, WO 96/35774, WO 95/29242, WO 96/41194, WO 97/23500) or endostatin (see, e.g., WO 97/15666).

By "substantially the same biological activity" or "substantially the same or superior biological activity" is meant that a composition has anti-angiogenic activity, and behaves similarly as does EM 1, as determined in standard assays. "Standard assays" include, but are not limited to, those protocols used in the molecular biological arts to assess anti-angiogenic activity, cell cycle arrest, and apoptosis. Such assays include, but are not limited to, assays of endothelial cell proliferation, endothelial cell migration, cell cycle analysis, and endothelial cell tube formation, detection of apoptosis, e.g., by apoptotic cell morphology or Annexin V-FITC assay, chorioallantoic membrane (CAM) assay, and inhibition of renal cancer tumor growth in nude mice. Such assays are provided in the Examples below, and in U.S. Ser. No. 60/067,888, filed Dec. 8, 1997, U.S. Ser. No. 60/082,663, filed Apr. 22, 1998, U.S. Ser. No. 60/108,536, filed Nov. 16, 1998, and in U.S. S.N. PCT/US98/26058, "Restin and Methods of Use Thereof," by Vikas P. Sukhatme, filed Dec. 8, 1998, and in its U.S. designation U.S. Ser. No. 09/589,774 and PCT/US98/25892, "Methods of Producing Anti-Angiogenic Proteins," by Vikas P. Sukhatme, filed Dec. 7, 1998, and in its U.S. designation U.S. Ser. No. 09/589,483 the entire teachings of all of which are herein incorporated by reference. Such methods are also included in Dhanabal et al. (1999) ("Endostatin Induces Endothelial Cell Apoptosis, "*J. Biol. Chem.*, 274:11721–6), and in Dhanabal et al. (1999) ("Cloning, Expression and in vitro Activity of Human Endostatin," *Bioch. Biophys. Res. Commun.* 258:345–52). Evaluating the $ED_{50}$ of a mutant in one of the assays described herein is a useful method of comparing activities.

As used herein, "$ED_{50}$" is an abbreviation for the amount of a composition which reduces a biological effect by one-half, relative to the biological effect seen in the absence of the composition.

The invention also describes fragments, mutants, homologs and analogs of EM 1. A "fragment" of EM 1 any amino acid sequence shorter that the EM 1 molecule, comprising at least 25 consecutive amino acids of the EM 1 polypeptide. Such mutants may or may not also comprise additional amino acids derived from the process of cloning, e.g., amino acid residues or amino acid sequences corresponding to full or partial linker sequences. To be encompassed by the present invention, such mutants, with or without such additional amino acid residues, must have substantially the same biological activity as the natural or full-length version of the reference polypeptide.

By "mutant" of EM 1 is meant a polypeptide that includes any change in the amino acid sequence relative to the amino acid sequence of the equivalent reference EM 1 polypeptide. Such changes can arise either spontaneously or by manipulations by man, by chemical energy (e.g., X-ray), or by other forms of chemical mutagenesis, or by genetic engineering, or as a result of mating or other forms of exchange of genetic information. Mutations include, e.g., base changes, deletions, insertions, inversions, translocations, or duplications. Mutant forms of EM 1 may display either increased or decreased anti-angiogenic activity relative to the equivalent reference EM 1 polynucleotide, and such mutants may or may not also comprise additional amino acids derived from the process of cloning, e.g., amino acid residues or amino acid sequences corresponding to full or partial linker sequences.

By "analog" of EM 1 is meant a non-natural molecule substantially similar to either the entire EM 1 molecule or a fragment or allelic variant thereof, and having substantially the same or superior biological activity. Such analogs are intended to include derivatives (e.g., chemical derivatives, as defined above) of the biologically active EM 1, as well as its fragments, mutants, homologs, and allelic variants, which derivatives exhibit a qualitatively similar agonist or antagonist effect to that of the unmodified EM 1 polypeptide, fragment, mutant, homolog, or allelic variant.

By "allele" of EM 1 is meant a polypeptide sequence containing a naturally-occurring sequence variation relative to the polypeptide sequence of the reference EM 1 polypeptide. By "allele" of a polynucleotide encoding the EM 1 polypeptide is meant a polynucleotide containing a sequence variation relative to the reference polynucleotide sequence encoding the reference EM 1 polypeptide, where the allele of the polynucleotide encoding the EM 1 polypeptide encodes an allelic form of the EM 1 polypeptide.

It is possible that a given polypeptide may be either a fragment, a mutant, an analog, or allelic variant of EM 1, or it may be two or more of those things, e.g., a polypeptide may be both an analog and a mutant of the EM 1 polypeptide. For example, a shortened version of the EM 1 molecule (e.g., a fragment of EM 1) may be created in the laboratory. If that fragment is then mutated through means known in the art, a molecule is created that is both a fragment and a mutant of EM 1. In another example, a mutant of EM 1 may be created, which is later discovered to exist as an allelic of EM 1 in some mammalian individuals. Such a mutant EM 1 molecule would therefore be both a mutant and an allelic variant of EM 1. Such combinations of fragments, mutants, allelic variants, and analogs are intended to be encompassed in the present invention.

Encompassed by the present invention are proteins that have substantially the same amino acid sequence as EM 1, or polynucleotides that have substantially the same nucleic acid sequence as the polynucleotide encoding EM 1. "Substantially the same sequence" means a nucleic acid or polypeptide that exhibits at least about 70% sequence identity with a reference sequence, e.g., another nucleic acid or polypeptide, typically at least about 80% sequence identity with the reference sequence, preferably at least about 90% sequence identity, more preferably at least about 95% identity, and most preferably at least about 97% sequence identity with the reference sequence. The length of comparison for sequences will generally be at least 75 nucleotide bases or 25 amino acids, more preferably at least 150 nucleotide bases or 50 amino acids, and most preferably 243–264 nucleotide bases or 81–88 amino acids. "Polypeptide" as used herein indicates a molecular chain of amino acids and does not refer to a specific length of the product. Thus, peptides, oligopeptides and proteins are included within the definition of polypeptide. This term is also intended to include polypeptide that have been subjected to post-expression modifications such as, for example, glycosylations, acetylations, phosphorylations and the like. EM 1, in general, has less than 70% amino acid sequence identity with endostatin.

"Sequence identity," as used herein, refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length), of the positions in two peptide or compound sequences are identical, then the two sequences are 50% identical; if 90% of the positions, e.g., 9 of 10 are matched, the two sequences share 90% sequence identity. By way of example, the amino acid sequences $R_{20}R_2R_8R_{11}R_6R_{15}$ and $R_9R_1R_{14}R_{11}R_6R_{15}$ have 3 of 6 positions in common, and therefore share 50% sequence identity, while the sequences $R_{20}R_2R_8R_{11}R_6R_{15}$ and $R_1R_{14}R_{11}R_6R_{15}$ have 3 of 5 positions in common, and therefore share 60% sequence identity. The identity between two sequences is a direct function of the number of matching or identical positions. Thus, if a portion of the reference sequence is deleted in a particular peptide, that deleted section is not counted for purposes of calculating sequence identity, e.g., $R_{20}R_2R_8R_{11}R_6R_{15}$ and $R_{20}R_2R_8R_{11}R_{15}$ have 5 out of 6 position in common, and therefore share 83.3% sequence identity.

Identity is often measured using sequence analysis software e.g., BLASTN or BLASTP (available at the world wide web site ("www") for the National Center for Biotechnology Information (".ncbi") of the National Institutes of Health (".nih") of the U.S. government (".gov"), in the "/BLASTP/" directory [http://www.ncbi.nlm.nih.gov/BLAST/]). The default parameters for comparing two sequences (e.g., "Blast"-ing two sequences against each other[, http://www.ncbi.nlm.nih.gov/gorf/b12.html]) by BLASTN (for nucleotide sequences) are reward for match=1, penalty for mismatch=−2, open gap=5, extension gap=2. When using BLASTP for protein sequences, the default parameters are reward for match=0, penalty for mismatch=0, open gap=1, and extension gap=1.

When two sequences share "sequence homology," it is meant that the two sequences differ from each other only by conservative substitutions. For polypeptide sequences, such conservative substitutions consist of substitution of one amino acid at a given position in the sequence for another amino acid of the same class (e.g., amino acids that share characteristics of hydrophobicity, charge, pK or other conformational or chemical properties, e.g., valine for leucine, arginine for lysine), or by one or more non-conservative amino acid substitutions, deletions, or insertions, located at positions of the sequence that do not alter the conformation or folding of the polypeptide to the extent that the biological activity of the polypeptide is destroyed. Examples of "conservative substitutions" include substitution of one non-polar (hydrophobic) residue such as isoleucine, valine, leucine or methionine for another; the substitution of one polar (hydrophilic) residue for another such as between arginine and lysine, between glutamine and asparagine, between threonine and serine; the substitution of one basic residue such as lysine, arginine or histidine for another; or the substitution of one acidic residue, such as aspartic acid or glutamic acid for another, or the use of a chemically derivatized residue in place of a non-derivatized residue; provided that the polypeptide displays the requisite biological activity. Two sequences which share sequence homology may called "sequence homologs."

Homology, for polypeptides, is typically measured using sequence analysis software (e.g., Sequence Analysis Software Package of the Genetics Computer Group, University of Wisconsin Biotechnology Center, 1710 University Avenue, Madison, Wis. 53705). Protein analysis software matches similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Also encompassed by the present invention are chemical derivatives of EM 1. "Chemical derivative" refers to a subject polypeptide having one or more residues chemically derivatized by reaction of a functional side group. Such derivatized residues include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl dervatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substitute for lysine; 3-methylhistidine may be substituted for histidine; homoserine may be substituted for serine; and ornithine may be substituted for lysine.

Polynucleotides encoding EM 1 can be cloned out of isolated DNA or a cDNA library. Nucleic acids polypeptides, referred to herein as "isolated" are nucleic acids or polypeptides substantially free (i.e., separated away from) the material of the biological source from which they were obtained (e.g., as exists in a mixture of nucleic acids or in cells), which may have undergone further processing. "Isolated" nucleic acids or polypeptides include nucleic acids or polypeptides obtained by methods described herein, similar methods, or other suitable methods, including essentially pure nucleic acids or polypeptides, nucleic acids or polypeptides produced by chemical synthesis, by combinations of chemical or biological methods, and recombinantly produced nucleic acids or polypeptides whch are isolated. An isolated polypeptide therefore means one which is relatively free of other proteins, carbohydrates, lipids, and other cellular components with which it is normally associated. An isolated nucleic acid is not immediately contiguous with (i.e., covalently linked to) both of the nucleic acids with which it is immediately contiguous in the naturally-occurring genome of the organism from which the nucleic acid is derived. The term, therefore, includes, for example, a nucleic acid which is incorporated into a vector (e.g., an autonomously replicating virus or plasmid), or a nucleic acid which exists as a separate molecule independent of other nucleic acids such as a nucleic acid fragment produced by chemical means or restriction endonuclease treatment.

The polynucleotides and proteins of the present invention can also be used to design probes to isolate other anti-angiogenic proteins. Exceptional methods are provided in U.S. Pat. No. 5,837,490, by Jacobs et al., the entire teachings of which are herein incorporated by reference in their entirety. The design of the oligonucleotide probe should preferably follow these parameters: (a) It should be designed to an area of the sequence which has the fewest ambiguous bases ("Cws"), if any, and (b) It should be designed to have a $T_m$ of approx. 80° C. (assuming 2° C. for each A or T and 4° for each G or C).

The oligonucleotide should preferably be labeled with $\gamma$-$^{32}$ P ATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately $4 \times 10^6$ dpm/pmole. The bacterial culture containing the pool of full-length clones should preferably be thawed and 100 μl of the stock used to inoculate a sterile culture flask containing 25 ml of sterile L-broth containing ampicillin at 100 μg/ml. The culture should preferably be grown to saturation at 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 μg/ml and agar at 1.5% in a 150 mm petri dish when grown overnight at 37° C. Other known methods of obtaining distinct, well-separated colonies can also be employed.

Standard colony hybridization procedures should then be used to transfer the colonies to nitrocellulose filters and lyse, denature and bake them. Highly stringent condition are those that are at least as stringent as, for example, 1×SSC at 65° C., or 1×SSC and 50% formamide at 42° C. Moderate stringency conditions are those that are at least as stringent as 4×SSC at 65° C., or 4×SSC and 50% formamide at 42° C. Reduced stringency conditions are those that are at least as stringent as 4×SSC at 50° C., or 6×SSC and 50% formamide at 40° C.

The filter is then preferably incubated at 65° C. for 1 hour with gentle agitation in 6×. SSC (20× stock is 175.3 g NaCl/liter, 88.2 g Na citrate/liter, adjusted to pH 7.0 with NaOH) containing 0.5% SDS, 100 µg/ml of yeast RNA, and 10 mM EDTA (approximately 10 mL per 150 mm filter). Preferably, the probe is then added to the hybridization mix at a concentration greater than or equal to $1 \times 10^6$ dpm/mL. The filter is then preferably incubated at 65° C. with gentle agitation overnight. The filter is then preferably washed in 500 mL of 2×SSC/0.5% SDS at room temperature without agitation, preferably followed by 500 mL of 2×SSC/0.1% SDS at room temperature with gentle shaking for 15 minutes. A third wash with 0.1×SSC/0.5% SDS at 65° C. for 30 minutes to 1 hour is optional. The filter is then preferably dried and subjected to autoradiography for sufficient time to visualize the positives on the X-ray film. Other known hybridization methods can also be employed. The positive colonies are then picked, grown in culture, and plasmid DNA isolated using standard procedures. The clones can then be verified by restriction analysis, hybridization analysis, or DNA sequencing.

The present invention also includes fusion proteins and chimeric proteins comprising EM 1, its fragments, mutants, homologs, analogs, and allelic variants. A fusion or chimeric protein can consist of a multimer of a single protein, e.g., repeats of EM 1 or repeats of apomigren, or the fusion and chimeric proteins can be made up of several proteins, e.g., EM 1 and apomigren. The fusion proteins can comprise a combination of two or more known anti-angiogenic proteins (e.g., angiostatin, endostatin, restin, or apomigren, or biologically active fragments thereof), or an anti-angiogenic protein in combination with a targeting agent (e.g., endostatin with epidermal growth factor (EGF) or RGD peptides), or an anti-angiogenic protein in combination with an immunoglobulin molecule (e.g., endostatin and IgG, specifically with the Fc portion removed). As used herein, "restin" is a protein comprising about 170 to about 200 amino acid residues, and has at least 70% sequence identity with the C-terminus of the NC10 domain of the al chain of human Type XV collagen. As used herein, "apomigren" is a fragment of restin, and comprises the last 80 to 90 contiguous amino acids corresponding to the C-terminus of the NC10 domain of the al chain of human Type XV collagen. The fusion and chimeric proteins can also include EM 1, its fragments, mutants, homologs, analogs, and allelic variants, and other anti-angiogenic proteins, e.g., endostatin or angiostatin. The term "fusion protein" as used herin can also encompass additonal components for e.g., delivering a chemotherapeutic agent, wherein a polynucleotide encoding the chemotherapeutic agent is linked to the polynucleotide encoding the anti-angiogenic protein. Fusion proteins can also encompass multimers of the anti-angiogenic protein, e.g., a dimer or trimer of endostatin. Such fusion proteins can be linked together via post-translational modification (e.g., chemically linked), or the entire fusion protein may be made recombinantly.

Also included in the inventions are compositions containing, as a biological ingredient, EM 1, as well as its fragments, mutants, homologs, analogs, and allelic variants to inhibit or enhance angiogenesis in mammalian tissues, and use of such compositions in the diagnosis, prognosis, and treatment of diseases and conditions characterized by, or associated with, angiogenic activity or lack thereof. Such methods can involve administration by oral, topical, injection, implantation, sustained release, or other delivery methods.

The invention includes use of EM 1, and its fragments, mutants, homologs, analogs, allelic variants, and fusion and chimeric proteins as biologically-active agents in compositions for the purpose of treating diseases or conditions that are associated with angiogenic activity. Methods of treating such diseases include contacting the affected tissue with a composition comprising EM 1, its fragments, mutants, homologs, analogs, or allelic variants.

The present invention includes the method of treating an angiogenesis-mediated disease with a therapeutically effective amount of EM 1, or a biologically active fragment thereof, or combinations of EM 1 fragments that possess anti-angiogenic activity, or EM 1 agonists and antagonists. Angiogenesis-mediated diseases include, but are not limited to, cancers, solid tumors, blood-born tumors (e.g., leukemias), tumor metastasis, benign tumors (e.g., hemangiomas, acoustic neuromas, neurofibromas, trachomas, and pyogenic granulomas), rheumatoid arthritis, psoriasis, ocular angiogenic diseases (e.g., diabetic retinopathy, retinopathy of prematurity, macular degeneration, corneal graft rejection, neovascular glaucoma, retrolental fibroplasia, rubeosis), Osler-Webber Syndrome, myocardial angiogenesis, plaque neovascularization, telangiectasia, hemophiliac joints, angiofibroma, and wound granulation. EM 1 is useful in the treatment of diseases of excessive or abnormal stimulation of endothelial cells. These diseases include, but are not limited to, intestinal adhesions, Crohn's disease, atherosclerosis, scleroderma, and hypertrophic scars (i.e., keloids). EM 1 can be used as a birth control agent by preventing vascularization required for embryo implantation. EM 1 is useful in the treatment of diseases that have angiogenesis as a pathologic consequence such as cat scratch disease (*Rochele minalia quintosa*) and ulcers (*Heliobacter pylori*). EM 1 can also be used to prevent dialysis graft vascular access stenosis, and obesity, e.g., by inhibiting capillary formation in adipose tissue, thereby preventing its expansion. EM 1 can also be used to treat localized (e.g., nonmetastisized) diseases. "Cancer" means neoplastic growth, hyperplastic or proliferative growth or a pathological state of abnormal cellular development and includes solid tumors, non-solid tumors, and any abnormal cellular proliferation, such as that seen in leukemia. As used herein, "cancer" also means angiogenesis-dependent cancers and tumors, i.e., tumors that require for their growth (expansion in volume and/or mass) an increase in the number and density of the blood vessels supplying them with blood. "Regression" refers to the reduction of tumor mass and size. As used herein, the term "therapeutically effective amount" means the total amount of each active component of the composition or method that is sufficient to show a meaningful patient benefit, i.e., treatment, healing, prevention or amelioration of the relevant medical condition, or an increase in rate of treatment, healing, prevention or amelioration of such conditions. When applied to a combination, the term refers to combined amounts of the active ingredients that result in the therapeutic effect, whether administered in combination, serially or simultaneously.

Alternatively, where an increase in angiogenesis is desired, e.g., in wound healing, or in post-infarct heart tissue, antibodies or antisera to the EM 1 protein can be used to block localized, native anti-angiogenic proteins and processes, and thereby increase formation of new blood vessels so as to inhibit atrophy of tissue.

EM 1 may be used in combination with other compositions and procedures for the treatment of diseases. For example, a tumor may be treated conventionally with surgery, radiation, chemotherapy, or immunotherapy combined with EM 1 and then EM 1 may be subsequently administered to the patient to extend the dormancy of micrometastases and to stabilize and inhibit the growth of any residual primary tumor. EM 1, EM 1 fragments, EM 1 antisera, EM 1 receptor agonists, EM 1 receptor antagonists, or combinations thereof, can also be combined with other anti-angiogenic compounds, or proteins, fragments, antisera, receptor agonists, receptor antagonists of other anti-angiogenic proteins (e.g., angiostatin, endostatin, restin, apomigren). Additionally, EM 1, EM 1 fragments, EM 1 antisera, EM 1 receptor agonists, EM 1 receptor antagonists, or combinations thereof, are combined with pharmaceutically acceptable excipients, and optionally sustained-release matrix, such as biodegradable polymers, to form therapeutic compositions. The compositions of the present invention may also contain other anti-angiogenic proteins or chemical compounds, such as endostatin, angiostatin, restin and apomigren (both of which are described in PCT/US98/26058, "Restin and Methods of use Thereof", by Vikas P. Sukhatme, filed Dec. 8, 1998, and in U.S. Ser. No. 09/589,774, Restin and Methods of Use Thereof", by Rikas P. Sukhatme, filed Jun. 8, 2000, the entire teachings of which are herein incorporated by reference), and mutants, fragments, and analogs thereof. The compositions may further contain other agents which either enhance the activity of the protein or compliment its activity or use in treatment, such as chemotherapeutic or radioactive agents. Such additional factors and/or agents may be included in the composition to produce a synergistic effect with protein of the invention, or to minimize side effects. Additionally, administration of the composition of the present invention may be administered concurrently with other therapies, e.g., administered in conjunction with a chemotherapy or radiation therepy regimen.

The invention includes methods for inhibiting angiogenesis in mammalian tissues by contacting the tissue with a composition comprising the proteins of the invention. By "contacting" is meant not only topical application, but also those modes of delivery that introduce the composition into the tissues, or into the cells of the tissues.

Use of timed release or sustained release delivery systems are also included in the invention. Such systems are highly desirable in situations where surgery is difficult or impossible, e.g., patients debilitated by age or the disease course itself, or where the risk-benefit analysis dictates control over cure.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The angiogenesis-modulating therapeutic composition of the present invention may be a solid, liquid or aerosol and may be administered by any known route of administration. Examples of solid compositions include pills, creams, and implantable dosage units. The pills may be administered orally, the creams may be administered topically. The implantable dosage unit may be administered locally, for example at a tumor site, or which may be implanted for systemic release of the angiogenesis-modulating composition, for example subcutaneously. Examples of liquid composition include formulations adapted for injection subcutaneously, intravenously, intraarterially, and formulations for topical and intraocular administration. Examples of aersol formulation include inhaler formulation for administration to the lungs.

The EM 1 proteins and protein fragments with the anti-angiogenic activity described above can be provided as isolated and substantially purified proteins and protein fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the EM 1 may be incorporated into biodegradable polymers allowing for sustained release of the compound, the polymers being implanted in the vicinity of where drug delivery is desired, for example, at the site of a tumor or implanted so that the EM 1 is slowly released systemically. Osmotic minipumps may also be used to provide controlled delivery of high concentrations of EM 1 through cannulae to the site of interest, such as directly into a metastatic growth or into the vascular supply to that tumor. The biodegradable polymers and their use are described, for example, in detail in Brem et al. (1991) (*J. Neurosurg.* 74:4414), which is hereby incorporated by reference in its entirety.

The compositions containing a polypeptide of this invention can be administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier or vehicle.

Modes of administration of the compositions of the present inventions include intravenous, intramuscular, intraperitoneal, intrasternal, subcutaneous and intraarticular injection and infusion. Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents. Prevention of the action of microorganisms may be ensured by the inclusion of various antibacterial and antifungal agents such as paraben, chlorobutanol, phenol sorbic acid and the like. It may also be desirable to include isotonic agents such as sugars, sodium chloride and the like. Prolonged absorption of the injectable pharmaceutical form may be brought about by the inclusion of agents, such as aluminum monostearate and gelatin, which delay absorption. Injectable depot forms are made by forming microencapsule matrices of the drug in biodegradable polymers such as polylactide-polyglycolide, poly (orthoesters) and poly(anhydrides). Depending upon the ratio of drug to polymer and the nature of the particular polmer employed, the rate of drug release can be controlled. Depot injectable formulations are also prepared by entrapping the drug in liposomes or microemulsions which are compatible with body tissues. The injectable formulations may be sterilized, for example, by filtration through a bacterial-retaining filter or by incorporating sterilizing agents in the form of sterile solid compositions which can be dissolved or dispersed in sterile water or other sterile injectable media just prior to use.

The therapeutic compositions of the present invention can include pharmaceutically acceptable salts of the components therein, e.g., which may be derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge, et al. describe pharmaceutically acceptable salts in detail in *J. Pharmaceutical Sciences* (1977) 66;1 et seq., which is incorporated herein by reference. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. The salts may be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptonoate, hexanoate, fumarate, hydrochloride, hydrobromide, hydroiodide, 2-hydroxymethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

As used herein, the terms "pharmaceutically acceptable," "physiologically tolerable" and grammatical variations thereof as they refer to compositions, carriers, diluents and reagents, are used interchangeably and represent that the materials are capable of administration to or upon a mammal with a minimum of undesirable physiological effects such as nausea, dizziness, gastric upset and the like. The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipeints which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The EM 1 polypeptides of the present invention can also be included in a composition comprising a prodrug. As used herein, the term "prodrug" refers to compounds which are rapidly transformed in vivo to yield the parent compound, for example, by enzymatic hydrolysis in blood. A thorough discussion is provided in T. Higuchi and V. Stella, *Prodrugs as Novel Delivery Systems*, Vol. 14 of the ACS Symposium Series and in Edward B. Roche, ed., *Bioreversible Carriers in Drug Design*, American Pharmaceutical Association and Permagon Press, 1987, both of which are incorporated herein by reference. As used herein, the term "pharmaceutically acceptable prodrug" refers to (1) those prodrugs of the compounds of the present invention which are, within the scope of sound medical judgement, suitable for use in contact with the tissues of humans and animals without undue toxicity, irritation, allergic response and the like, commensurate with a suitable benefit-to-risk ratio and effective for their intended use and (2) zwitterionic forms, where possible, of the parent compound.

The dosage of the EM 1 of the present invention will depend on the disease state or condition being treated and other clinical factors such as weight and condition of the human or animal and the route of administration of the compound. For treating humans or animals, about 10 mg/kg of body weight to about 20 mg/kg of body weight of the EM 1 protein or the apomigren protein can be administered. In combination therapies, e.g., the EM 1 protein of the invention in combination with radiotherapy, chemotherapy, or immunotherapy, it may be possible to reduce the dosage, e.g., to about 0.1 mg/kg of body weight to about 0.2 mg/kg of body weight. Depending upon the half-life of the EM 1 in the particular animal or human, the EM 1 can be administered between several times per day to once a week. It is to be understood that the present invention has application for both human and veterinary use. The methods of the present invention contemplate single as well as multiple administrations, given either simultaneously or over an extended period of time. In addition, EM 1 can be administered in conjuntion with other forms of therapy, e.g., chemotherapy, radiotherapy, or immunotherapy.

The EM 1 formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The EM 1 formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

When a therapeutically effective amount of protein of the present invention is administered orally, the EM 1 protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringers Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Preferred unit dosage formulations are those containing a daily dose or unit, daily sub-dose, or an appropriate fraction thereof, of the administered ingredient. It should be understood that in addition to the ingredients, particularly mentioned above, the formulations of the present invention may include other agents conventional in the art having regard to the type of formulation in question. Optionally, cytotoxic agents may be incorporated or otherwise combined with EM 1 proteins, or biologically functional protein fragments thereof, to provide dual therapy to the patient.

The therapeutic compositions are also presently valuable for veterinary applications. Particularly domestic animals and thoroughbred horses, in addition to humans, are desired patients for such treatment with proteins of the present invention.

Cytotoxic agents such as ricin, are linked to EM 1, and high affinity EM 1 protein fragments, thereby providing a tool for destruction of cells that bind EM 1. These cells may be found in many locations, including but not limited to, micrometastases and primary tumors. Proteins linked to cytotoxic agents are infused in a manner designed to maximize delivery to the desired location. For example, ricin-linked high affinity EM 1 fragments are delivered through a cannula into vessels supplying the target site or directly into the target. Such agents are also delivered in a controlled manner through osmotic pumps coupled to infusion cannulae. A combination of EM 1 antagonists may be co-applied with stimulators of angiogenesis to increase vascularization of tissue. This therapeutic regimen provides an effective means of destroying metastatic cancer.

Additional treatment methods include administration of EM 1, EM 1 fragments, EM 1 analogs, EM 1 antisera, or EM 1 receptor agonists and antagonists linked to cytotoxic agents. It is to be understood that the EM 1 can be human or animal in origin. EM 1 can also be produced synthetically by chemical reaction or by recombinant techniques in conjunction with expression systems. EM 1 can also be produced by enzymatically cleaving isolated endostatin to generate proteins having anti-angiogenic activity. EM 1 may also be produced by compounds that mimic the action of endogenous enzymes that cleave endostatin to EM 1. EM 1 production may also be modulated by compounds that affect the activity of endostatin-cleaving enzymes.

The present invention also encompasses gene therapy whereby a polynucleotide encoding EM 1, or a mutant, fragment, or fusion protein thereof, is introduced and regulated in a patient. Various methods of transferring or delivering DNA to cells for expression of the gene product protein, otherwise referred to as gene therapy, are disclosed in *Gene Transfer into Mammalian Somatic Cells* in vivo, N. Yang (1992) *Crit. Rev. Biotechn.* 12(4):335–356, which is hereby incorporated by reference. Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Strategies for treating these medical problems with gene therapy include therapeutic strategies such as identifying the defective gene and then adding a functional gene to either replace the function of the defective gene or to augment a slightly functional gene; or prophylactic strategies, such as adding a gene for the product protein that will treat the condition or that will make the tissue or organ more susceptible to a treatment regimen. As an example of a prophylactic strategy, a gene such as EM 1 may be placed in a patient and thus prevent occurrence of angiogenesis; or a gene that makes tumor cells more susceptible to radiation could be inserted and then radiation of the tumor would cause increased killing of the tumor cells.

Many protocols for transfer of EM 1 DNA or EM 1 regulatory sequences are envisioned in this invention. Transfection of promoter sequences, other than one normally found specifically associated with EM 1, or other sequences which would increase production of EM 1 protein are also envisioned as methods of gene therapy. An example of this technology is found in Transkaryotic Therapies, Inc., of Cambridge, Mass., using homologous recombination to insert a "genetic switch" that turns on an erythropoietin gene in cells. See *Genetic Engineering News*, Apr. 15, 1994. Such "genetic switches" could be used to activate EM 1 (or the EM 1 receptor) in cells not normally expressing EM 1 (or the EM 1 receptor).

Gene transfer methods for gene therapy fall into three broad categories: physical (e.g., electroporation, direct gene transfer and particle bombardment), chemical (e.g., lipid-based carriers, or other non-viral vectors) and biological (e.g. virus-derived vector and receptor uptake). For example, non-viral vectors may be used which include liposomes coated with DNA. Such liposome/DNA complexes may be directly injected intravenously into the patient. It is believed that the liposome/DNA complexes are concentrated in the liver where they deliver the DNA to macrophages and Kupffer cells. These cells are long lived and thus provide long term expression of the delivered DNA. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the transformed cells are cells growing in culture, such as tissue culture cells, and not particular cells from a particular patient. These "laboratory cells" are transfected, the transfected cells are selected and expanded for either implantation into a patient or for other uses.

In vivo gene transfer involves introducing the DNA into the cells of the patient when the cells are within the patient. Methods include using virally mediated gene transfer using a noninfectious virus to deliver the gene in the patient or injecting naked DNA into a site in the patient and the DNA is taken up by a percentage of cells in which the gene product protein is expressed. Additionally, the other methods described herein, such as use of a "gene gun," may be used for in vitro insertion of EM 1 DNA or EM 1 regulatory sequences.

Chemical methods of gene therapy may involve a lipid based compound, not necessarily a liposome, to transfer the DNA across the cell membrane. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols. To direct the tissue-specific expression of foreign genes, cis-acting regulatory elements or promoters that are known to be tissue-specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Viral vectors that have been used for gene therapy protocols include but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA complexed with a nuclear core protein and polymerase (pol) enzymes, encased by a protein core (gag) and surrounded by a glycoprotein envelope (env) that determines host range. The genomic structure of retroviruses include the gag, pol, and env genes enclosed at by the 5' and 3' long terminal repeats (LTR). Retroviral vector systems exploit the fact that a minimal vector containing the 5' and 3' LTRs and the packaging signal are sufficient to allow vector packaging, infection and integration into target cells providing that the viral structural proteins are supplied in trans in the packaging cell line. Fundamental advantages of retroviral vectors for gene transfer include efficient infection and gene expression in most cell types, precise single copy vector integration into target cell chromosomal DNA, and ease of manipulation of the retroviral genome.

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product proteins at high levels. Adenoviral vectors have high efficiencies of infectivity, even with low titers of virus. Additionally, the virus is fully infective as a cell free virion so injection of producer cell lines are not necessary. Another potential advantage to adenoviral vectors is the ability to achieve long term expression of heterologous genes in vivo.

Mechanical methods of DNA delivery include fusogenic lipid vesicles such as liposomes or other vesicles for membrane fusion, lipid particles of DNA incorporating cationic lipid such as lipofectin, polylysine-mediated transfer of DNA, direct injection of DNA, such as microinjection of DNA into germ or somatic cells, pneumatically delivered DNA-coated particles, such as the gold particles used in a "gene gun," and inorganic chemical approaches such as calcium phosphate transfection. Particle-mediated gene transfer methods were first used in transforming plant tissue. With a particle bombardment device, or "gene gun," a motive force is generated to accelerate DNA-coated high density particles (such as gold or tungsten) to a high velocity that allows penetration of the target organs, tissues or cells. Particle bombardment can be used in in vitro systems, or with ex vivo or in vivo techniques to introduce DNA into cells, tissues or organs. Another method, ligand-mediated gene therapy, involves complexing the DNA with specific ligands to form ligand-DNA conjugates, to direct the DNA to a specific cell or tissue.

It has been found that injecting plasmid DNA into muscle cells yields high percentage of the cells which are transfected and have sustained expression of marker genes. The DNA of the plasmid may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Electroporation for gene transfer uses an electrical current to make cells or tissues susceptible to electroporation-mediated mediated gene transfer. A brief electric impulse with a given field strength is used to increase the permeability of a membrane in such a way that DNA molecules can penetrate into the cells. This technique can be used in in vitro systems, or with ex vivo or in vivo techniques to introduce DNA into cells, tissues or organs.

Carrier mediated gene transfer in vivo can be used to transfect foreign DNA into cells. The carrier-DNA complex can be conveniently introduced into body fluids or the bloodstream and then site-specifically directed to the target organ or tissue in the body. Both liposomes and polycations, such as polylysine, lipofectins or cytofectins, can be used. Liposomes can be developed which are cell specific or organ specific and thus the foreign DNA carried by the liposome will be taken up by target cells. Injection of immunoliposomes that are targeted to a specific receptor on certain cells can be used as a convenient method of inserting the DNA into the cells bearing the receptor. Another carrier system that has been used is the asialoglycoprotein/polylysine conjugate system for carrying DNA to hepatocytes for in vivo gene transfer.

The transfected DNA may also be complexed with other kinds of carriers so that the DNA is carried to the recipient cell and then resides in the cytoplasm or in the nucleoplasm. DNA can be coupled to carrier nuclear proteins in specifically engineered vesicle complexes and carried directly into the nucleus.

Gene regulation of EM 1 may be accomplished by administering compounds that bind to the EM 1 gene, or control regions associated with the EM 1 gene, or its corresponding RNA transcript to modify the rate of transcription or translation. Additionally, cells transfected with a DNA sequence encoding EM 1 may be administered to a patient to provide an in vivo source of EM 1. For example, cells may be transfected with a vector containing a nucleic acid sequence encoding EM 1. The transfected cells may be cells derived from the patient's normal tissue, the patient's diseased tissue, or may be non-patient cells.

For example, tumor cells removed from a patient can be transfected with a vector capable of expressing the EM 1 protein of the present invention, and reintroduced into the patient. The transfected tumor cells produce EM 1 levels in the patient that inhibit the growth of the tumor. Patients may be human or non-human animals. Cells may also be transfected by non-vector, or physical or chemical methods known in the art such as electroporation, ionoporation, or via a "gene gun."Additionally, EM 1 DNA may be directly injected, without the aid of a carrier, into a patient. In particular, EM 1 DNA may be injected into skin, muscle or blood.

The gene therapy protocol for transfecting EM 1 into a patient may either be through integration of the EM 1 DNA into the genome of the cells, into minichromosomes or as a separate replicating or non-replicating DNA construct in the cytoplasm or nucleoplasm of the cell. EM 1 expression may continue for a long-period of time or may be reinjected periodically to maintain a desired level of the EM 1 protein in the cell, the tissue or organ or a determined blood level.

In addition, the invention encompasses antibodies and antisera, which can be used for testing of novel anti-angiogenic proteins, and can also be used in diagnosis, prognosis, or treatment of diseases and conditions characterized by, or associated with, angiogenic activity or lack thereof. Such antibodies and antisera can also be used to upregulate angiogenesis where desired, erg., in post-infarct heart tissue, antibodies or antisera to the EM 1 protein can be used to block localized, native anti-angiogenic proteins and processes, and increase formation of new blood vessels and inhibit atrophy of heart tissue.

Such antibodies and antisera can be combined with pharmaceutically-acceptable compositions and carriers to form diagnostic, prognostic or therapeutic compositions. The term "antibody" or "antibody molecule" refers to a population of immunoglobulin molecules and/or immunologically active portions of immunoglobulin molecules, i.e., molecules that contain an antibody combining site or paratope.

Passive antibody therapy using antibodies that specifically bind EM 1 can be employed to modulate angiogenic-dependent processes such as reproduction, development, and wound healing and tissue repair. In addition, antisera directed to the Fab regions of EM 1 antibodies can be administered to block the ability of endogenous EM 1 antisera to bind EM 1.

The EM 1 of the present invention also can be used to generate antibodies that are specific for the inhibitor and its receptor. The antibodies can be either polyclonal antibodies or monoclonal antibodies. These antibodies that specifically bind to the EM 1 or EM 1 receptors can be used in diagnostic methods and kits that are well known to those of ordinary skill in the art to detect or quantify the EM 1 or EM 1 receptors in a body fluid or tissue. Results from these tests can be used to diagnose or predict the occurrence or recurrence of a cancer and other angiogenic mediated diseases.

The invention also includes use of EM 1, antibodies to EM 1, and compositions comprising EM 1 and/or its antibodies in diagnosis or prognosis of diseases characterized by angiogenic activity. As used herein, the term "prognostic method" means a method that enables a prediction regarding the progression of a disease of a human or animal diagnosed with the disease, in particular, an angiogenesis dependent disease. The term "diagnostic method" as used herein means a method that enables a determination of the presence or type of angiogenesis-dependent disease in or on a human or animal.

The EM 1 can be used in a diagnostic method and kit to detect and quantify antibodies capable of binding EM 1. These kits would permit detection of circulating EM 1 antibodies which indicates the spread of micrometastases in the presence of EM 1 secreted by primary tumors in situ. Patients that have such circulating anti-EM 1 antibodies may be more likely to develop multiple tumors and cancers, and may be more likely to have recurrences of cancer after treatments or periods of remission. The Fab fragments of these anti-EM 1 antibodies may be used as antigens to generate anti-EM EM 1 Fab-fragment antisera which can be used to neutralize anti-EM 1 antibodies. Such a method would reduce the removal of circulating EM 1 by anti-EM 1 antibodies, thereby effectively elevating circulating EM 1 levels.

The present invention also includes isolation of receptors specific for EM 1. Protein fragments that possess high affinity binding to tissues can be used to isolate the EM 1 receptor on affinity columns. Isolation and purification of the EM 1 receptor is a fundamental step towards elucidating the mechanism of action of EM 1. Isolation of an EM 1 receptor and identification of EM 1 agonists and antagonists will facilitate development of drugs to modulate the activity of the EM 1 receptor, the final pathway to biological activity. Isolation of the receptor enables the construction of nucleotide probes to monitor the location and synthesis of the receptor, using in situ and solution hybridization technology.

Further, the gene for the EM 1 receptor can be isolated, incorporated into an expression vector and transfected into cells, such as patient tumor cells to increase the ability of a cell type, tissue or tumor to bind EM 1 and inhibit local angiogenesis.

EM 1 proteins are employed to develop affinity columns for isolation of the EM 1 receptor from cultured tumor cells. Isolation and purification of the EM 1 receptor is followed by amino acid sequencing. Using this information the gene or genes coding for the EM 1 receptor can be identified and isolated. Next, cloned nucleic acid sequences are developed for insertion into vectors capable of expressing the receptor. These techniques are well known to those skilled in the art. Transfection of the nucleic acid sequence(s) coding for EM 1 receptor into tumor cells, and expression of the receptor by the transfected tumor cells enhances the responsiveness of these cells to endogenous or exogenous EM 1 and thereby decreasing the rate of metastatic growth.

Angiogenesis-inhibiting proteins of the present invention can be synthesized in a standard microchemical facility and purity checked with HPLC and mass spectrophotometry. Methods of protein synthesis, HPLC purification and mass spectrophotometry are commonly known to those skilled in these arts. EM 1 proteins and EM 1 receptors proteins are also produced in recombinant E. coli or yeast expression systems, and purified with column chromatography.

Different protein fragments of the intact EM 1 molecule can be synthesized for use in several applications including, but not limited to the following; as antigens for the development of specific antisera, as agonists and antagonists active at EM 1 binding sites, as proteins to be linked to, or used in combination with, cytotoxic agents for targeted killing of cells that bind EM 1. The amino acid sequences that comprise these proteins are selected on the basis of their position on the exterior regions of the molecule and are accessible for binding to antisera. The amino and carboxyl termini of EM 1, as well as the mid-region of the molecule are represented separately among the fragments to be synthesized.

The synthetic protein fragments of EM 1 have a variety of uses. The protein that binds to the EM 1 receptor with high specificity and avidity is radiolabeled and employed for visualization and quantitation of binding sites using autoradiographic and membrane binding techniques. This application provides important diagnostic and research tools. Knowledge of the binding properties of the EM 1 receptor facilitates investigation of the transduction mechanisms linked to the receptor.

EM 1 and EM 1-derived proteins can be coupled to other molecules using standard methods. The amino and carboxyl termini of EM 1 both contain tyrosine and lysine residues and are isotopically and nonisotopically labeled with many techniques, for example radiolabeling using conventional techniques (tyrosine residues-chloramine T, iodogen, lactoperoxidase; lysine residues-Bolton-Hunter reagent). These coupling techniques are well known to those skilled in the art. Alternatively, tyrosine or lysine is added to fragments that do not have these residues to facilitate labeling of reactive amino and hydroxyl groups on the protein. The coupling technique is chosen on the basis of the functional groups available on the amino acids including, but not limited to amino, sulfydral, carboxyl, amide, phenol, and imidazole. Various reagents used to effect these couplings include among others, glutaraldehyde, diazotized benzidine, carbodiimide, and p-benzoquinone.

EM 1 proteins are chemically coupled to isotopes, enzymes, carrier proteins, cytotoxic agents, fluorescent molecules, chemiluminescent, bioluminescent and other compounds for a variety of applications. The efficiency of the coupling reaction is determined using different techniques appropriate for the specific reaction. For example, radiolabeling of an EM 1 protein with $^{125}$I is accomplished using chloramine T and Na$^{125}$I of high specific activity. The reaction is terminated with sodium metabisulfite and the mixture is desalted on disposable columns. The labeled protein is eluted from the column and fractions are collected. Aliquots are removed from each fraction and radioactivity measured in a gamma counter. In this manner, the unreacted Na$^{125}$I is separated from the labeled EM 1 protein. The protein fractions with the highest specific radioactivity are stored for subsequent use such as analysis of the ability to bind to EM 1 antisera.

In addition, labeling EM 1 proteins with short lived isotopes enables visualization of receptor binding sites in vivo using positron emission tomography or other modern radiographic techniques to locate tumors with EM 1 binding sites.

Systematic substitution of amino acids within these synthesized proteins yields high affinity protein agonists and antagonists to the EM 1 receptor that enhance or diminish EM 1 binding to its receptor. Such agonists are used to suppress the growth of micrometastases, thereby limiting the spread of cancer. Antagonists to EM 1 are applied in situations of inadequate vascularization, to block the inhibitory effects of EM 1 and promote angiogenesis. For example, this treatment may have therapeutic effects to promote wound healing in diabetics.

The EM 1 protein of the present invention can also be used as a nutritional source or supplement. Such uses include without limitation use as a protein or amino acid supplement, use as a carbon source, use as a nitrogen source and use as a source of carbohydrate. In such cases, the EM 1 protein of the invention can be added to the food of a particular organism, or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

The invention is further illustrated by the following examples, which are not meant to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Cells and Cell Lines

Cell line 786-0 (ATCC No. CRL-1932), a renal clear cell carcinoma line; C-PAE (ATCC No. CCL-209), a bovine pulmonary arterial endothelial cell line and ECV304 (ATCC No. CRL-1998), a human endothelial cell line were all obtained from ATCC (American Type Culture Collection, 10801 University Boulevard, Manassas, Va., 20110-2209, USA). The cell lines were maintained in either DMEM (786-0 and C-PAE) or M199 (ECV304), supplemented with 10% fetal calf serum, 100 U/ml of penicillin, 100 μg/ml of streptomycin and 2 mM L-glutamine. The cDNA clone for mouse endostatin pBACPak 8 was kindly provided by B. R. Olsen, Department of Cellular Biology, Harvard Medical School, Boston. The prokaryotic expression vector pET17b was purchased from Novagen (Madison, Wis., USA). The yeast expression system, *Pichia pastoris* (pPICZαA) was purchased from InVitrogen (San Diego, Calif., USA). Restriction enzymes and Vent DNA polymerase were purchased from New England Biolabs (Beverly, Mass., USA).

Example 2

Cloning and Expression of Mouse Endostatin and Mutants into a Prokaryotic System The gene encoding mouse endostatin was amplified from the pBACPak 8 plasmid and expressed initially in the pET expression system. The sequence encoding the carboxy terminal portion of mouse collagen XVIII was amplified by amplification using Vent DNA polymerase, with the endostatin pBACPak 8 vector as a template. The primers used were 5'-GGC ATA TGC ATA CTC ATC AGG ACT TT-3' (SEQ ID NO:3) and 5'-AAC TCG AGCTA TTT GGA GAA AGA GGT-3' (SEQ ID NO:4). Amplification was carried out for 30 cycles with the following parameters: 94° C. for denaturation, 60° C. for annealing, and 72° C. for extension, each for 1 minute. The amplified DNA fragment (555 bp) was purified using a QIAquick purification kit, digested with NdeI and XhoI (these restriction sites are underlined in the primers above), and ligated into the expression vector pET17bhis (Dhanabal et al. (1995) *J. Immunol. Methods.* 182:165–175). Initial transformation was carried out with the host strain HMS174 (Novagen, Madison, Wis., USA). Positive clones were sequenced on both strands. The desired clones were finally transformed into BL2 1 (DE3) (Novagen, Madison, Wis., USA) for expression. The expression of recombinant protein in the pET system was carried out as recommended by the manufacturer (Novagen, Madison, Wis., USA).

A Ni-NTA agarose column was used to purify the recombinant protein. Protein present in inclusion bodies was solubilized in 8 M urea and purified under denaturing condition is as described by O'Reilly et al (1997) (*Cell* 88:277–285). The results are shown in FIG. 3, which is a graph showing the absorbance at 280 nm of the eluted fractions (○). Also plotted is the pH of the elution buffer (●). FIG. 3 shows a small peak around fractions 7–8, a sharp peak around fractions 21–22, and another small peak around fraction 35.

Figure 4:
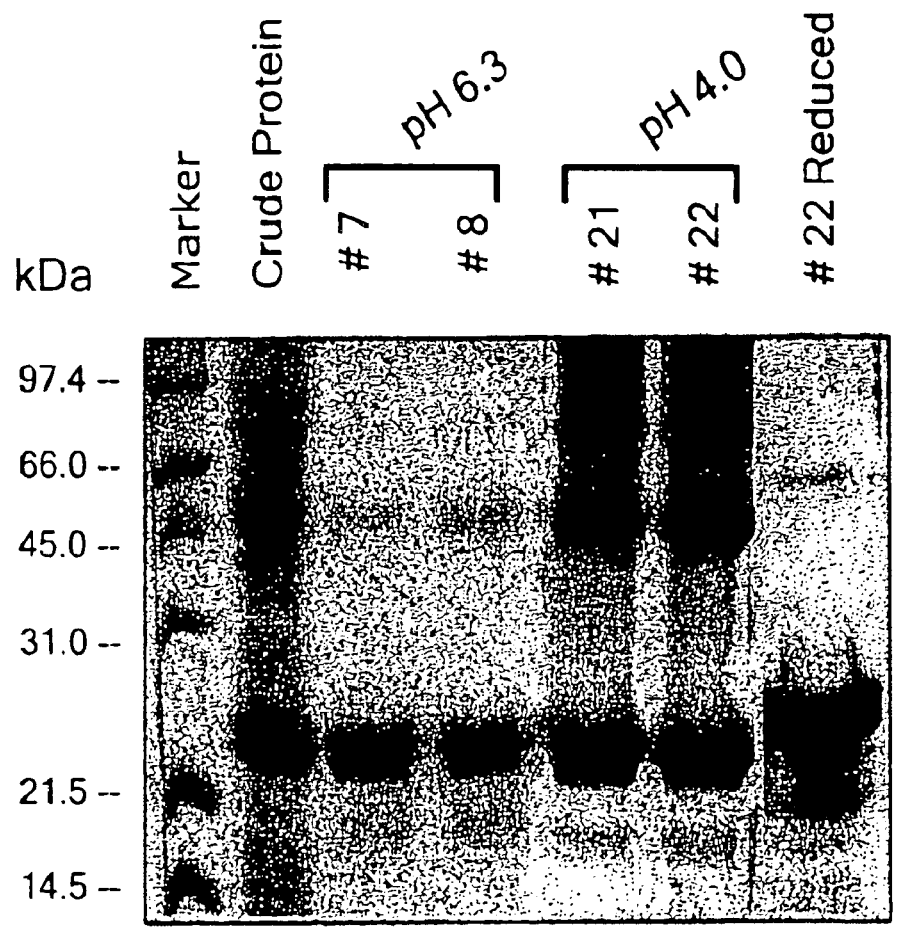
FIG. 4 shows a 12% non-reducing SDS-PAGE gel of protein produced from the prokaryotic expression system. Sizes in kDa are shown on the left, and the first lane contains size markers. Lane 2 contains crude protein, lanes 3 and 4 contain samples from fractions 7 and 8, which were eluted at pH 6.3. Lanes 5 and 6 contains samples from fractions 21 and 22, eluted at pH 4.0. Lane 7 contains a sample from fraction 22 reduced with DTT.

SDS-PAGE analysis of 10-ml samples of selected fractions showed a discrete band at 22–24 kDa under non-reducing conditions. Results are shown in FIG. 4, which shows a 22–24 kDa band for fractions 7 and 8 (lanes 3 and 4, respectively), and also for fractions 21 and 22 (lanes 5 and 6, respectively). In addition, higher molecular weight complexes of 46 and 69 kDa were also observed, which upon reduction with DTT resulted in a discrete band at 22–24 kDa (lane 7 of FIG. 4). The peaks at different pH elutions (pH 4.2 and 3.0) were pooled and dialyzed against decreasing concentrations of urea, and final dialysis was performed in PBS buffer (pH 7.4), at which time most of the proteins precipitated out of solution. Since non-refolded precipitated protein expressed from a similar system had shown biological activity in vivo, the exact procedure for "protein refolding" was done as described by O'Reilly et al. (1997) (*Cell* 88:277–285). The precipitated protein was used in suspension form for in vivo experiments only, with the concentration of protein measured by BCA assay (Pierce Chemical Co., Rockford, Ill., USA) (solubilized in urea with a suitable blank) and stored at −70° C. in small aliquots. Since mouse and human endostatin are conserved at the C-terminus, two small deletions were made. Primers were designed such that either 9 or 17 amino acids were deleted from the C-terminus of endostatin, resulting in two mutants, designated EM 1 and EM 2, respectively. For EM 1, all 4 of the cysteine residues were left intact. For EM 2, the most C-terminal cysteine was also deleted. The upstream primer for the EM 1 mutant was 5'-TTC CAT ATG CAT ACT CAT CAG GAC TTT CAG CCA-3' (SEQ ID NO: 8), and the downstream primer was 5'-TTA GCG GCC GCC TAC TCA ATG CAC AGG ACG ATG TA-3' (SEQ ID NO:9). The upstream primer for the EM 2 mutant was 5'-TTC CAT ATG CAT ACT CAT CAG GAC TTT CAG CCA-3' (SEQ ID NO:8), and the downstream primer was 5'-TTA GCG GCC GCC TAG TTG TGG CAG CTC GCA GCT TTC TG-3' (SEQ ID NO:10).

The amplified DNA fragments (528 bp for EM 1, 504 bp for EM 2) were purified, digested with NdeI and NotI, and ligated into a predigested pET28(a) expression vector. The rest of the protocol was carried out as described above. Induction conditions and processing of the bacterial pellet were as described by O'Reilly et al. (1997) (*Cell* 88:277–285). The purification of recombinant protein was performed using a Ni-NTA column in the presence of 8 M urea as described in the QIAexpressionist manual (Qiagen, Hilden, Germany). Briefly, the bacterial pellet was solubilized in equilibration buffer (8 M urea, 10 mM Tris and 100 mM sodium phosphate buffer, pH 8.0) for one hour at room temperature. The suspension was sonicated 3–4 times, centrifuged at 10,000× g and the soluble fraction was loaded on a Ni-NTA column pre-equilibrated with the above buffer at a flow rate of 10–20 ml per hour. The column was washed extensively with equilibration buffer. Bound proteins were eluted by lowering the pH of the buffer from 8.0 to 6.3, then to 4.2, and finally to 3.0. For the in vivo experiments utilizing endostatin mutants, non-specific proteins binding to the column were removed by an equilibration buffer wash, followed by 10 mM and 25 mM imidazole washes. Bound proteins were eluted in equilibration buffer containing 0.2 M acetic acid. The purified fractions were analyzed by SDS-PAGE and the fractions containing purified endostatin (pH 4.2 and 3.0 for wild type endostatin and equilibration buffer containing 0.2 M acetic acid for endostatin mutants) were pooled and refolded slowly. The final dialysis was carried out against PBS (pH 7.4) at 4° C. During dialysis the protein precipitated out of solution. It was further concentrated and stored at −70° C. in small aliquots. The concentration of protein was determined by the BCA assay (Pierce Chemical Co., Rockford, Ill., USA).

Example 3

Expression of Mouse Endostatin in *Pichia pastoris*

*Pichia pastoris*, a methanotropic yeast strain, has many advantages of a higher eukaryotic expression system: (a) the presence of alpha factor signal sequence facilitates secretion of the expressed protein into the medium, (b) the yeast strain (GS115) secretes only very low levels of endogenous host protein which further simplifies the purification process, (c) endotoxin contamination is not an issue, and (d) glycosylation can occur. The pPICZαA vector was selected for expression of mammalian endostatin and its mutants and fragments, because this system produces anti-angiogenic proteins in high titer, and with excellent biological activity, as is described in detail in PCT/US98/25892, "Methods of Producing Anti-Angiogenic Proteins: Endostatin, Angiostatin and Restin, Using a *Pichia* Yeast Expression System" by Vikas P. Sukhatme, filed Dec. 8, 1998, and in U.S. Ser. No. 09/589,483, "Methods of Producing Anti-Angiogenic Proteins", by Vikas P. Sukhatme, filed Jun. 7, 2000, the entire teachings of all of which are incorporated herein by reference. When this expression system was used, mammalian endostatin was found to be expressed as a soluble protein (20 kDa) with a peak level of expression noted on the second day after induction.

The sequence encoding mouse endostatin was further modified by amplification using Vent DNA polymerase on a template of pET17bhis construct, which contained the mouse endostatin described above. The upstream primer used was 5'-GGG AAT TCC ATA CTC ATC AGG ACT TT-3' (SEQ ID NO:1 I), and the downstream primer was 5'-AAG CGG CCG CCT ATT TGG AGA AAG AGG T-3' (SEQ ID NO:6). The amplified fragment containing EcORI and NotI restriction sites was subcloned into a predigested yeast expression vector. The pPICZαA vector carries an alpha factor secretion signal sequence with a Zeocin marker for antibiotic selection. Initial transformation was done in the Top 10' host strain (InVitrogen, San Diego, Calif., USA). The resultant clones were screened for the presence of an insert and positive clones were sequenced. The plasmid was then linearized with SacI and used for homologous recombination into the yeast host strain GS 115 (InVitrogen, San Diego, Calif., USA). The transformation was carried out by the lithium chloride method as described in the *Pichia* expression manual. Recombinants were selected by plating on YPD plates containing 100 μmg/ml of Zeocin. Clones which grew on YPD/Zeocin plate were tested for expression.

Initial screening was used to identify yeast clones with high levels of expression. The expression of mouse endostatin in large scale was carried out in 2-liter baffled shaker flasks. The overnight culture ($A_{600}$, 2–6) was used to inoculate 2-liter flasks, with addition of 500 ml of buffered glycerol medium. Cells were grown at 250 rpm at 30° C. until $A_{600}$, 16–20 (2 days). Subsequently, cells were centrifuged at 5000 rpm for 10 minutes, and the yeast resuspended in 300–400 ml of buffered methanol induction medium. The supernatant containing the secreted recombinant protein was harvested on the second, third, and fourth day after induction. After the final harvest, the cell free supernatant was processed immediately.

Example 4

Purification of Mouse Endostatin Via Heparin-Agarose Chromatography

A heparin-agarose column was used for purification, based on data of O'Reilly, et al. (1997) (*Cell* 88:277–285). The crude supernatant containing recombinant protein was concentrated by ammonium sulfate precipitation (70%). The precipitated protein was dissolved in 10 mM Tris buffer pH 7.4 containing 150 mM NaCl and dialyzed overnight at 4° C. with three changes at 6–8 hour intervals. The dialyzed sample was further concentrated by ultra-filtration using an Amicon concentrator (YM10). A disposable polyprep column (BiORad, Hercules, Calif., USA) was packed with heparin-agarose resin and equilibrated with 10 mM Tris, 150 mM NaCl, ph 7.4. The concentrated sample was loaded on the column at a flow rate of 20 ml/hour using a peristaltic pump. The column was washed with equilibration buffer until the $A_{280}$ was greater then 0.001. Bound proteins were eluted in 2-ml fractions by a step-wise gradient of NaCl at 0.3 M, 0.6 M, 1 M and 2 M NaCl). The peak fractions from 0.6 M to 1 M were pooled and dialyzed against PBS, pH 7.4.

Protein concentration was measured by the BCA assay (Pierce Chemical Co., Rockford, Ill., USA). The purification process was performed at 4° C. in a cold room. Recombinant soluble endostatin expressed from the *Pichia* system was used in all the in vitro assays.

Figure 5:
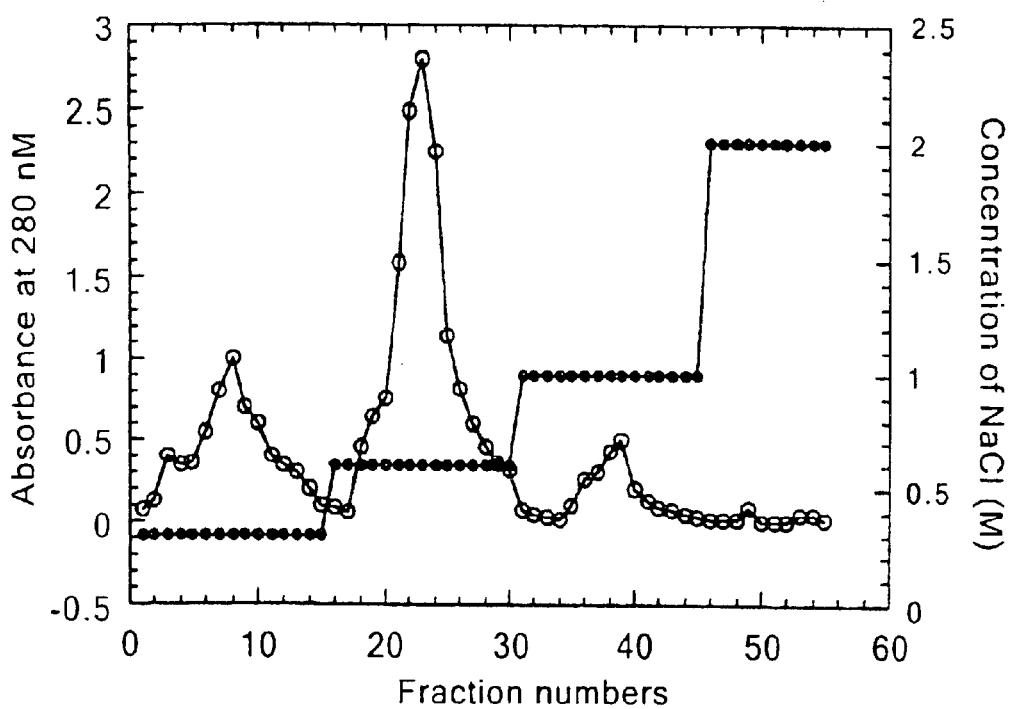
FIG. 5 is a graph showing the purification of soluble mouse endostatin expressed in yeast using a heparin-agarose column. The fraction number is shown along the x-axis, and the absorbance at 280 nm for each fraction (○) is on the left y-axis, and the concentration of NaCl used to elute each fraction (■) is shown on the right y-axis.
Figure 6:
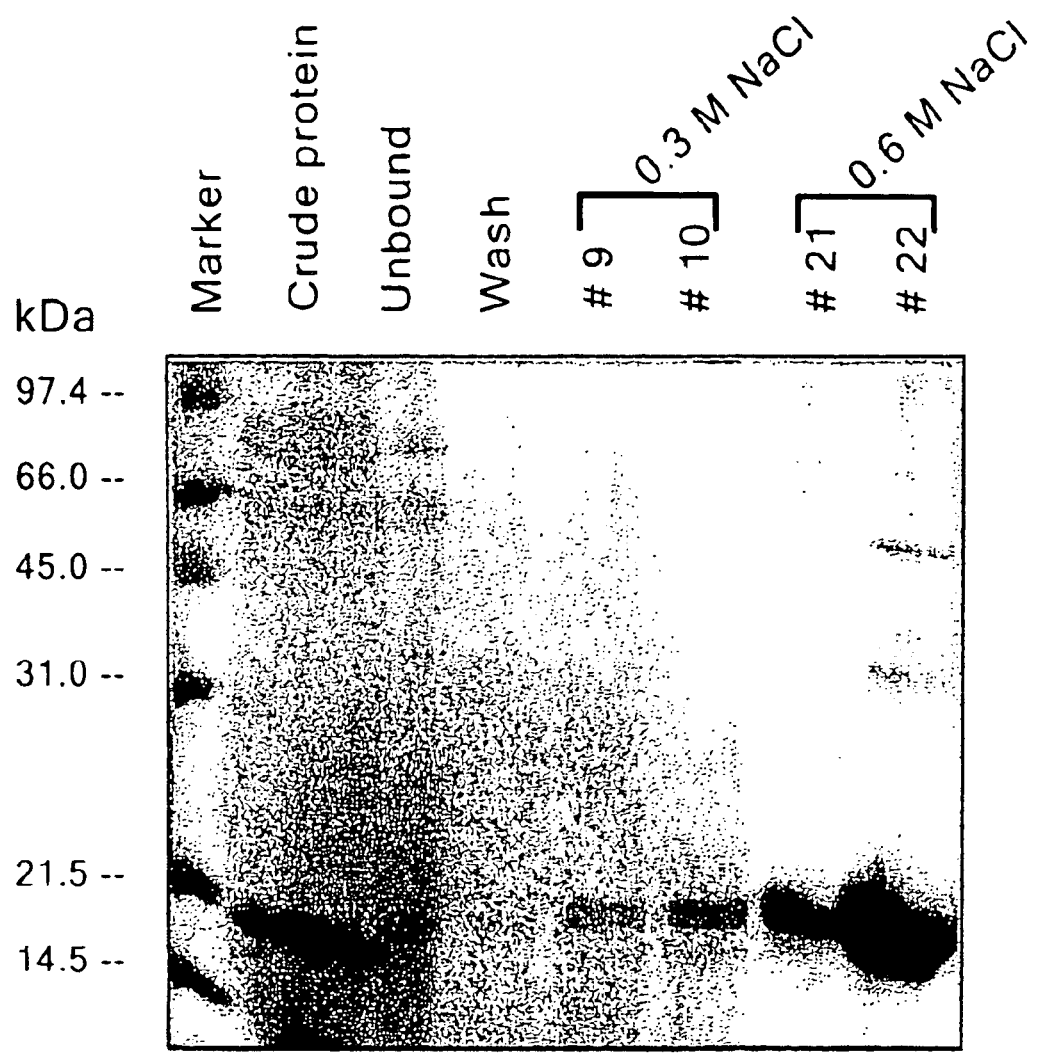
FIG. 6 shows a 12% non-reducing SDS-PAGE gel of purified recombinant soluble mouse endostatin from a heparin-agarose column. Sizes in kDa are shown on the left, and the first lane contains size markers. Lane 2 contains crude protein, lane 3 contains unbound protein, lane 4 contains wash, and lanes 5 and 6 contain samples from fractions 9 and 10, respectively, which were both eluted with 0.3 ml NaCl. Lanes 7 and 8 contain samples from fractions 21 and 22, respectively, which were both eluted with 0.6 M NaCl.

FIGS. 5 and 6 show the elution profile and SDS-PAGE analysis, respectively, of the purified protein. FIG. 5 shows the fraction number α-axis), plotted against the absorbance at 280 nm (○) (left y-axis) and against concentration of NaCl ( ) (right y-axis) used to elute the fraction. Two distinct peaks were obtained with increasing concentration of NaCl. The first peak at 0.3 M NaCl was small when compared to the major peak at 0.6 M NaCl. Most of the endostatin protein bound to the column as shown by the lack of the protein in the flow-through fraction (FIG. 6, lane 4). The recombinant protein bound tightly and washing with the low salt Tris buffer removed other yeast derived proteins. Protein eluted from the 0.3 M NaCl fraction had a trace amount of endostatin but was contaminated with other host derived high molecular weight protein. The purified protein migrated at 20 kDa which upon reduction migrated at 22 kDa. The protein fractions eluted at 0.6 M and 1 M NaCl were pooled, concentrated and dialyzed against PBS (pH 7.4). The purified protein was further separated by FPLC using a Superose 12 (Pharmacia Biotech, Inc., Piscataway, N.J., USA) size separation column. The elution profile from this column showed a single peak. Aliquots of 10 ml from selected fractions were analyzed on a 12% SDS-PAGE gel, and the results are shown in FIG. 6. SDS-PAGE analysis showed the presence of single discrete band of 22–24 kDa corresponding to endostatin. The level of expression was estimated to be in the range of 15–20 mg per liter of culture.

To further characterize the recombinant protein, N-terminal microsequencing was carried out for seven cycles. It showed that the yeast alpha factor signal peptide was processed and cleaved at alanine. The first seven residues (EFHTHQD) of the purified protein after signal peptide cleavage matched exactly the published sequence of endostatin protein, with the first two residues (EF) derived from linker sequence.

Example 5

Cloning and Expression of His.endostatin into the *Pichia* Expression System

The coding region of the mouse endostatin construct in the pET17bhis expression vector is preceded by a His.Tag of 10 histidine residues. The coding region, including the His.Tag sequence, was shuttled into pPICZαA vector via amplification with EcORI and NotI sites. Linearization and recombination into the yeast host strain GS 115 were done as described above. The cell-free medium was precipitated with 70% ammonium sulfate. Precipitated proteins were dissolved in 50 mM sodium phosphate buffer (pH 8.0) containing 300 mM NaCl and dialyzed in the same buffer at 4° C. with three changes at 6–8 hour intervals. A Ni-NTA column was used for purification of the His.endostatin recombinant protein, as described in the QLAexpressionist manual (Qiagen, Hilden, Germany). Bound proteins were eluted with a step-wise gradient of imidazole (10 mM, 25 mM, 50 mM, and 100 mM). The peak fractions from 50 mM and 100 mM imidazole elutions were pooled and dialyzed against PBS buffer, pH 7.4.

Figure 7:
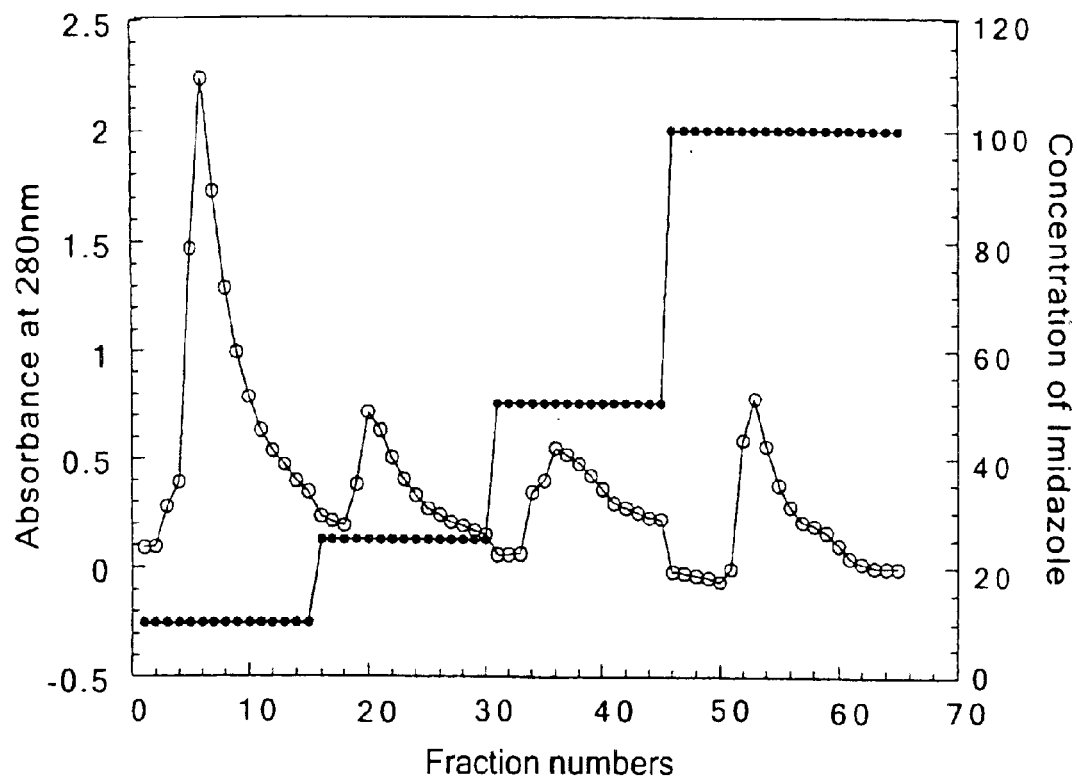
FIG. 7 is a graph showing the elution profile of soluble His.endostatin expressed in yeast using a Ni-NTA column. The fraction number is shown along the x-axis, and the absorbance at 280 nm for each fraction (○) is on the left y-axis, and the concentration of imidazole (mM) used to elute each fraction (■) is shown on the right y-axis.
Figure 8:
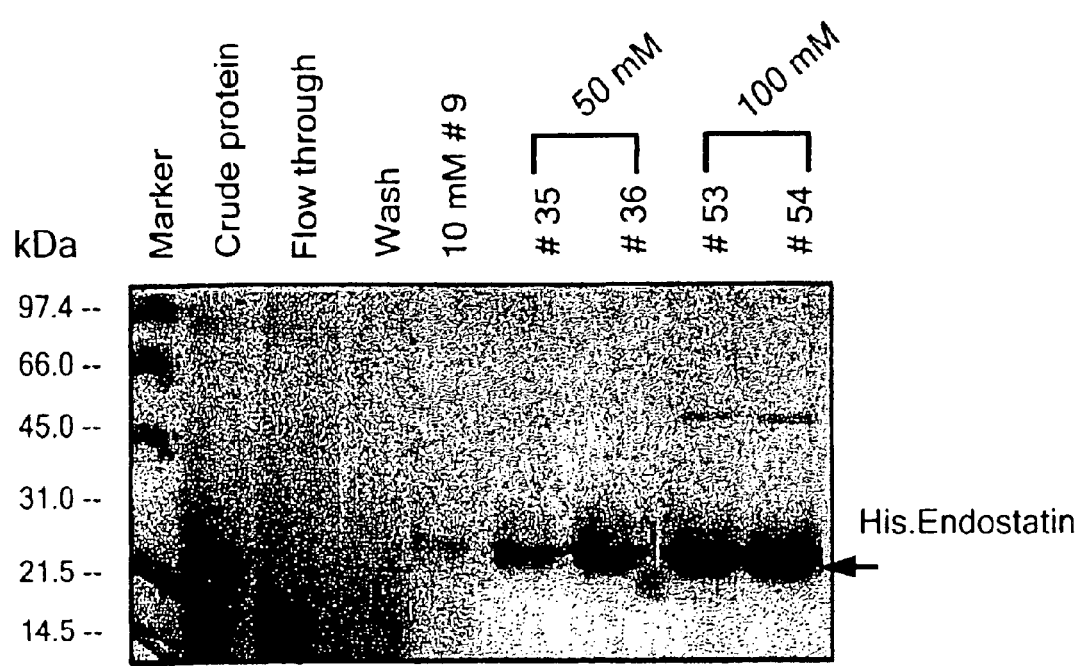
FIG. 8 shows a 12% non-reducing SDS-PAGE gel of selected fractions of soluble His.endostatin expressed in yeast. Sizes in kDa are shown on the left, and the first lane contains size markers. Lane 2 contains crude protein, lane 3 contains flowthrough (i.e., unbound protein), and lane 4 contains wash. Lane 5 contains a sample of fraction 9, which was eluted at 10 mM imidazole. Lanes 6 and 7 contain samples from fractions 35 and 36, respectively, which were eluted with 50 mM imidazole, and lanes 8 and 9 contains samples of fractions 53 and 54, respectively, which were eluted with 100 mM imidazole.

The results are shown in FIGS. 7 and 8. FIG. 7 shows the fraction number (x-axis), plotted against the absorbance at 280 nm (○) (left y-axis) and against concentration of imidazole (●) (right y-axis) used to elute the fraction. Several absorbance peacks were observed, the first being the largest, followed by three smaller peaks. The elution profile of His.endostatin from the Ni-NTA column showed that the recombinant protein bound tightly. The yeast-derived host proteins in the culture supernatant did not bind to the column and were removed during the wash. Bound proteins were eluted by a stepwise gradient of imidazole. The non-specifically bound host derived proteins eluted with the addition of 10 mM imdiazole (FIG. 7). At 25 mM imidazole, a small fraction of the recombinant protein was eluted along with proteins of higher molecular weight. Final elution with 50 mM and 100 mM imidazole showed a distinct peak. SDS-PAGE analysis is shown in FIG. 8. The flow-through fraction (lane 3) did not contain any endostatin, indicating that most of the protein bound to the column. Increasing the concentration of imidazole to 10 mM and 25 mM resulted in the elution of non-specific protein. Purified recombinant His.endostatin migrated as a single band corresponding to 22–24 kDa in 50 mM imidazole. A protein with a molecular weight of 22 kDa was seen at 100 mM along with a smaller amount of protein corresponding to 44–46 kDa. The concentration of purified protein was determined by the BCA method. The level of expression was estimated at 15 mg per liter of culture.

Example 6

Characterization of Recombinant Yeast Endostatin and Polyclonal Antibody Generation and Western Blot Analysis Polyclonal antiserum to mouse recombinant endostatin produced in yeast was raised by immunizing a rabbit with 10 μg of purified protein derived from the *Pichia* expression system. Recombinant endostatin expressed from bacteria and yeast system were separated on a 12% SDS-PAGE gel. The proteins were transferred to PVDF membrane by semi-dry transfer (Trans-blot, BiORad, Hercules, Calif., USA). The primary antiserum was diluted to 1:4000 in 1×TBS buffer containing 5% non-fat dry milk. Goat anti-rabbit IgG/HRP conjugate was used as a secondary antibody (1:5000). Immunoreactivity was detected by chemiluminescence (Pierce Chemical Co., Rockford, Ill., USA).

Figure 9:
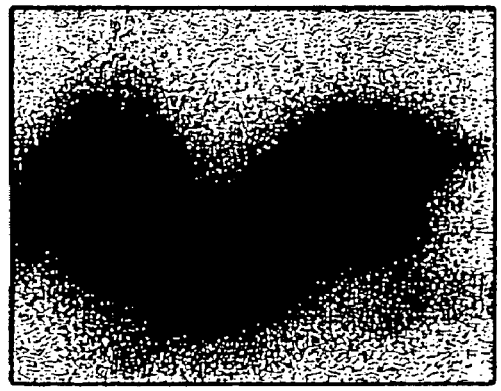
FIG. 9 shows a Western blot analysis of recombinant mouse endostatin expressed from bacteria and yeast. Lane 1 contains bacterially-expressed His.endostatin, lane 2 contains endostatin expressed in yeast, and lane 3 contains yeast-produced His.endostatin.

The purified endostatin expressed from the bacterial and yeast expression systems were run under reducing and non-reducing conditions. FIG. 9 shows immunoreactive bands corresponding to endostatin. The size of the protein estimated from the western blot ranges from 22–24 kDa. In addition, the recombinant His.endostatin from yeast and bacteria was probed with a Penta His.monoclonal antibody (Qiagen, Hilden, Germany). The monoclonal antibody showed positive response only with the His.endostatin whereas native endostatin did not show any immunoreactivity. This data confirmed the presence of the His.Tag in the recombinant protein. The antiserum did not show any cross reactivity to human or mouse angiostatin, demonstrating some degree of immunoreactivity specific to endostatin. Immunoreactivity of the polyclonal antibody was also observed with EM 1 and EM 2 proteins.

Example 7

Endothelial Proliferation Assay

The anti-proliferative effect of endostatin produced in the yeast system was tested using bovine pulmonary artery endothelial cells (C-PAE). Initial experiments were done with different endothelial cell types and various parameters (time of "starvation," serum concentration, concentration and type of mitogenic stimulus (e.g., VEGF vs. bFGF)). C-PAE cells gave the most reproducible response.

C-PAE cells were plated in 24-well plates coated with fibronectin (10 µg/ml) at 12,500 cells per well in 0.5 ml DMEM containing 2% FBS. After a 24-hour incubation at 37° C., the medium was replaced with fresh DMEM and 2% FBS containing 3 ng/ml of bFGF (R & D systems, Minneapolis, Minn., USA) with or without recombinant mouse endostatin. The cells were pulsed with 1 µCi of $^3$H-thymidine for 24 hours. Medium was aspirated, cells were washed three times with PBS, and then solubilized by addition of 1.5 N NaOH (100 µl per well) and incubated at 37° C. for 30 minutes. Cell-associated radioactivity was determined with a liquid scintillation counter. The experiment was repeated 5 times under identical conditions, with similar results each time.

Figure 10:
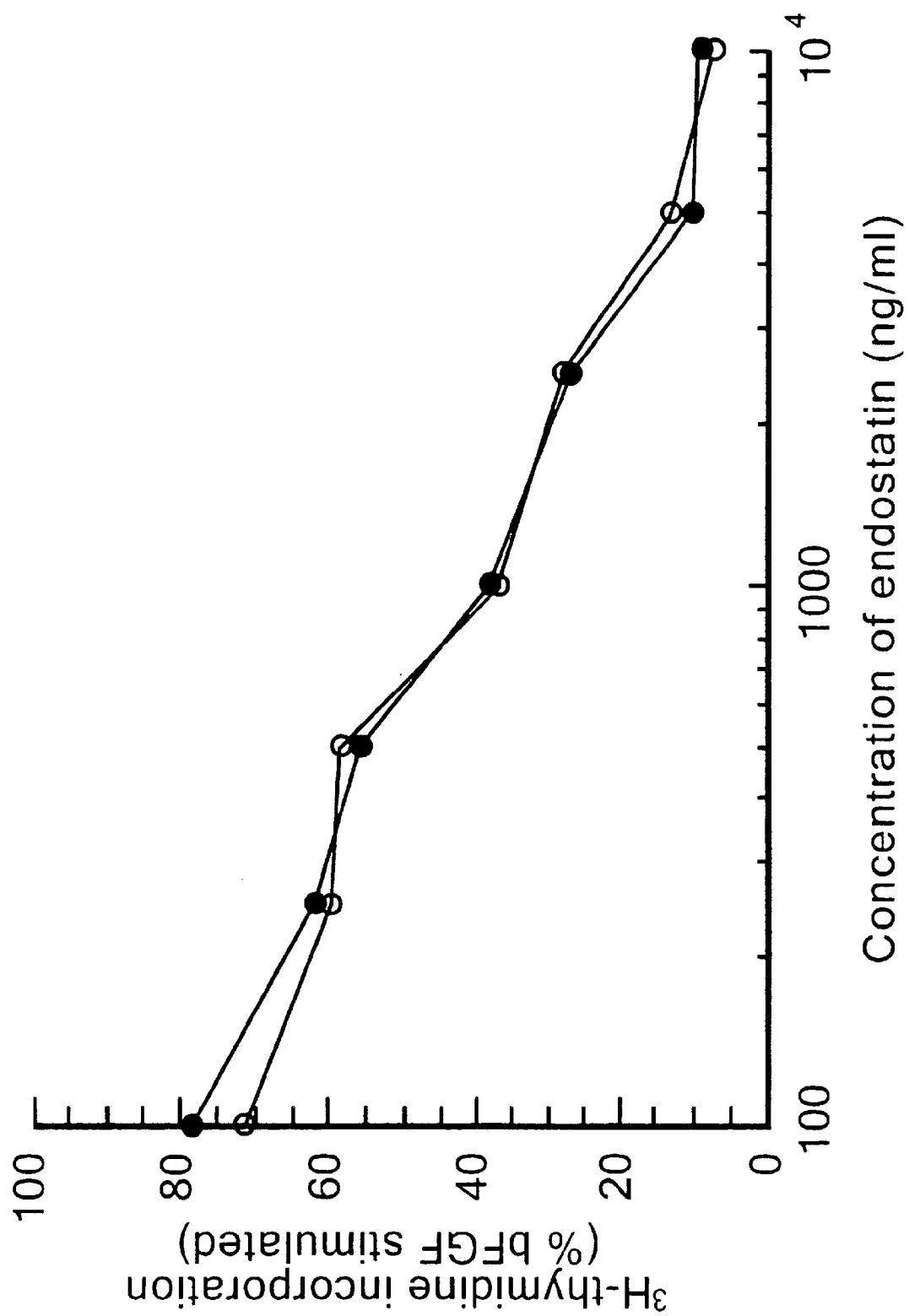
FIG. 10 is a graph depicting the results of an endothelial cell proliferation assay. The purified mouse endostatin expressed from yeast was tested for its ability to inhibit (methyl-$^3$H) thymidine incorporation in C-PAE cells. The concentration of endostatin (100 ng to 1000 ng) is shown on the x-axis, and the incorporation of $^3$H-thymidine is shown on the y-axis. Incorporation for yeast-derived soluble endostatin (○) and yeast-derived soluble His.endostatin (■) dropped steadily with increasing concentration of endostatin.

A dose dependent inhibition of bFGF induced proliferation was observed. The results are shown in FIG. 10, which is a graph showing concentration of yeast-derived soluble endostatin (○) and yeast-derived soluble His.endostatin (●) along the x-axis, and incorporation of $^3$H-thymidine on the y-axis. In general, incorporation decreased steadily with increasing concentration of endostatin. The inhibition range (30–94% of control) was seen with increasing concentrations of endostatin (0.1 µg/ml to 10 µg/ml), with an $ED_{50}$ value in the range of 600–700 ng/ml. A similar inhibitory effect on C-PAE cells was seen when His.endostatin from yeast was tested in the above assay, as is shown in the graph in FIG. 10. Incorporation of $^3$H-thymidine dropped steadily with increasing concentration of either yeast-derived soluble endostatin (○) and yeast-derived soluble His.endostatin (●).

Figure 11:
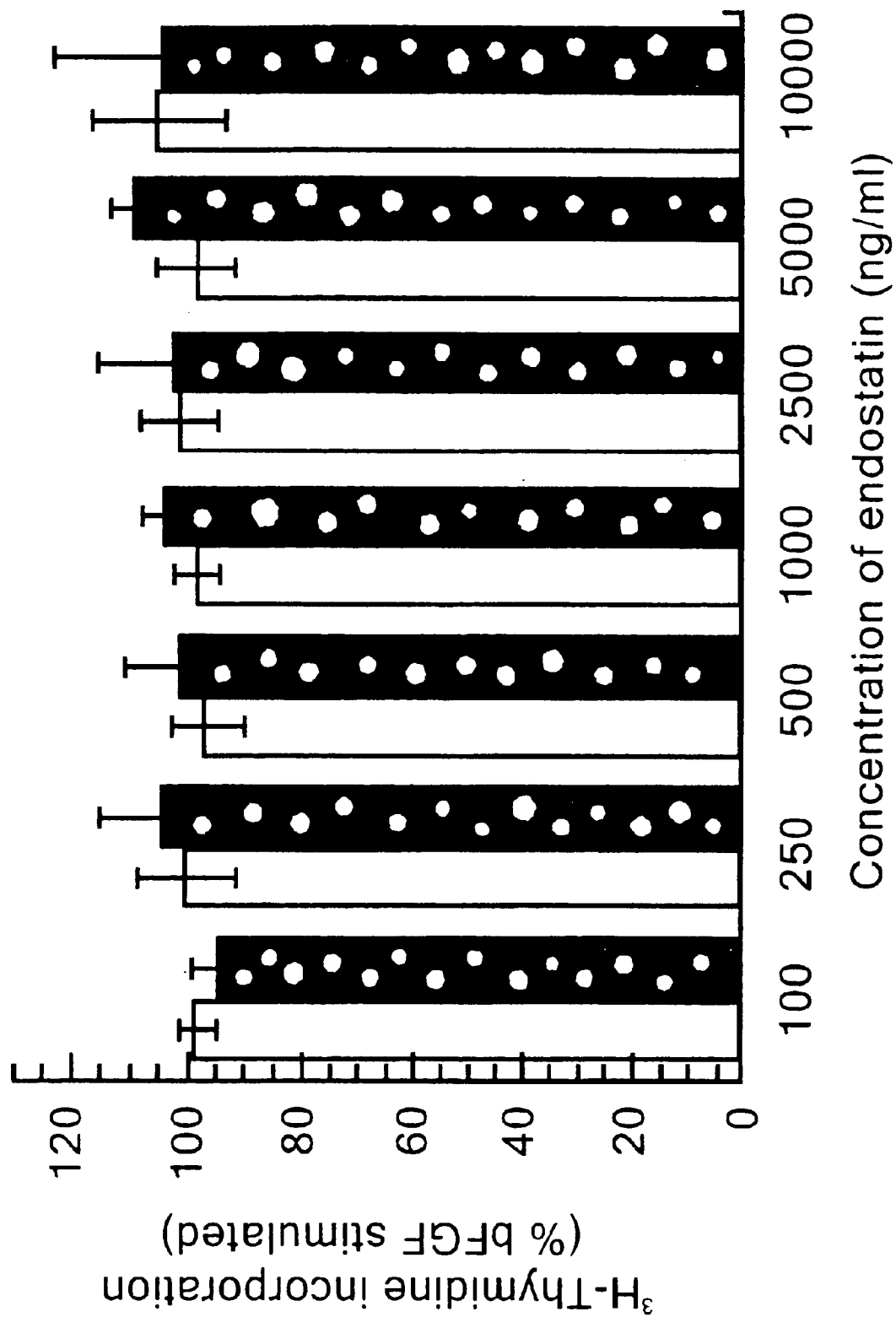
FIG. 11 is a bar chart showing the effects of recombinant mouse endostatin on non-endothelial cells. Open bars refer to 786–0 cells, and shaded bars refer to $A_{498}$ cells. Both are renal carcinoma cell lines, stimulated with bFGF (3 ng/ml) in 2% serum.

The recombinant protein did not inhibit the proliferation of the renal cell carcinoma cells (786-0 and A498) at concentrations ranging from 0.5 µg/ml to 10 µg/ml, as shown in FIG. 11. FIG. 11 is a bar chart, showing the incorporation of $^3$H-thymidine in 786–0 cells (open bars), and A498 cells (shaded bars). The recombinant endostatin also did not have an effect on IMR90 and NIH3T3 fibroblasts.

Example 8

Endothelial Cell Migration Assay

Since C-PAE cells do not migrate in response to bFGF and VEGF, ECV304 cells were used with different concentrations of endostatin using bFGF as a stimulus. To determine the ability of recombinant endostatin to block migration of ECV304 cells towards bFGF, a migration assay was performed using 12-well Boyden chemotaxis chambers (Neuro-Probe, Inc., Cabin John, Md., USA) with a polycarbonate membrane (25×80 mm PVD free, 8µ pores, Poretics Corp., Livermore, Calif., USA). The non-specific binding of growth factor to the chambers was prevented by coating the chambers with a solution containing 0.5% gelatin, 1 mM $CaCl_2$ and 150 mM NaCl at 37° C. overnight. ECV304 cells were grown in 10% FBS containing 5 ng/ml DiI (1,1'-dioctadecyl-3,3,3',3'-tetramethylindocarbocyanine perchlorate DiIC18, Molecular Probes, Eugene, Oreg., USA) overnight and washed with PBS containing 0.5% BSA. Following trypsinization, the cells were counted using Coulter-Counter Z1, (Luton, U.K.) and diluted to 300,000 cells/ml in Medium 199 (Life Technologies, Gibco/BRL, Gaithersburg, Md., USA) containing 0.5% FBS. The lower chamber was filled with Medium 199 containing 25 ng/ml bFGF. The upper chamber was seeded with 15,000 cells/well with different concentrations of recombinant endostatin. Cells were allowed to migrate for 4 hours at 37° C. At that time, the cells on the upper surface of the membrane were removed with a cell scraper and the (migrated) cells on the lower surface were fixed in 3% formaldehyde and washed in PBS. Images of the fixed membrane were obtained using fluorescence microscopy at 550 nM with a digital camera and the number of cells on each membrane was determined using the OPTIMAS (version 6.0) software (Media Cybernetics, L.P., Silver Spring, Md., USA).

Figure 12A:
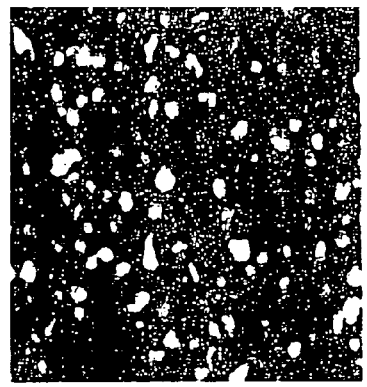
FIGS. 12A and 12B are a pair of photographs showing inhibition of endothelial cell (ECV304) migration by soluble mouse endostatin using bFGF (25 ng/ml) as a stimulus.
Figure 12B:
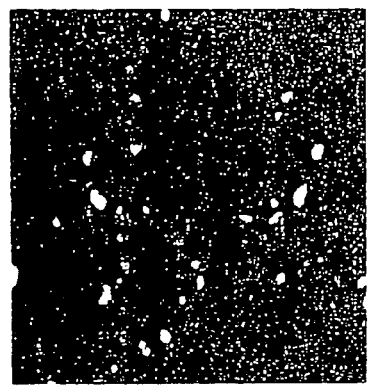
Figure 13:
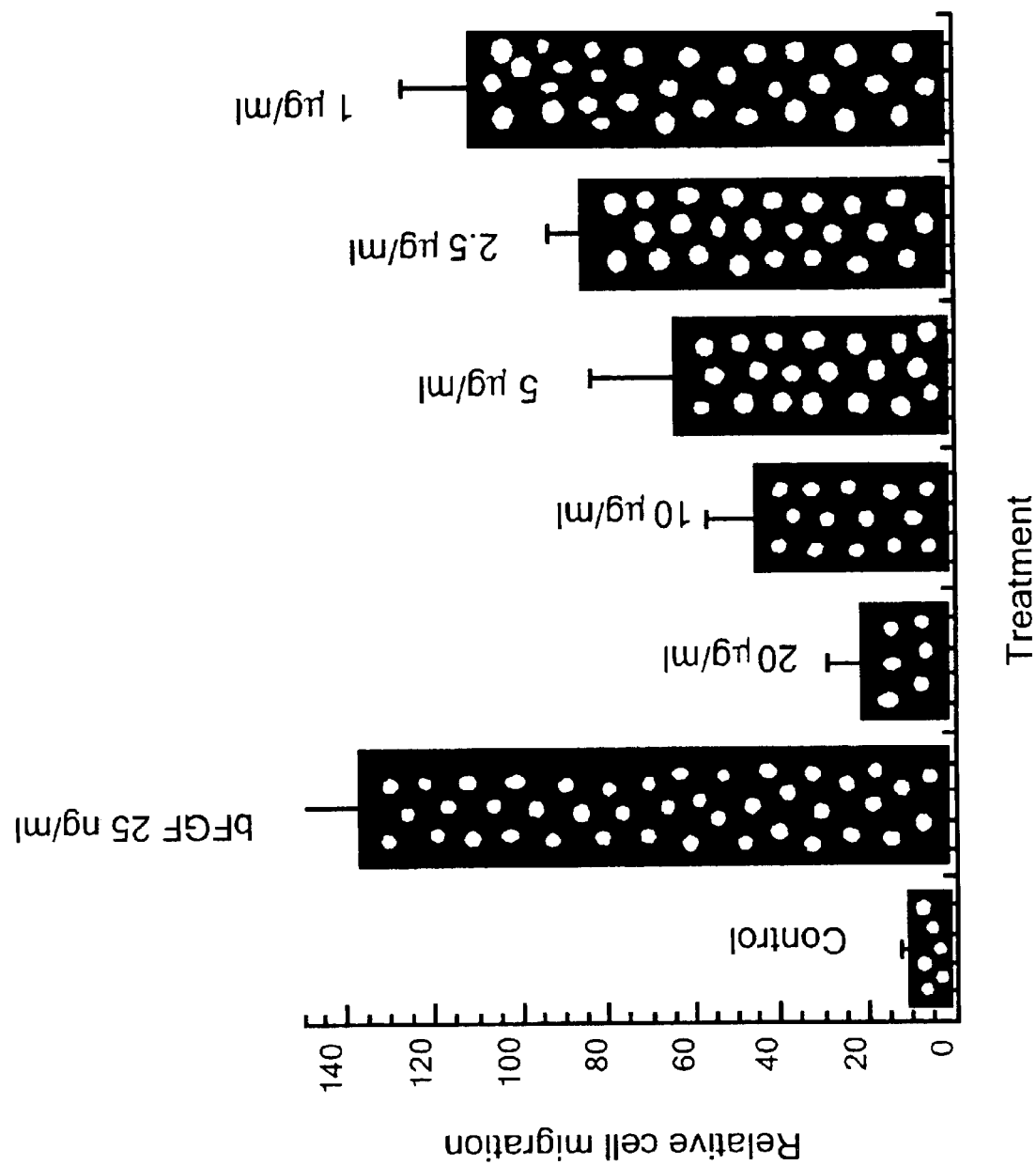
FIG. 13 is a bar chart showing inhibition of endothelial cell migration with different concentrations of endostatin. Relative cell migration is shown on the y-axis, and treatment (control, 25 ng/ml bFGF, and endostatin at 20, 10, 5, 2.5, and 1 μg/ml) on the x-axis.

Addition of endostatin resulted in a dose-dependent inhibition of migration, as shown in FIGS. 12A and 12B, and FIG. 13. FIGS. 12A and 12B are photomicrographs showing inhibition of endothelial cell (ECV304) migration by soluble mouse endostatin using bFGF (25 ng/ml) as a stimulus. FIG. 12A shows migrated endothelial cells in the control (+bFGF, no endostatin), and FIG. 12B shows migrated endothelial cells treated with endostatin (20 µg/ml) with bFGF.

FIG. 13 is a bar chart showing inhibition of endothelial cell migration with different concentrations of endostatin. Relative cell migration is shown on the y-axis, and treatment (control, 25 ng/ml bFGF, and endostatin at 20, 10, 5, 2.5, and 1 µg/ml) on the x-axis. Each treatment was done in duplicate. In each well, the number of cells migrated was counted in three different areas and the average obtained. Each value is a mean from representative experiments and error bars represent standard deviations. At a concentration less than 1 µg/ml, marginal inhibition of migration was noted, whereas at 10 µg/ml, 60% inhibition of endothelial cell migration was observed. These studies are the first to show endostatin's effect on cell migration. Endostatin's action on migration of two non-endothelial cell lines was also assessed. No effect was seen on inner medulary collecting duct renal cells (IMCD), and some effect (15% at 5 µg/ml and 50% at 20 µg/ml) was noted in the IC-21 macrophage precursor cell line, suggesting that at high concentration, endostatin may block cell migration in some cell types.

Example 9

Chorioallantoic Membrane (CAM) Assay

The ability of mouse endostatin to block bFGF induced angiogenesis in vivo was tested using the chorioallantoic membrane (CAM) assay. Fertilized white Leghorn chicken eggs (SPAFAS, Inc., Norwich Conn., USA) were opened on 100 mm$^2$ petri dishes and allowed to grow until day 11 in a humidified incubator at 38° C. Pellets containing vitrogen (Collagen Biomaterials, Palo Alto, Calif., USA) at a concentration of 0.73 mg/ml were supplemented with either: vehicle alone; VEGF (250 ng/pellet), VEGF (250 ng/pellet) and endostatin (20 to 0.5 µg/pellet), bFGF (50 ng/pellet), or bFGF (50 ng/pellet) and endostatin (20 to 0.5 µg/pellet). The pellets were allowed to polymerize at 37° C. for 2 hours. The pellets were placed on a nylon mesh and oriented on the periphery of the CAM. Embryos were returned to the incubator for 24 hours. Invasion of new capillaries on the collagen mesh was assessed by injection of FC-dextran into the circulation of the chicken embryo. At the end of the experiment, the meshes were dissected and evaluation of vascular density was done using the program NIH Image v 1.59 according to the method of Iruela-Arispe et al (1997) (*Thromb. Haemost.* 78:672–677). Assays were performed in triplicate and four independent experiments were conducted.

Figure 14A:
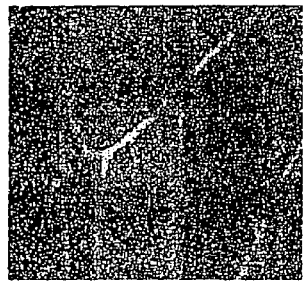
FIGS. 14A, 14B, and 14C are photomicrographs showing the inhibition of angiogenic response mediated by VEGF (250 ng/pellet) in the presence of endostatin.
Figure 14B:
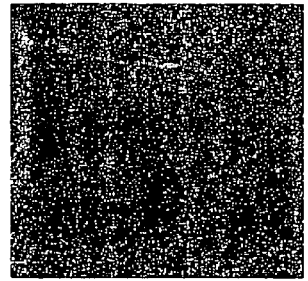
Figure 14C:
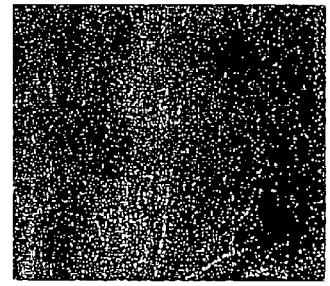
Figure 15A:
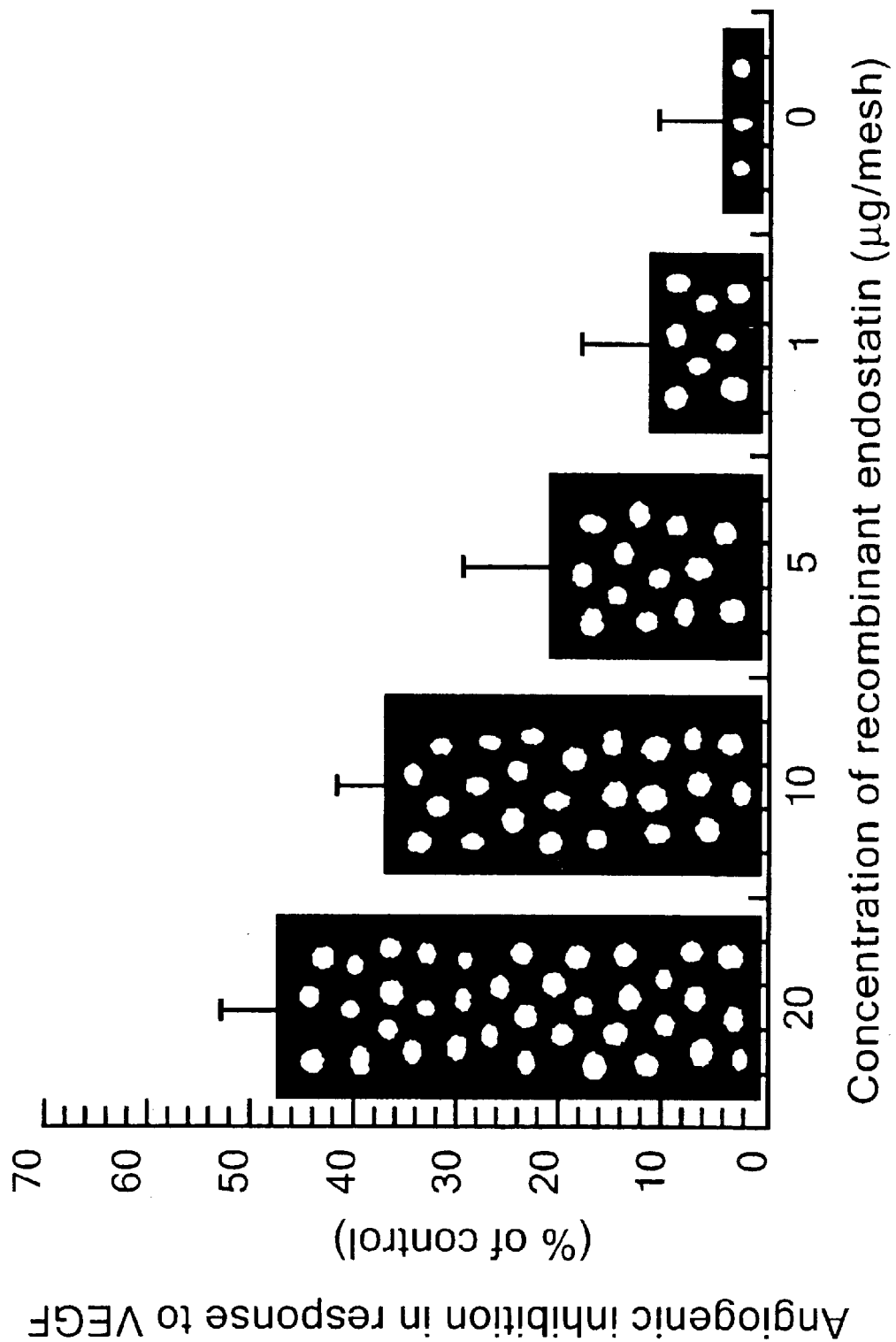
FIGS. 15A and 15B are a pair of bar charts showing the inhibition of VEGF (top panel) and bFGF (bottom panel) mediated angiogenic response by endostatin (20, 10, 5, 1, and 0 μg/mesh) in the CAM assay. Both charts show a steady increase of inhibition of angiogenesis in response to increasing concentrations of endostatin.
Figure 15B:
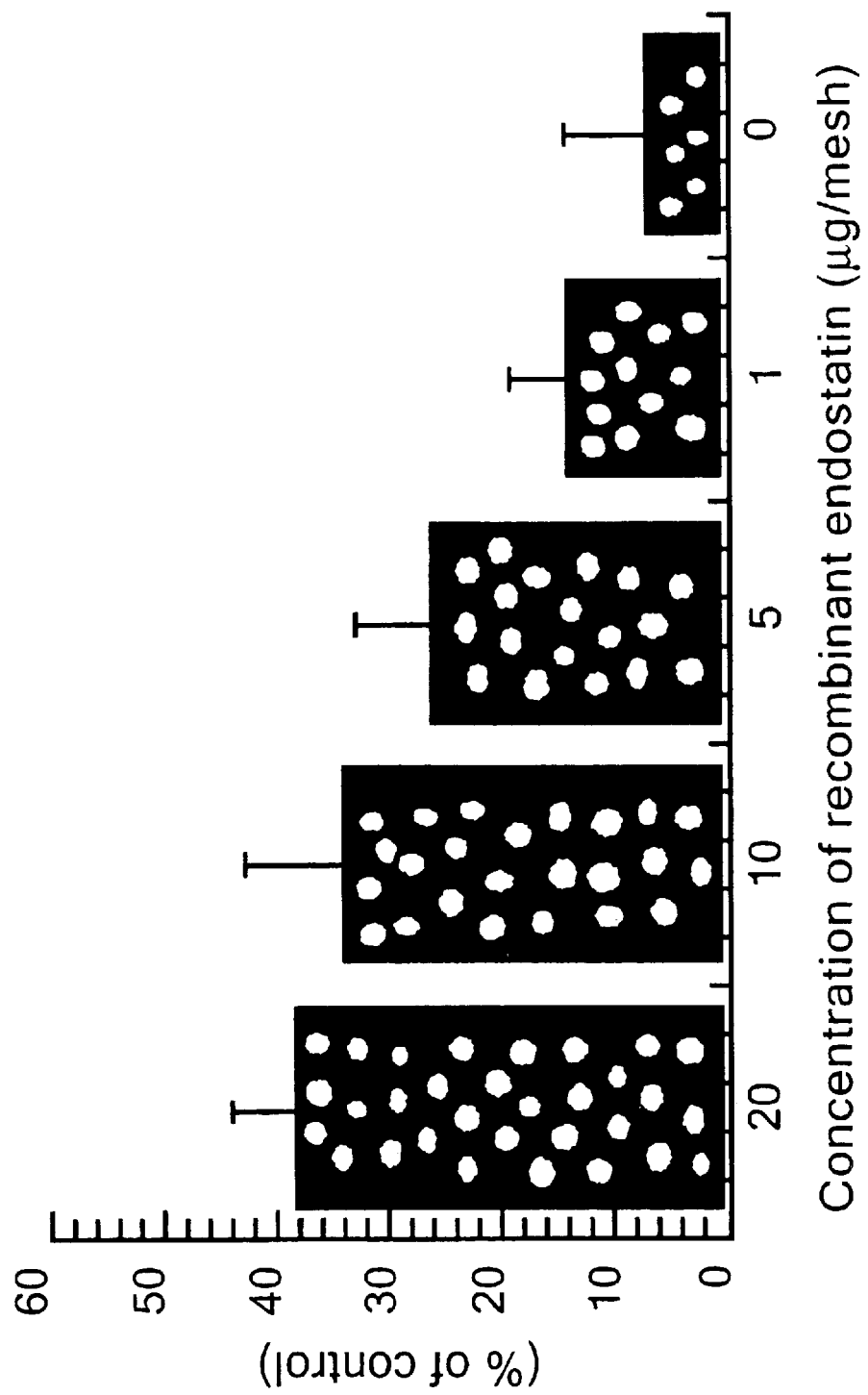

Endostatin was able to suppress the angiogenic response mediated by both bFGF and VEGF, as shown in FIGS. 14 and 15. FIG. 14 is a set of three photomicrographs showing the vascular density for vehicle alone (FIG. 14A), VEGF alone (250 ng/pellet, FIG. 14B), and VEGF and endostatin (FIG. 14C). FIGS. 15A and 15B show that the inhibition was dose-dependent. FIG. 15A is a bar chart showing concentration of recombinant protein α-axis), plotted against angiogenic inhibition in response to VEGF (y-axis). FIG. 15B is a bar chart showing concentration of recombinant protein α-axis), plotted against angiogenic inhibition in response to bFGF (y-axis). All of the counts were normalized to the negative control. Both charts show a steady increase of inhibition of angiogenesis in response to increasing concentrations of endostatin. Blocking of the VEGF response was somewhat more effective (47%) than suppression of the bFGF response (39%), both at 20 μg/mesh.

Example 10

Neutralization of Endostatin's Inhibitory Effect

The specificity of endostatin's inhibitory effect was demonstrated by neutralization studies using endothelial proliferation and CAM assays. In the endothelial proliferation assay, the endostatin was pre-incubated with an excess of polyclonal antiserum or purified antibody (IgG) for 1 hour at room temperature and then added to the C-PAE cells in the presence of 3 μg/ml bFGF. Pre-immune serum was used as negative control. In addition, purified IgG and endostatin antibody alone were also used as a control. DNA synthesis was measured by adding 1 μCi/well $^3$H-thymidine for 24 hours and the cell-associated radioactivity was measured as described above. For the CAM assay, endostatin (10 μg) and antiserum (50 μg) were pre-incubated overnight end-over-end at 4° C. prior to preparation of the pellets. Controls for these experiments included IgG alone and pre-immune serum alone. Evaluation of the angiogenic responses in the two assays were determined as indicated above.

Figure 16:
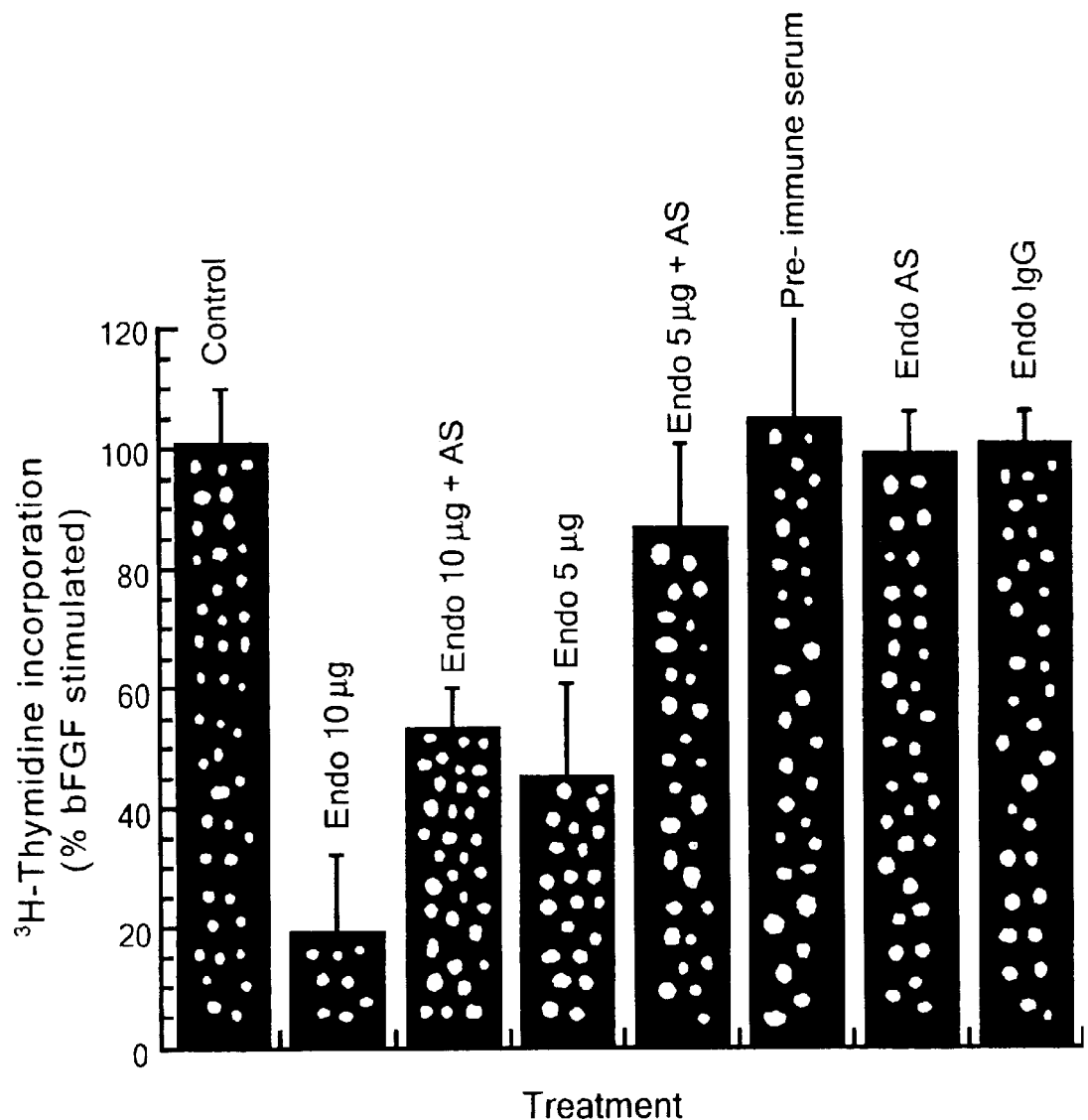
FIG. 16 is a bar chart showing neutralization of the inhibitory effect of mouse endostatin by polyclonal antiserum in the endothelial proliferation assay. Incorporation of $^3$H-thymidine is shown on the y-axis, and treatment (control, 10 μg endostatin, 10 μg endostatin+antiserum, 5 μg endostatin, 5 μg endostatin+antiserum, pre-immune serum, endostatin antiserum, and endostatin IgG) on the x-axis).
Figure 17A:
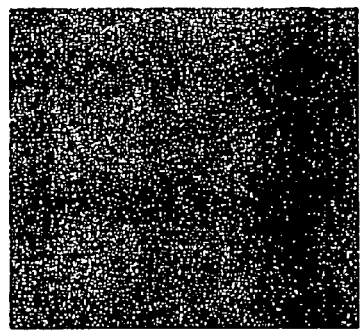
FIGS. 17A and 17B are a pair of photographs showing the results of a CAM assay, demonstrating neutralization of endostatin inhibitory activity by polyclonal antiserum.
Figure 17B:
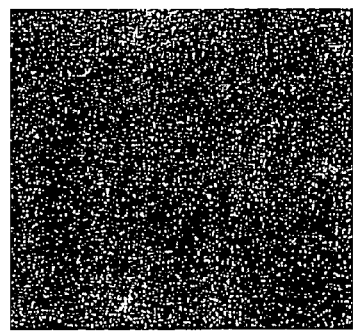

FIG. 16 is a bar chart showing neutralization of the inhibitory effect of mouse endostatin by polyclonal antiserum in the endothelial proliferation assay. Incorporation of $^3$H-thymidine is shown on the y-axis, and treatment (control, 10 μg endostatin, 10 μg endostatin+antiserum, 5 fig endostatin, 5 μg endostatin+antiserum, pre-immune serum, endostatin antiserum, and endoatatin IgG) on the x-axis). Each value is a mean from triplicate culture and error bars represent standard deviation. FIG. 17 is a pair of photomicrographs showing the results of the CAM assay. FIG. 17A shows the effect of VEGF and endostatin (10 μg), and FIG. 17B shows the effect of VEGF, endostatin (10 jig), and polyclonal antiserum (50 μg). Both FIG. 16 and FIG. 17 demonstrate that the inhibitory effect of endostatin can be suppressed by incubation with specific antiserum. Anti-endostatin antiserum blocked the suppressive effect by 95%. The pre-immune serum and endostatin antibody alone did not have a stimulatory effect, nor did normal rabbit IgG.

Example 11

Inhibition of Primary 786-0 RCC Tumors in Nude Mouse Model

Male nude mice of 6–8 weeks of age were injected subcutaneously in the right flank with 2 million 786–0 cells in a 100 ml volume. Tumors appeared approximately two weeks after implantation. Tumor size was measured using calipers and tumor volume was calculated using the standard formula of:

tumor volume=$ab^2$×0.52 where a=length of the tumor, and b=width of the tumor (O'Reilly et al. (1994) Cell 79:315–328). The tumor volume ranged from 350 mm$^3$ to 400 mm$^3$. The animals were randomized and each group had five mice with comparable tumor size within and among the groups. Treatment was started with recombinant endostatin (bacterial or yeast versions) with each mouse receiving 10 mg/kg body weight of recombinant protein daily, administered for a period of ten days via intraperitoneal injection. Control animals received PBS each day. Tumor size in all groups was measured on alternate days and tumor volume was calculated. The treatment was terminated on day 10 and animals were sacrificed and tumors from each mouse removed and fixed in 10% buffered formalin.

Figure 18:
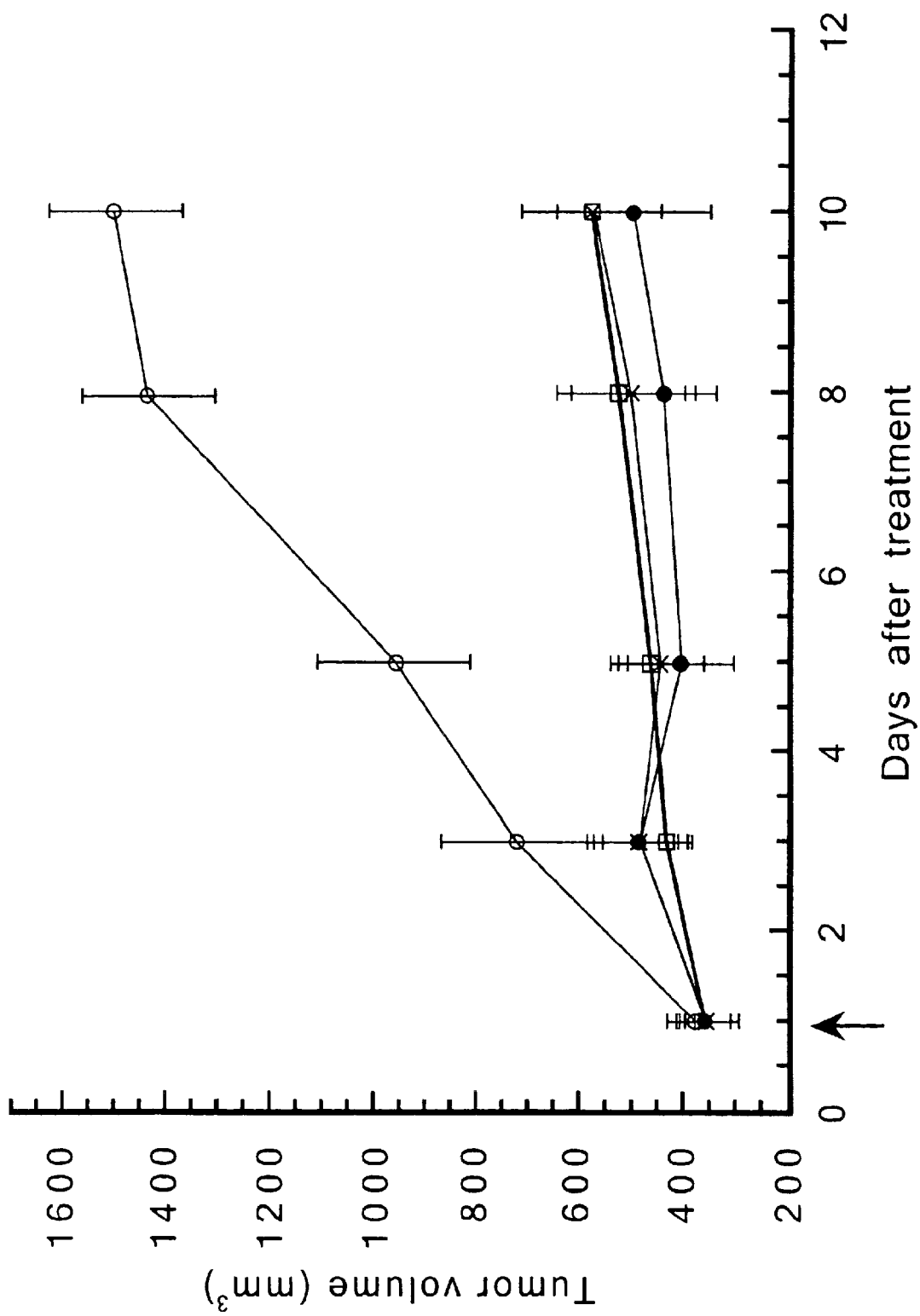
FIG. 18 is a graph showing the inhibition of 786-0 tumor growth by systemic treatment with recombinant endostatin. Time in days after treatment is shown on the x-axis and tumor volume in mm$^3$ is shown on the y-axis. Intraperitoneal injection of endostatin was given at 10 mg/kg/day, starting on day 1 (arrow). Each time point represents the average of five mice in each group and the error bar represents S.E.M. Treatments are control PBS (○), endostatin from yeast (●), His.endostatin from yeast (x) and His.endostatin from bacteria (□).
Figure 19A:
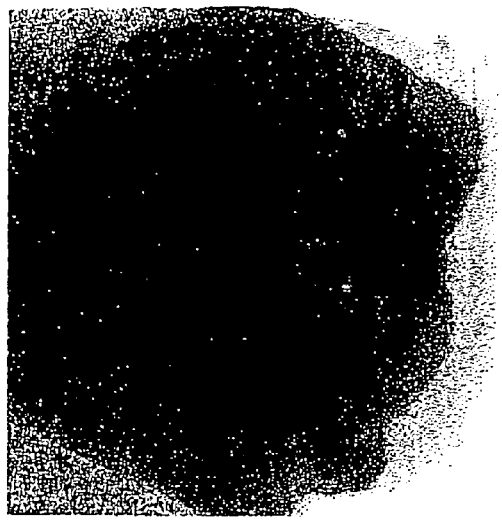
FIGS. 19A through 19E are a set of photographs of 786-0 tumors treated with recombinant endostatin. At the end of the treatment period, tumors from control and treated groups were examined grossly under a dissecting microscope.
Figure 19B:
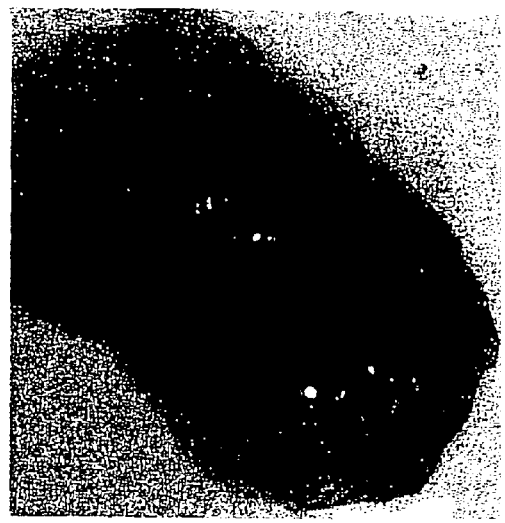
Figure 19C:
Figure 19D:
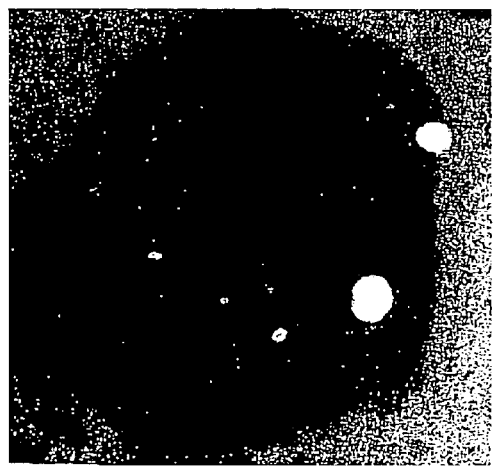
Figure 19E:
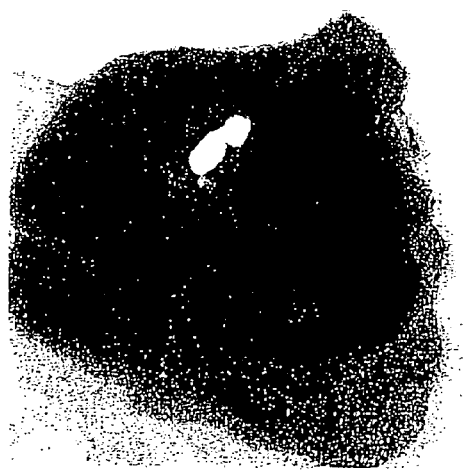
Figure 20:
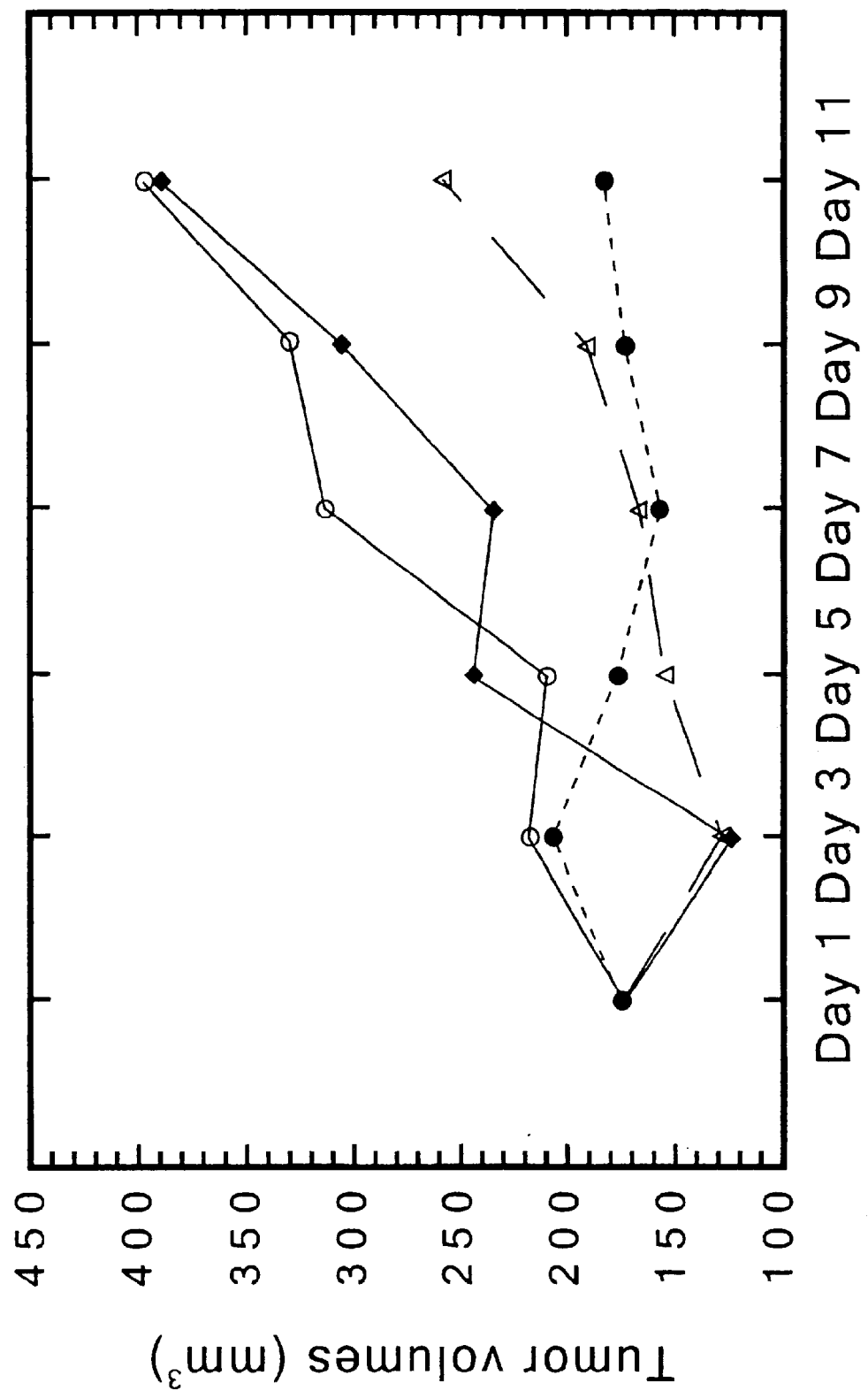
FIG. 20 is a graph showing the effects of endostatin mutants on athymic nude mice 786-0 tumors. Days after treatment is shown on the x-axis, and tumor volume on the y-axis. Each time point represents the average of five mice in each group. Treatments were control PBS (○), wild type His.endostatin from bacteria (dotted line, □), EM 1 from bacteria (Δ), and EM 2 from bacteria (solid line, ♦). EM 1 and EM 2 both contain N-terminus His.tags. Intraperitoneal injection was started on day 1 (arrow).

The results are shown in FIGS. 18, 19 and 20. FIG. 18 is a graph showing the inhibition of 786-0 tumor growth by systemic treatment with recombinant endostatin. Time in days after treatment is shown on the x-axis and tumor volume in mm$^3$ is shown on the y-axis. Intraperitoneal injection of endostatin was given at 10 mg/kg/day, starting on day 1 (arrow). Each time point represents the average of five mice in each group and the error bar represents S.E.M. Treatments are control PBS (○), endostatin from yeast (●), His.endostatin from yeast (x) and His.endostatin from bacteria (□). On the fifth day after treatment there was a difference between control (963 mm$^3$) and treated tumors. Yeast endostatin-treated tumors were 405 mm$^3$, bacterially-produced endostatin-treated tumors were 442 mm$^3$, and His.endostatin-treated tumors were 462 mm$^3$.

FIGS. 19A through 19E are a set of five photographs of 786-0 tumors treated with recombinant endostatin. FIGS. 19A and 19B are control tumors, FIG. 19C shows a tumor treated with yeast-derived endostatin, FIG. 19D shows the effect of His.endostatin from bacteria, and FIG. 19E shows a tumor treated with His.endostatin from yeast. At the end of the treatment period, tumors from control and treated groups were examined grossly under a dissecting microscope. Tumors from the control group were in general larger and more highly vascularized. A 2.5-fold decrease in tumor volume was observed on the fifth day after treatment between control and treated tumors (FIGS. 18 and 19). The growth of the tumor was suppressed in all the treatment groups, and a slower growth rate was seen compared to the control group. Bacterial-(His.Tag) or yeast-derived (with or without His.Tag) endostatin at a dose of 10 μg/kg all worked equally well. On the tenth day after treatment, the tumor volume in the control animals was 1490 mm$^3$, whereas in the treated group it was in the range of 480–570 mm$^3$ (p value<0.005). Endostatin administration did not inhibit tumor growth completely; the growth of the tumors slowed, with a marginal increase in volume during the treatment period.

Example 12

Two Closely Related C-Terminus Endostatin Mutants Generated in *E. coli* Show Markedly Differing In Vivo Activity in RCC The RCC tumor model described above was used in a second set of experiments with endostatin and mutants EM 1 and EM 2, produced in the prokaryotic system in Example 1, above. The daily dosage was 20 mg of the protein per kg body weight, injected intraperitoneally. The initial tumor volume was 150–200 mm$^3$. Wild type endostatin, also produced in the pET28(a) vector, was given at 20 mg/kg body weight for the experiment as a positive control and PBS was given as a negative control.

The results are shown in FIG. 20, which is a graph showing days after treatment on the x-axis, and tumor volume on the y-axis. Each time point represents the average of five mice in each group. Treatments were control PBS (○), wild type His.endostatin from bacteria (dotted line, ●), EM 1 from bacteria (dashed line, ∆), and EM 2 from bacteria (solid line, ♦). Intraperitoneal injection was started on day 1 (arrow). Nine days after treatment, the difference between groups was apparent (FIG. 20). On the eleventh day after treatment, the tumor volume in the control group (397 mm$^3$) was approximately twice that of the two treated groups: endostatin (182 mm$^3$) or EM 1 (259 mm$^3$). However, on the same day, the tumor volume of the EM 2-treated group (389 mm$^3$) was similar to that of the control group (397 mm$^3$). Significance was at the 90% confidence level between the EM 2 and endostatin groups and 95% confidence level between endostatin and control groups. Dropping the value of the largest and smallest tumors on day 11 in each group increased the confidence level to 95% between EM 2 and EM 1 and between EM 2 and endostatin. Therefore, the EM 1 protein retained the native biological activity of endostatin, whereas EM 2, with its further deletion of 8 amino acids, did not. In addition, two of the five mice in the endostatin group and one of the five in the EM 1 group had no detectable tumor at the end of the treatment period.

Example 13

Annexin V-FITC assay

Annexin V, a calcium dependent phospholipid binding protein with a high affinity for phosphtidylserine (PS) was used to detect early stage apoptosis. After initiation of apoptosis, most cell types translocate the membrane phospholipid phosphatidylserine (PS) from the inner surface of the plasma membrane to the outside. PS can be detected by staining with an FITC conjugate of Annexin V, 38 kDa protein that binds naturally to PS. During programmed all death (PCD) externalization typically precedes membrane bleb formation and DNA fragmentation.

Briefly, 200,000 cells were plated onto a fibronectin-coated 6-well plate in DMEM containing 2% FBS and 3 ng/ml of bFGF. Different concentrations of recombinant mouse endostatin were added to each well, and cells were harvested and processed 18 hours after treatment. For the time course study, 10 µg/ml of endostatin was added and cells were processed after 3, 4, 6, 12, and 18 hours. Human recombinant TNF-α (40 ng/ml) was used as a positive control. The cells were washed in PBS and resuspended in binding buffer (10 mM HEPES/NaOH, pH 7.4, 140 mM NaCl, 2.5 mM CaCl$_2$). Annexin V-FITC was added to a final concentration of 100 ng/ml, and the cells were incubated in the dark for 10 minutes, then washed again in PBS and resuspended in 300 ml of binding buffer. 10 µl of propidium iodide (PI) was added to each sample prior to flow cytometric analysis. The cells were analyzed using a Becton Dickinson FACStar plus flow cytometer. Electronic compensation was used to eliminate bleed-through fluorescence. In each sample, a minimum of 10,000 cells were counted and stored in listmode. Data analysis was performed with standard Cell Quest software (Becton-Dickinson). The quadrant settings were set so that the negative control allowed less than 1% positivity. Endostatin was added to non-endothelial cells (NIH3T3 and 786-0) at 10 µg/ml and the cells were processed and analyzed as described above.

Endostatin at 10 µg/ml showed a distinct shift in Annexin fluorescence intensity. The mean fluorescence intensity difference between control and endostatin treated cell was significant (p=0.01) at 5 and 101 g/ml. The shift in fluorescence intensity was similar for endostatin at 10 µg/ml and the positive control TNF-α (40 ng/ml). Concentrations of endostatin below 0.1 µg/ml did not show any significant Annexin V positivity. In order to investigate the earliest time point at which endostatin caused externalization of PS, a time course experiment was conducted. The effect of endostatin was significant (p=0.01) at 12 hours after treatment. Time points before 6 hours did not show a difference between control and treated samples.

Morphological examination of FACS analyzed samples with fluorescence microscopy (Nikon) showed Annexin V staining localized to the cell membrane at 12 hours with no staining in the cytoplasm. During this period, the majority of the cells were negative for PI, implicating the early stage of apoptosis. With increased exposure time (24–36 hours), in addition to membrane staining with Annexin V some of the cells turned positive for PI, consistent with a more advanced stage of apoptosis.

Similar levels of Annexin V staining were observed in two other endothelial cell lines studied, BAE and BCE. We have also tested the effect of human endostatin on these three bovine endothelial cell lines. We failed to detect Annexin V staining in the presence of human endostatin added to these cells, whereas when human endothelial cell lines were used (HUVE and HMVE-L), it resulted in a marked shift in Annexin V fluorescence (manuscript in preparation). These data indicate that apoptosis, as assessed by Annexin V staining, occurs in diverse endothelial cells in response to mouse and human endostatin.

With regard to non-endothelial cells, 786-O and NIH3T3 cells failed to show any distinct annexin positivity. In addition, other non-endothelial cells (IMR-90, A10 and H9c2 (2-1)-myoblast) were screened and no effect of endostatin was found. Based on these results, endostatin's action appears to be selective for endothelial cells.

Example 14

Caspase 3 Assay

Caspase 3 (CPP32) is an intracellular protease activated early during apoptosis of mammalian cells and initiates cellular breakdown by degrading specific structural, regulatory, and DNA repair proteins. This protease activity can be measured spectrophotometrically by detection of the chromophore (p-nitroanilide) after cleavage from the labeled substrate (DEVD-pNA).

This assay was performed in either a 75-cm$^2$ tissue culture flask or in fibronectin-coated 6-well plates. The 6-well plates were seeded with 0.5–1×10$^6$ cells per well, and the flasks were seeded with 2×10 cells. The cells were maintained overnight in DMEM with 10% FBS. The following day, the old medium was replaced with fresh medium (2% FBS), and the cells were incubated overnight at 37° C. Following starvation, the cells were stimulated with bFGF (3 ng/ml) in DMEM (2% FBS). Along with bFGF, yeast endostatin (10 µg/ml final concentration) was added and the cells grown for 24 hours. For the control plate, only the PBS buffer was added. As a positive control, TNF-α was used at a final concentration of 20 ng/ml. After 24 hours, the supernatant cells were centrifuged and collected. The wells (flasks) were trypsinized to collect the attached cells and combined with the supernatant cells. The cells were counted and resuspended in cell lysis buffer (Clontech, Palo Alto, Calif., USA) at a concentration of 4×10 cells/ml. The rest of the protocol followed the manufacturer's instruction (Clontech, Palo Alto, Calif., USA). A specific inhibitor of caspase 3, DEVD-fmk, was used to confirm the specificity as suggested by the manufacturer. The absorbance was measured in a microplate reader (BiORad, Hercules, Calif., USA) at 405 nm. Fold-increase in protease activity (caspase 3) was determined by comparing the results of the induced sample (yeast endostatin or TNF-α) with the uninduced control. Similarly non-endothelial cells (NIH3T3 and H9c2 (2-1)-myoblast were used and analyzed as described above.

Figure 21:
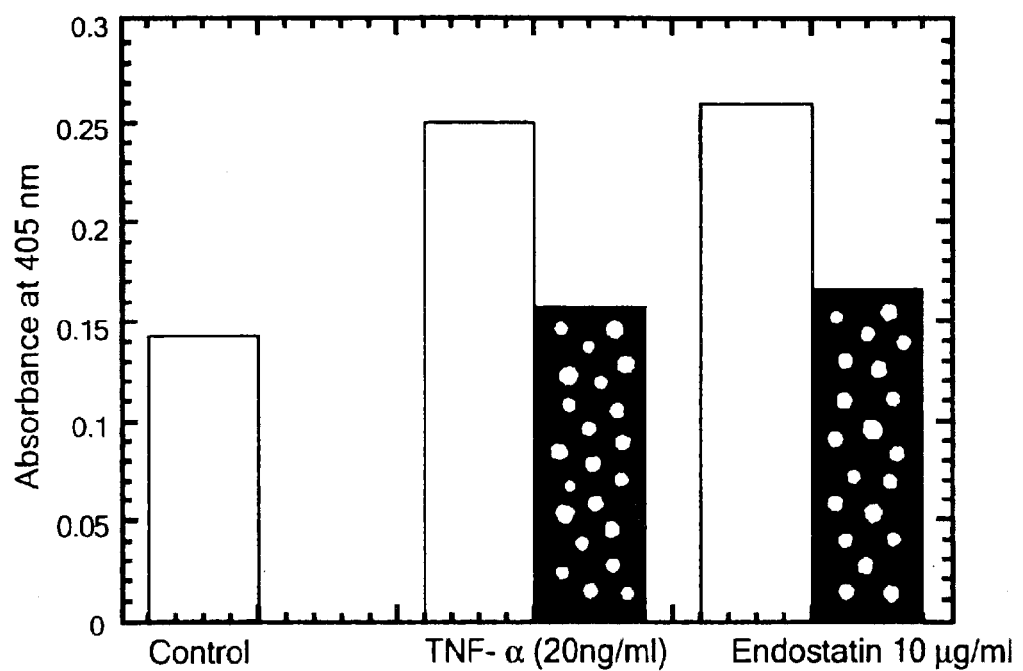
FIG. 21 is a bar graph showing increased caspase 3 activity due to endostatin treatment. Absorbance at 405 nm is shown on the y-axis, and treatments (control, TNF-α (10 ng/ml), endostatin (10 μg/ml) are shown on the x-axis. The pairs of bars for each treatment the $A_{405}$ reading in the presence (open bars) or absence (shaded bars) of the inhibitor DEVD-fmk.
Figure 22:
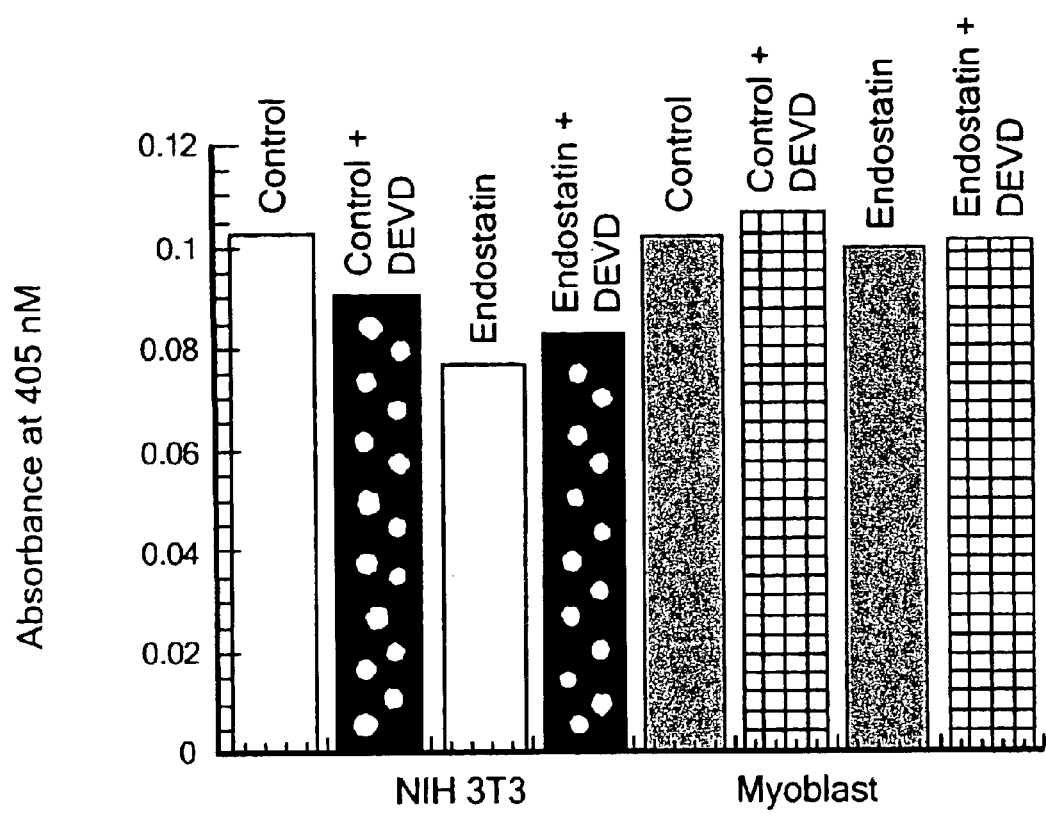
FIG. 22 is a bar graph showing caspase 3 activity in non-endothelial cells. Absorbance at 405 nm is shown on the y-axis, and x-axis displays treatments (control, control+ DEVD, endostatin (10 μg/ml), endostatin (10 μg/ml)+ DEVD) for NIH3T3 and H9c2 (2-1)-myoblast cells, repectively.

A time course experiment was first performed with 10 μg/ml of endostatin, looking for an increase in caspase 3 activity. There was no difference in caspase 3 activity between the treated and the control samples at 2, 4, 8, and 14 hours. However, caspase 3 activity 24 hours after treatment with endostatin was elevated over controls. The caspase activity of the endostatin and TNF-α (positive control) treated samples is shown in FIG. 21. When compared to controls, endostatin treated cells showed a 1.8-fold increase in caspase 3 activity after 24 hours, whereas TNF-α gave a comparable (1.75-fold) increase. The assay was repeated at least five times with similar results. When a specific inhibitor of caspase 3 (DEVD-fmk) was included in the same samples, the protease activity was at baseline (comparison of the dark box to the corresponding white box), indicating that the increase in the measured activity was specific for caspase 3. FIG. 22 shows that for NIH3T3 cells only, a marginal increase in caspase-3 was seen, whereas in myoblast cells there was no difference in caspase-3 levels between treated and control cultures.

Example 15

Microscopic Detection of TUNEL Staining

Fragmentation of nuclear DNA is one of the distinct morphological changes occurring in the nucleus of an apoptotic cell. A TUNEL (terminal deoxynucleotidyl transferase-mediated dUTP nick-end-labeling) assay was performed on endostatin, TNF-α treated and control cells. For adherent cells, C-PAE cells were seeded at a density of 5,000 cells per well on fibronectin coated (10 μg/ml) Lab-Tek chamber slides and grown in 0.4 ml of DMEM medium with 10% FBS. After two days, the old medium was aspirated and fresh DMEM with 2% FBS was added and the cells were starved overnight. The following day, 0.36 ml of new medium (with 2% FBS) containing 3 ng/ml bFGF was added along with yeast endostatin (10 μg/ml) or TNF-α (20 ng/ml). For control samples, fresh medium (2% FBS) containing bFGF (3 ng/ml) was added. Following induction (24 hours), the slides were washed twice with PBS, and subsequently fixed in fresh 4% formaldehyde/PBS at 4° C. for 25 minutes. The slides were washed in PBS and the cells permeabilized in 0.2% Triton X-100/PBS for 5 minutes on ice, then washed with fresh PBS twice for 5 minutes each at room temperature, and the TUNEL assay performed as described below.

The TUNEL assay was performed as described in the ApoAlert DNA fragmentation assay kit user manual (Clontech, Palo Alto, Calif., USA), except that the final concentration of propidium iodide (Sigma, St. Louis, Mo., USA) used was 1 μg/ml. After the assay, a drop of anti-fade solution was added and the treated portion of the slide was covered with a glass coverslip with the edges sealed with clear nail polish. Slides were viewed immediately under a fluorescent microscope using a dual filter set for green (520 nm) and red fluorescence (>620 nm). The images were captured using a digital microscope (Nikon Microphot-SA) and processed using SPOT software version 1.1.02. For the positive control (TNF-α), 5 fields random were chosen, and for the samples, 15 random fields were chosen. The number of green and red cells per field were then counted, and the percent of green divided by the number of red cells in a given field was determined. An average (with S.E.M.) of the different fields was then calculated.

For cells in suspension, floating cells were collected by centrifugation at 300×g for 10 minutes at 4° C. The old medium was aspirated, and the cells were resuspended in 500 ml of PBS (pH 7.4). Cells were centrifuged again, the PBS removed, and the =pellet was resuspended in 75 ml of fresh PBS. Resuspended cells were spread on a poly-L-lysine coated slide (Jersey lab supply) using a clean slide. The cells were fixed by immersing the slides in fresh 4% formaldehyde/PBS at 4° C. for 25 min. The rest of the protocol was carried out as described above.

In the presence of the enzyme TdT, both endostatin and TNF-α treated slides showed numerous positive cells under green fluorescence, whereas no positive cells were seen in the control. Without the enzyme, the endostatin treated slide showed background cell fluorescence.

Figure 23:
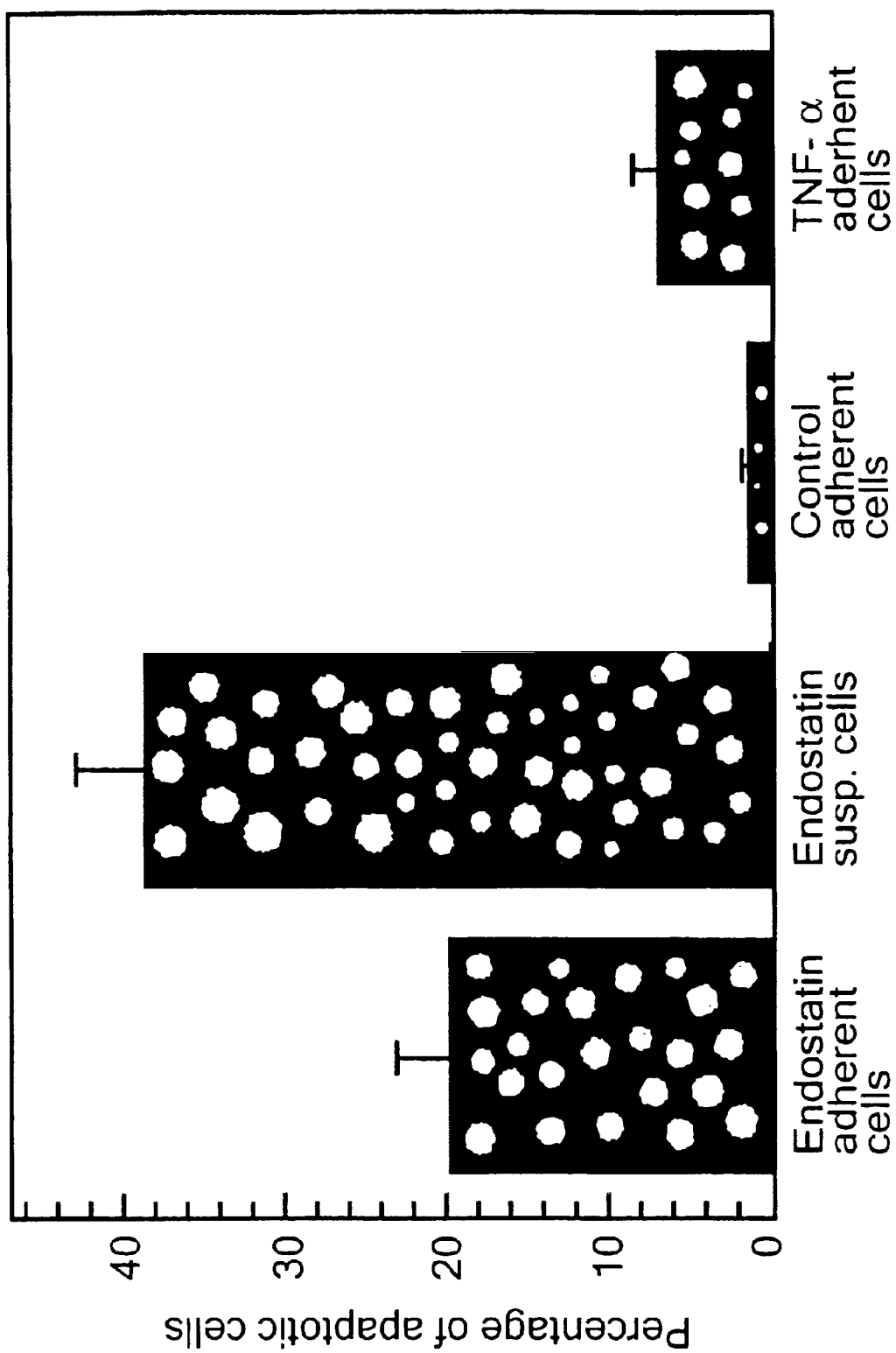
FIG. 23 is a bar graph showing quantitative determination of apoptosis, as determined by the TUNEL assay. The treatments are shown on the x-axis, and are endostatin-treated adherent cells, endostatin-treated suspension cells, control adherent cells, and TNF-α-treated adherent cells. Percentage of apoptotic cells are shown on the y-axis.

The number of apoptotic cells in several fields were counted, and the percent of apoptotic cells (green divided by the number of red cells per field) is plotted in FIG. 23, which is a bar graph. The apoptosis rate in the control cells was 1.24%. In the endostatin treated cells, a 30-fold increase in the apoptosis rate was observed in suspension cells (38.3%), while a 15-fold increase was observed in the attached cells (19.4%). With TNF-α, the apoptosis rate was 6.4%. In contrast, the percent of TUNEL-positive in the angiostatin treated BCE (bovine adrenal cortex capillary endothelial) cells was 2% when compared with the control cells (1.2%), a 1.6 fold increase, suggesting that endostatin is a stronger apoptotic agent than angiostatin.

Example 16

Bcl-2 and Bax Expression by Western Blot Analysis

C-PAE cells ($1 \times 10^6$) were seeded in 10 cm petri dishes precoated with fibronectin (10 μg/ml) in the presence of 2% FBS containing 3 ng/ml bFGF. Endostatin was added at 10 μg/ml, and cells were harvested at 12, 24, and 28 hours after treatment. Cells were washed thrice in PBS buffer pH, 7.4 and the cells were resuspended in 1 ml of 1×EBC buffer (50 mM Tris-HCl, pH 8.0, 120 mM NaCl, 1% Nonidet P-40) containing freshly added complete protease inhibitor tablet (Boerhinger Mannheim), 100 mg/ml Pefabloc, 1 mg/ml Pepstatin. The protein concentration in whole cell lysate was measured by the BCA method. 30 mg of whole cell extract was loaded onto a 4–15% gradient polyacrylamide gel. Transfer was performed using a semi-dry transblot apparatus (BiORad, Hercules, Calif., USA). The membrane was blocked in wash buffer (1×TBS) with 5% non fat dry milk and incubated at 37° C. for 1 hour. Goat antibody directed against human Bcl-2 (N-19) {sc492-G} was purchased from Santa Cruz Biotechnology (Santa Cruz, Calif., USA). Affinity purified mouse polyclonal antibody against Bax (B-9) {sc7490} and Bcl-XS/L {sc1690} were purchased from the same manufacturer. Polyclonal anti-actin antibody (Sigma, St. Louis, Mo., USA) was used to normalize for protein loading. Secondary antibodies were anti-goat, mouse and rabbit immunoglobulin conjugated to horseradish peroxidase (Amersham Corp., Arlington Heights, Ill., USA). The immunoreactivity was detected with an enhanced chemiluminescence reagent (Pierce Chemical Co., Rockford, Ill., USA). Images were scanned using a flat bed scanner (Scan-Jet 4C) and quantitated by the NIH Image 1.61 software. Normalization was done by dividing the Bcl-2 signal by that of actin within each experiment.

Figure 24A:
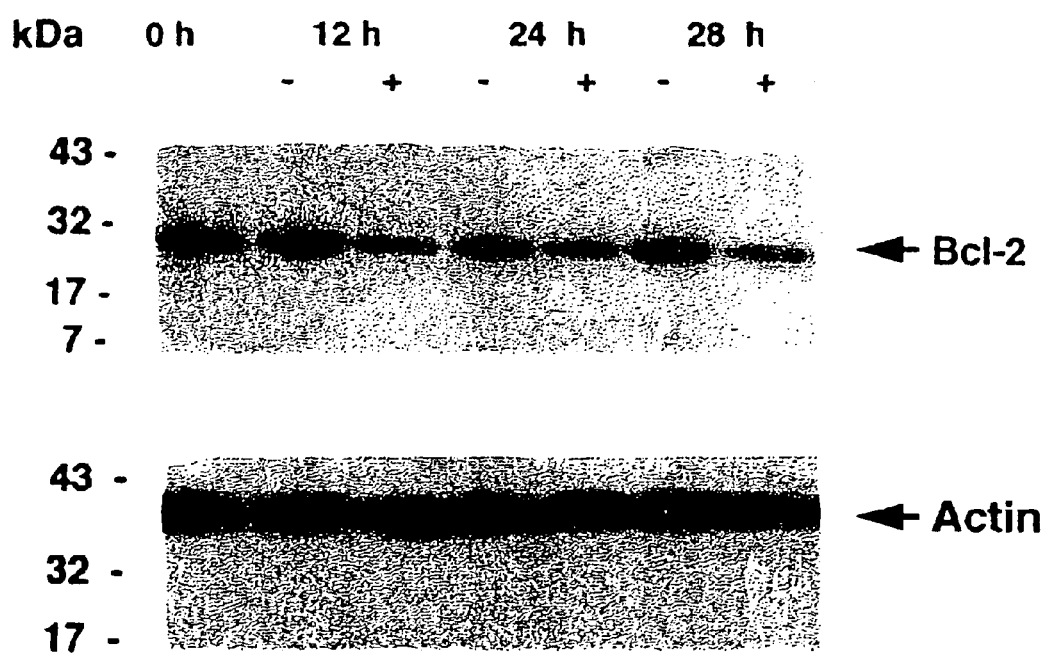
FIGS. 24A and 24B are a Western blot analyses of C-PAE cell lysate for Bcl-2 protein levels, and an immunoblot detecting total cell lysate for Bax expression levels, respectively. C-PAE cells were treated with either no endostatin (−) or endostatin (10 μg/ml) (+) for the indicated period of time 0, 12, 24, 28 hours). Actin probing is also shown.
Figure 24B:
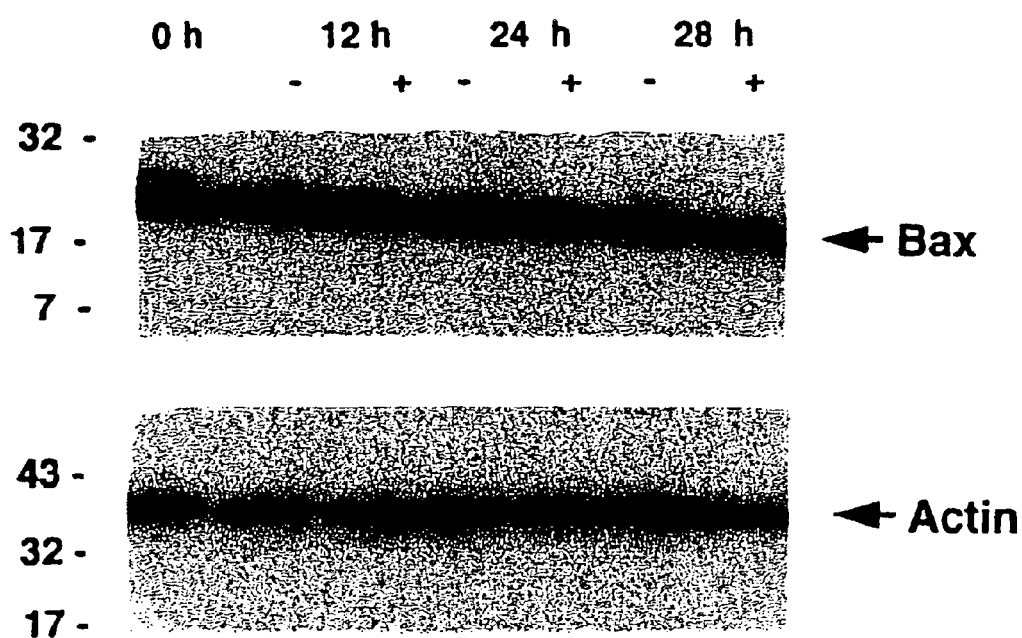

Anti-apoptotic members such as Bcl-2 and BCl-$X_L$ prevent PCD in response to numerous stimuli. Conversely, pro-apoptotic proteins such as Bax and Bak can accelerate cell death; and in certain cases, they are sufficient to cause apoptosis independent of additional signals. Whole cell extract of endostatin treated and control C-PAE cells were tested for Bcl-2 and Bax expression levels. In growth arrested C-PAE cells, Bcl-2 expression was high. It was relatively constant up to 28 hours; in contrast, endostatin treated cells showed marked decrease in Bcl-2, as is show in FIG. 24A. Densitometry revealed that the levels of Bcl-2 compared to control was 1.2, 1.5, and 3 fold less at 12, 24, and 28 hours respectively after treatment, with actin levels used as normalization controls. In contrast, Bax expression was similar between control and treated cultures (FIG. 24B).

Figure 25A:
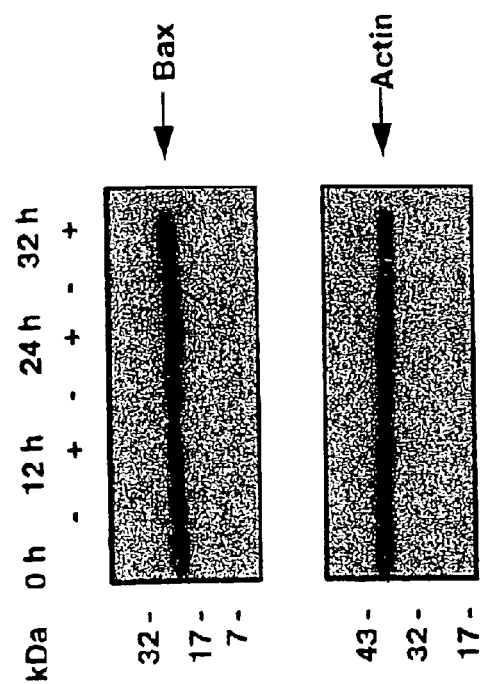
FIGS. 25A, 25B, 25C and 25D are a set of two Western blot analyses (FIGS. 25A and 25B) and two immunoblots (FIGS. 25C and D) of non-endothelial cell lysate for Bax protein levels. Cells were treated with either no endostatin (−) or endostatin (10 μg/ml) (+) for the indicated period of time 0, 12, 24, 28, 32 hours). Actin probing is also shown.
Figure 25B:
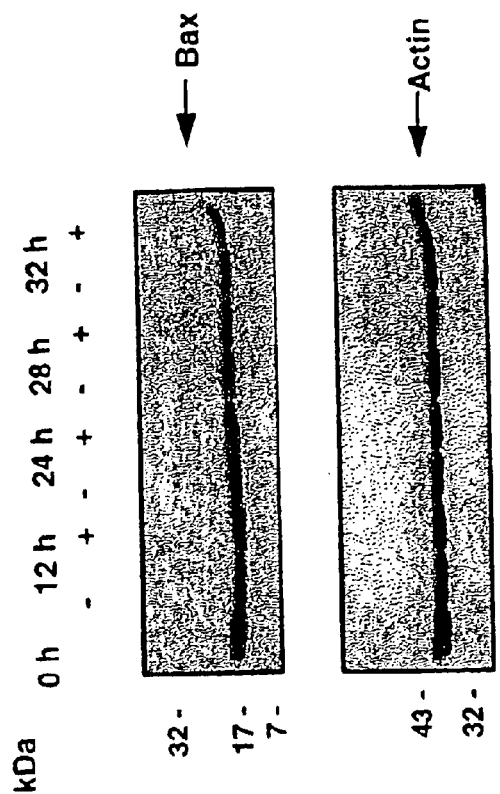
Figure 25C:
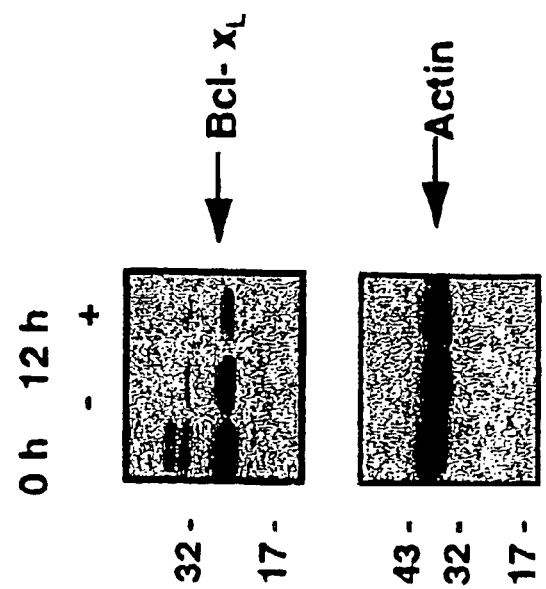
Figure 25D:
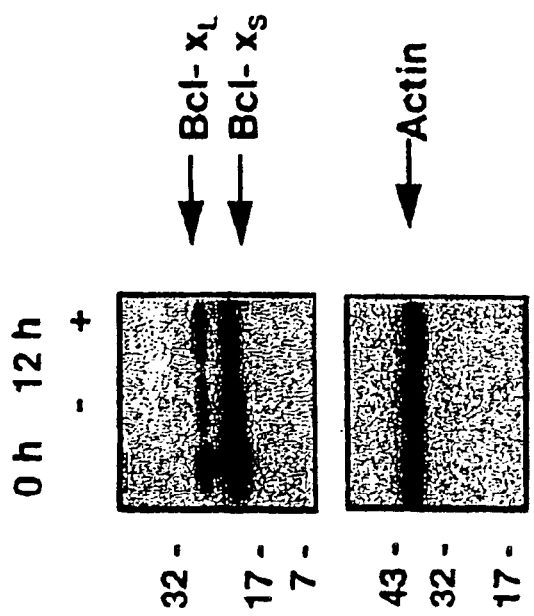

Bcl-2 protein was not detected in both NIH3T3 and IMR-90 cells. Bax expression levels were not affected by endostatin treatment in these cell lines, as is shown in FIGS. 25A and 25B. In C-PAE cells, at the early time point (12 hours), Bcl-XL level was reduced by 2 fold, whereas in NIH3T3 cell its expression was unchanged (FIGS. 25C and 25D). Interestingly, only the larger pro-apoptotic form of Bcl-X in C-PAE was detected whereas, in NIH3T3 both smaller and larger forms were detected.

These findings suggest that endostatin exerts its regulatory activity by altering Bcl-2 expression. Interestingly, VEGF has been shown to augment Bcl-2 levels in endothelial cells. Since endostatin antagonizes VEGF's proliferative effects, Bcl-2 appears to be one point of regulation. Recent studies indicate that the Bcl-2 protein binds to other proteins, such as Bax, Bcl XS, Bik and Bad, which ultimately enhance cell survival (Newton, K, and Strasser, A. (1998) *Curr. Opin. Genet. Dev.* 8:68–75; Jacobson, M. D. (1997) *Curr. Biol.* 7:R277–81). The function of another Bcl-2 homologue, Bax remains enigmatic. Bcl-2 and BCl-$X_L$ function through heterodimerization with Bax, and overexpression of Bax accelerates apoptosis. Recently, it was shown that FGF-2 inhibited endothelial cell apoptosis by Bcl-2 dependent and independent mechanisms. In this study, differences in Bcl-2 (and Bcl-$X_L$) expression were seen in endostatin-treated cultures but no difference in Bax levels. It is possible that Bcl-2 may act independently of Bax, as has been shown for T cells.

Equivalents

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An isolated polypeptide comprising amino acids 1–175 of SEQ ID NO:2, wherein said isolated polypeptide does not contain the amino acid sequence set forth in SEQ ID NO:25, and wherein the isolated polypeptide has anti-angiogenic activity.

2. A fusion protein, comprising the isolated polypeptide of claim 1.

3. A composition comprising, as a biologically active ingredient the polypeptide of claim 1.

4. The composition of claim 3, and a pharmaceutically compatible carrier.

5. A composition comprising, as a biologically active ingredient, the fusion protein of claim 2.

6. A protein consisting of amino acids 1–175 of SEQ ID NO:2.

* * * * *

SEQUENCE LISTING

```
<160> NUMBER OF SEQ ID NOS: 25

<210> SEQ ID NO 1
<211> LENGTH: 555
<212> TYPE: DNA
<213> ORGANISM: Mus musculus
<220> FEATURE:
<221> NAME/KEY: misc_feature
<222> LOCATION: (1)...(525)
<223> OTHER INFORMATION: protein EM1
<221> NAME/KEY: misc_feature
<222> LOCATION: (1)...(501)
<223> OTHER INFORMATION: protein EM2
<221> NAME/KEY: CDS
<222> LOCATION: (1)...(552)

<400> SEQUENCE: 1 cat act cat cag gac ttt cag cca gtg ctc cac ctg gtg gca ctg aac        48
His Thr His Gln Asp Phe Gln Pro Val Leu His Leu Val Ala Leu Asn
 1               5                  10                  15 acc ccc ctg tct gga ggc atg cgt ggt atc cgt gga gca gat ttc cag        96
Thr Pro Leu Ser Gly Gly Met Arg Gly Ile Arg Gly Ala Asp Phe Gln
            20                  25                  30 tgc ttc cag caa gcc cga gcc gtg ggg ctg tcg ggc acc ttc cgg gct       144
Cys Phe Gln Gln Ala Arg Ala Val Gly Leu Ser Gly Thr Phe Arg Ala
        35                  40                  45 ttc ctg tcc tct agg ctg cag gat ctc tat agc atc gtg cgc cgt gct       192
Phe Leu Ser Ser Arg Leu Gln Asp Leu Tyr Ser Ile Val Arg Arg Ala
    50                  55                  60 gac cgg ggg tct gtg ccc atc gtc aac ctg aag gac gag gtg cta tct       240
Asp Arg Gly Ser Val Pro Ile Val Asn Leu Lys Asp Glu Val Leu Ser
65                  70                  75                  80 ccc agc tgg gac tcc ctg ttt tct ggc tcc cag ggt caa ctg caa ccc       288
```

```
                                                                             -continued Pro Ser Trp Asp Ser Leu Phe Ser Gly Ser Gln Gly Gln Leu Gln Pro
                85                  90                  95 ggg gcc cgc atc ttt tct ttt gac ggc aga gat gtc ctg aga cac cca    336
Gly Ala Arg Ile Phe Ser Phe Asp Gly Arg Asp Val Leu Arg His Pro
            100                 105                 110 gcc tgg ccg cag aag agc gta tgg cac ggc tcg gac ccc agt ggg cgg    384
Ala Trp Pro Gln Lys Ser Val Trp His Gly Ser Asp Pro Ser Gly Arg
        115                 120                 125 agg ctg atg gag agt tac tgt gag aca tgg cga act gaa act act ggg    432
Arg Leu Met Glu Ser Tyr Cys Glu Thr Trp Arg Thr Glu Thr Thr Gly
    130                 135                 140 gct aca ggt cag gcc tcc tcc ctg ctg tca ggc agg ctc ctg gaa cag    480
Ala Thr Gly Gln Ala Ser Ser Leu Leu Ser Gly Arg Leu Leu Glu Gln
145                 150                 155                 160 aaa gct gcg agc tgc cac aac agc tac atc gtc ctg tgc att gag aat    528
Lys Ala Ala Ser Cys His Asn Ser Tyr Ile Val Leu Cys Ile Glu Asn
                165                 170                 175 agc ttc atg acc tct ttc tcc aaa tag                                555
Ser Phe Met Thr Ser Phe Ser Lys
            180

<210> SEQ ID NO 2
<211> LENGTH: 184
<212> TYPE: PRT
<213> ORGANISM: Mus musculus

<400> SEQUENCE: 2

His Thr His Gln Asp Phe Gln Pro Val Leu His Leu Val Ala Leu Asn
 1               5                  10                  15

Thr Pro Leu Ser Gly Gly Met Arg Gly Ile Arg Gly Ala Asp Phe Gln
            20                  25                  30

Cys Phe Gln Gln Ala Arg Ala Val Gly Leu Ser Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Gly Ser Val Pro Ile Val Asn Leu Lys Asp Glu Val Leu Ser
65                  70                  75                  80

Pro Ser Trp Asp Ser Leu Phe Ser Gly Ser Gln Gly Gln Leu Gln Pro
                85                  90                  95

Gly Ala Arg Ile Phe Ser Phe Asp Gly Arg Asp Val Leu Arg His Pro
            100                 105                 110

Ala Trp Pro Gln Lys Ser Val Trp His Gly Ser Asp Pro Ser Gly Arg
        115                 120                 125

Arg Leu Met Glu Ser Tyr Cys Glu Thr Trp Arg Thr Glu Thr Thr Gly
    130                 135                 140

Ala Thr Gly Gln Ala Ser Ser Leu Leu Ser Gly Arg Leu Leu Glu Gln
145                 150                 155                 160

Lys Ala Ala Ser Cys His Asn Ser Tyr Ile Val Leu Cys Ile Glu Asn
                165                 170                 175

Ser Phe Met Thr Ser Phe Ser Lys
            180

<210> SEQ ID NO 3
<211> LENGTH: 26
<212> TYPE: DNA
<213> ORGANISM: Artificial Sequence
<220> FEATURE:
<223> OTHER INFORMATION: Oligonucleotide
```

-continued

```
<400> SEQUENCE: 3
ggcatatgca tactcatcag gacttt                                          26

<210> SEQ ID NO 4
<211> LENGTH: 26
<212> TYPE: DNA
<213> ORGANISM: Artificial Sequence
<220> FEATURE:
<223> OTHER INFORMATION: Oligonucleotide

<400> SEQUENCE: 4
aactcgagct atttggagaa agaggt                                          26

<210> SEQ ID NO 5
<211> LENGTH: 24
<212> TYPE: PRT
<213> ORGANISM: Artificial Sequence
<220> FEATURE:
<223> OTHER INFORMATION: Leader peptide on protein produced by
      prokaryotic expression system pET17b, mouse endostatin begins
      immediately after.

<400> SEQUENCE: 5

Met Gly His His His His His His His His His Ser Ser Gly His
 1               5                  10                  15

Ile Asp Asp Asp Asp Lys His Met
            20

<210> SEQ ID NO 6
<211> LENGTH: 28
<212> TYPE: DNA
<213> ORGANISM: Artificial Sequence
<220> FEATURE:
<223> OTHER INFORMATION: Oligonucleotide

<400> SEQUENCE: 6
aagcggccgc ctatttggag aaagaggt                                        28

<210> SEQ ID NO 7
<211> LENGTH: 21
<212> TYPE: PRT
<213> ORGANISM: Artificial Sequence
<220> FEATURE:
<223> OTHER INFORMATION: Leader peptide on protein produced by
      prokaryotic expression system pET28a, mouse endostatin begins
      immediately after.

<400> SEQUENCE: 7

Met Gly Ser Ser His His His His His His Ser Ser Gly Leu Val Pro
 1               5                  10                  15

Arg Gly Ser His Met
            20

<210> SEQ ID NO 8
<211> LENGTH: 33
<212> TYPE: DNA
<213> ORGANISM: Artificial Sequence
<220> FEATURE:
<223> OTHER INFORMATION: Oligonucleotide

<400> SEQUENCE: 8
ttccatatgc atactcatca ggactttcag cca                                  33

<210> SEQ ID NO 9
<211> LENGTH: 35
```

```
<212> TYPE: DNA
<213> ORGANISM: Artificial Sequence
<220> FEATURE:
<223> OTHER INFORMATION: Oligonucleotide

<400> SEQUENCE: 9
ttagcggccg cctactcaat gcacaggacg atgta                              35

<210> SEQ ID NO 10
<211> LENGTH: 38
<212> TYPE: DNA
<213> ORGANISM: Artificial Sequence
<220> FEATURE:
<223> OTHER INFORMATION: Oligonucleotide

<400> SEQUENCE: 10
ttagcggccg cctagttgtg gcagctcgca gctttctg                           38

<210> SEQ ID NO 11
<211> LENGTH: 26
<212> TYPE: DNA
<213> ORGANISM: Artificial Sequence
<220> FEATURE:
<223> OTHER INFORMATION: Oligonucleotide

<400> SEQUENCE: 11
gggaattcca tactcatcag gacttt                                        26

<210> SEQ ID NO 12
<211> LENGTH: 32
<212> TYPE: DNA
<213> ORGANISM: Artificial Sequence
<220> FEATURE:
<223> OTHER INFORMATION: Oligonucleotide

<400> SEQUENCE: 12
aagaattcca tcatcatcat catcacagca gc                                 32

<210> SEQ ID NO 13
<211> LENGTH: 26
<212> TYPE: PRT
<213> ORGANISM: Artificial Sequence
<220> FEATURE:
<223> OTHER INFORMATION: Leader peptide on protein produced by
      eukaryotic yeast expression system pPICZaA, mouse endostatin
      protein begins immediately after.

<400> SEQUENCE: 13

Glu Phe Met Gly His His His His His His His His His Ser Ser
 1               5                  10                  15

Gly His Ile Asp Asp Asp Asp Lys His Met
            20                  25

<210> SEQ ID NO 14
<211> LENGTH: 44
<212> TYPE: DNA
<213> ORGANISM: Artificial Sequence
<220> FEATURE:
<223> OTHER INFORMATION: Oligonucleotide

<400> SEQUENCE: 14
tttgaattcg cccacagcca ccgcgacttc cagccggtgc tcca                    44

<210> SEQ ID NO 15
<211> LENGTH: 44
<212> TYPE: DNA
```

<210> SEQ ID NO 15
<211> LENGTH: 44
<212> TYPE: DNA
<213> ORGANISM: Artificial Sequence
<220> FEATURE:
<223> OTHER INFORMATION: Oligonucleotide

<400> SEQUENCE: 15
aaaagcggcc gcctacttgg aggcagtcat gaagctgttc tcaa         44

<210> SEQ ID NO 16
<211> LENGTH: 51
<212> TYPE: DNA
<213> ORGANISM: Artificial Sequence
<220> FEATURE:
<223> OTHER INFORMATION: Oligonucleotide

<400> SEQUENCE: 16 tttttttgaat tcatttcaag tgccaattat gagaagcctg ctctgcattt g     51

<210> SEQ ID NO 17
<211> LENGTH: 50
<212> TYPE: DNA
<213> ORGANISM: Artificial Sequence
<220> FEATURE:
<223> OTHER INFORMATION: Oligonucleotide

<400> SEQUENCE: 17
aagaatgcgg ccgcttactt cctagcgtct gtcatgaaac tgttttcgat      50

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide

<400> SEQUENCE: 18
aattccatca ccatcaccat cacg         24

<210> SEQ ID NO 19
<211> LENGTH: 24
<212> TYPE: DNA
<213> ORGANISM: Artificial Sequence
<220> FEATURE:
<223> OTHER INFORMATION: Oligonucleotide

<400> SEQUENCE: 19
aattcgtgat ggtgatggtg atgg         24

<210> SEQ ID NO 20
<211> LENGTH: 8
<212> TYPE: PRT
<213> ORGANISM: Artificial Sequence
<220> FEATURE:
<223> OTHER INFORMATION: Leader peptide on protein produced by
      eukaryotic yeast expression system pPICZaA, mouse endostatin
      protein begins immediately after.

<400> SEQUENCE: 20

Glu Phe His His His His His His
 1               5

<210> SEQ ID NO 21
<211> LENGTH: 42
<212> TYPE: DNA
<213> ORGANISM: Artificial Sequence
<220> FEATURE:
<223> OTHER INFORMATION: Oligonucleotide -continued

```
<400> SEQUENCE: 21
ttccatatga tatactcctt tgatggtcga gacataatga ca                              42

<210> SEQ ID NO 22
<211> LENGTH: 47
<212> TYPE: DNA
<213> ORGANISM: Artificial Sequence
<220> FEATURE:
<223> OTHER INFORMATION: Oligonucleotide

<400> SEQUENCE: 22
aatgcggccg cttacttcct agcgtctgtc atgaaactgt tttcgat                         47

<210> SEQ ID NO 23
<211> LENGTH: 23
<212> TYPE: PRT
<213> ORGANISM: Artificial Sequence
<220> FEATURE:
<223> OTHER INFORMATION: Leader peptide on protein produced by
      eukaryotic yeast expression system pPICZaA, apomigren protein
      begins immediately after.

<400> SEQUENCE: 23

Glu Phe Met Gly Ser Ser His His His His His His Ser Ser Gly Leu
 1               5                  10                  15

Val Pro Arg Gly Ser His Met
            20

<210> SEQ ID NO 24
<211> LENGTH: 8
<212> TYPE: PRT
<213> ORGANISM: Mus musculus

<400> SEQUENCE: 24

Ser Tyr Ile Val Leu Cys Ile Glu
 1               5

<210> SEQ ID NO 25
<211> LENGTH: 9
<212> TYPE: PRT
<213> ORGANISM: Mus musculus

<400> SEQUENCE: 25

Asn Ser Phe Met Thr Ser Phe Ser Lys
 1               5
```